(12) United States Patent
Wang et al.

(10) Patent No.: US 11,045,448 B2
(45) Date of Patent: Jun. 29, 2021

(54) PIPERIDINES AS COVALENT MENIN INHIBITORS

(71) Applicant: THE REGENTS OF THE UNIVERSITY OF MICHIGAN, Ann Arbor, MI (US)

(72) Inventors: Shaomeng Wang, Superior Township, MI (US); Angelo Aguilar, Ann Arbor, MI (US); Shilin Xu, Ann Arbor, MI (US); Liyue Huang, Ann Arbor, MI (US); Jeanne Stuckey, Fenton, MI (US); Tianfeng Xu, Ypsilanti, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 13 days.

(21) Appl. No.: 16/497,856

(22) PCT Filed: Mar. 30, 2018

(86) PCT No.: PCT/US2018/025417
§ 371 (c)(1),
(2) Date: Sep. 26, 2019

(87) PCT Pub. No.: WO2018/183857
PCT Pub. Date: Oct. 4, 2018

(65) Prior Publication Data
US 2020/0022953 A1 Jan. 23, 2020

Related U.S. Application Data

(60) Provisional application No. 62/479,520, filed on Mar. 31, 2017.

(51) Int. Cl.
A61K 31/397 (2006.01)
A61K 31/4523 (2006.01)
A61K 31/454 (2006.01)
A61K 31/4709 (2006.01)
A61K 31/5377 (2006.01)
C07D 205/04 (2006.01)
C07D 401/06 (2006.01)
C07D 401/12 (2006.01)
C07D 401/14 (2006.01)
C07D 413/14 (2006.01)

(52) U.S. Cl.
CPC .......... A61K 31/397 (2013.01); A61K 31/454 (2013.01); A61K 31/4523 (2013.01); A61K 31/4709 (2013.01); A61K 31/5377 (2013.01); C07D 205/04 (2013.01); C07D 401/06 (2013.01); C07D 401/12 (2013.01); C07D 401/14 (2013.01); C07D 413/14 (2013.01)

(58) Field of Classification Search
CPC .............. A61K 31/397; A61K 31/4523; A61K 31/454; A61K 31/4709; A61K 31/5377; C07D 205/04; C07D 401/06; C07D 401/12; C07D 401/14; C07D 413/14
See application file for complete search history.

(56) References Cited

U.S. PATENT DOCUMENTS

| | | | |
|---|---|---|---|
| 9,212,180 | B2 | 12/2015 | Grembecka et al. |
| 9,216,993 | B2 | 12/2015 | Grembecka et al. |
| 2009/0298772 | A1 | 12/2009 | Thirman |
| 2011/0065690 | A1 | 3/2011 | Grembecka et al. |

(Continued)

FOREIGN PATENT DOCUMENTS

| | | |
|---|---|---|
| WO | WO-98/54167 A1 | 12/1998 |
| WO | WO-2006/136606 A2 | 12/2006 |

(Continued)

OTHER PUBLICATIONS

Bendele, "Animal Models of Arthritis: Relevance to Human Disease" Toxicol Pathol 1999 27:134-142.
Bendele, "Animal models of rheumatoid arthritis" J Musculoskel Neuron Interact 2001; 1(4):377-385.
International Search Report for Patent Application No. PCT/US2017/030577, dated Jun. 30, 2017.
Borkin et al., Pharmacologic inhibition of the Menin-MLL interaction blocks progression of MLL leukemia in vivo, Cancer Cell, 27(4):589-602 (Apr. 2015).
Cierpicki et al., Challenges and opportunities in targeting the menin-MLL interaction, Future Med. Chem., 6(4):447-62 (Mar. 2014).
He et al., High-affinity small-molecule inhibitors of the menin-mixed lineage leukemia (MLL) interaction closely mimic a natural protein-protein interaction, J. Med Chem., 57(4):1543-56 (Feb. 2014).

(Continued)

Primary Examiner — John Mabry
(74) Attorney, Agent, or Firm — Marshall, Gerstein & Borun LLP

(57) ABSTRACT

The present disclosure provides compounds represented by Formula (I): and the pharmaceutically acceptable salts and solvates thereof, wherein A, $R^{1a}$, $R^{1b}$, $R^{1c}$, $R^{1d}$, $R^2$, $R^3$, $R^{8a}$, $R^{8b}$, $R^{10}$, X, $Z^2$, m, and n are as defined as set forth in the specification. The present disclosure also provides compounds of Formula (I) for use to treat a condition or disorder responsive to menin inhibition such as cancer.

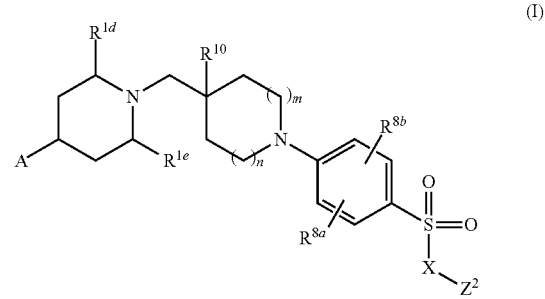

(I)

21 Claims, 6 Drawing Sheets

(56) References Cited

U.S. PATENT DOCUMENTS

| | | | |
|---|---|---|---|
| 2014/0248240 | A1 | 9/2014 | Bair et al. |
| 2014/0275070 | A1 | 9/2014 | Grembecka et al. |
| 2014/0371239 | A1 | 12/2014 | Grembecka et al. |
| 2016/0045504 | A1 | 2/2016 | Grembecka et al. |
| 2016/0046647 | A1 | 2/2016 | Grembecka et al. |
| 2019/0152947 | A1 | 5/2019 | Wang et al. |

FOREIGN PATENT DOCUMENTS

| | | | |
|---|---|---|---|
| WO | WO-2011/060321 A1 | 5/2011 | |
| WO | WO-2013/080036 A1 | 6/2013 | |
| WO | WO-2014200479 A1 | 12/2014 | |
| WO | WO-2016/040330 | 3/2016 | |
| WO | WO-2016/195776 A1 | 12/2016 | |
| WO | WO-2016/197027 A1 | 12/2016 | |
| WO | WO-2017/112768 A1 | 6/2017 | |
| WO | WO-2017/161002 A1 | 9/2017 | |
| WO | WO-2017/161028 A1 | 9/2017 | |
| WO | WO-2017/192543 | 11/2017 | |
| WO | WO-2017/214367 A1 | 12/2017 | |
| WO | WO-2018/053267 A1 | 3/2018 | |
| WO | WO-2018/106818 A1 | 6/2018 | |
| WO | WO-2018/175746 A1 | 9/2018 | |
| WO | WO-2018/226976 A1 | 12/2018 | |
| WO | WO-2019/060365 A1 | 3/2019 | |
| WO | WO-2019/189732 A1 | 10/2019 | |
| WO | WO-2020/069027 A1 | 4/2020 | |
| WO | WO-2020/142557 A1 | 7/2020 | |
| WO | WO-2020/142559 A1 | 7/2020 | |

OTHER PUBLICATIONS

International Application No. PCT/US2018/025417, International Preliminary Report on Patentability, dated Oct. 10, 2019.
International Application No. PCT/US2018/025417, International Search Report and Written Opinion, dated Jun. 20, 2018.
Xu et al., Discovery of Novel Inhibitors Targeting the Menin-Mixed Lineage Leukemia Interface Using Pharmacophore—and Docking-Based Virtual Screening, J. Chem. Inf. Model., 58(9):1847-55 (Sep. 2016).
U.S. Appl. No. 16/098,147, "Piperidines as Menin Inhibitors", filed May 2, 2017, Wang et al.
Aguilar, et al: Structure-Based Discovery of M-89 as a Highly Potent Inhibitor of the Menin-Mixed Lineage Leukemia (Menin-MLL) Protein-Protein Interaction; J. Med. Chem. 2019, 62, 6015-6034.
Argollo, Novel therapeutic targets for inflammatory bowel disease Journal of Autoimmunity (2017), 85, 103-116.
Boniface, Multidisciplinary management for esophageal and gastric cancer Cancer Management and Research 2016:8 39-44.
Brzezinka, et al: Functional diversity of inhibitors tackling the differentiation blockage of MLLrearranged leukemia; Journal of Hematology & Oncology, 2019, 12:66, 1-14.
Burm et al., Synthesis of new bridged tetrahydro-[beta]-carbolines and spiro-fused quinuclidines, Tetrahedron, vol. 57, No. 10, Jan. 1, 2001, pp. 2039-2049.
Damia, Contemporary pre-clinical development of anticancer agents—What are the optimal preclinical models? European Journal of Cancer 2009, 45, 2768-2781.
Garson, Models of ovarian cancer—Are we there yet? Molecular and Cellular Endocrinology 239 (2005) 15-26.
Gentile, HMGB1 as a therapeutic target for sepsis: it's all in the timing! Expert Opinion on Therapeutic Targets, 2014, 18(3), 243-245.
Gerratana, Do platinum salts fit all triple negative breast cancers? Cancer Treatment Reviews, 2016, 48, 34-41.
Jett, Treatment of Small Cell Lung Cancer Diagnosis and Management of Lung Cancer, 3rd ed: American College of Chest Physicians Evidence-Based Clinical Practice Guidelines, Cheste, 2013; 143(5)(Suppl):e400S-e419S.
Johnson et. al. Relationships between drug activity in NCI preclinical in vitro and in vivo models and early clinical trials. British Journal of Cancer 2001, 84, 1424-1431.
Kita et al., Enhancing effects of salt formation on catalytic activity and enantioselectivity for asymmetric hydrogenation of isoquinolinium salts by dinuclear halide-bridged iridium complexes bearing chiral diphosphine ligands, Chemistry—A European Journal, Nov. 28, 2014, vol. 21, pp. 1915-1927.
Klossowski et al, Menin inhibitor MI-3454 induces remission in MLL1-rearranged and NPM1-mutated models of leukemia J Clin Invest. 2020; 130(2):981-997.
Krishnan, Multiple myeloma and persistence of drug resistance in the age of novel drugs (Review) International Journal of Oncology 49: 33-50, 2016.
Krivtsov et al: A Menin-MLL Inhibitor Induces Specific Chromatin Changes and Eradicates Disease in Models of MLLRearranged Leukemia; 2019, Cancer Cell 36, 660-673.
Kuhn et al, Targeting Chromatin Regulators Inhibits Leukemogenic Gene Expression in NPM1 Mutant Leukemia, Cancer Discovery, Oct. 2016, 1166-1181.
Kurmasheva et al., Evaluation of VTP-50469, a menin-MLL1 inhibitor, against Ewing sarcoma xenograft models by the pediatric preclinical testing consortium; Pediatr Blood Cancer. 2020;e28284; 1-4.
Lambert, et al: Direct and Indirect Targeting of HOXA9 Transcription Factor in Acute Myeloid Leukemia, Cancers 2019, 11,837; 1-38.
Ledford, US cancer institute overhauls cell lines Nature Feb. 25, 2016 vol. 530 p. 391.
Marshall, Why have clinical trials in sepsis failed? Trends in Molecular Medicine, Apr. 2014, vol. 20, No. 4 195-203.
Muller et al., Antiviral Strategies in Handbook of Experimental Pharmacology, vol. 189, Chapter 1, 2009, pp. 1-2.
Ocana, Preclinical development of molecular targeted agents for cancer Nat. Rev. Clin. Oncol., 2011, 8, 200-209.
Pilz, Modern multiple sclerosis treatment—what is approved, what is on the horizon Drug Discovery Today Dec. 2008, vol. 13, Nos. 23/24 1013-1025.
Pitta et al., Metalated nitrile and enolate chlorinations, Organic Letters, May 18, 2010, vol. 12, No. 12, pp. 2810-2813.
Poli-De-Figueiredo, Experimental Models of Sepsis and Their Clinical Relevance Shock, 2008, vol. 30, Supplement 1, pp. 53-59.
Prat et al., Synthesis of N-methyl-4-pyridyl-1,2,3,4-tetrahydroisoquinolines via a Pictet-Spengler cyclisation, Journal of Heterocyclic Chemistry, vol. 37, Jul. 1, 2000, pp. 767-771.
Pui et al., Treatment of Acute Lymphoblastic Leukemia New England Journal of Medicine 2006, 354, 166-78.
Sale et al., Models of ovarian cancer metastasis: Murine models Drug Discovery Today: Disease Models 2006, 3, 150-154.
Sanz-Garcia et al., Current and advancing treatments for metastatic colorectal cancer, Expert Opin. Biol. Ther., 16(1):93-110 (2016).
Schober et al., New Advances in the Treatment of Metastatic Pancreatic Cancer Digestion 2015;92:175-184.
Secker et al., MAT2A as key regulator and therapeutic target in MLLr leukemogenesis, Cancers, 12:1342 (2020).
Senter et al., Progress towards small molecule menin-mixed lineage leukemia (MLL) interaction inhibitors with in vivo utility, Bioorganic and Medicinal Chemistry Letters, Apr. 25, 2015, vol. 25, pp. 2720-2725.
Sharma et al., Cell line-based platforms to evaluate the therapeutic efficacy of candidate anticancer agents Nature Reviews Cancer Apr. 2010, vol. 10, 241-253.
Simone et al., Oncology: Introduction, Cecil Textbook of Medicine, 20th Edition, 1996 vol. 1, pp. 1004-1010.
Stewart, Novel therapeutics in multiple myeloma Hematology, 2012, 17(S1), s105-s108.
Uckelmann et al: Therapeutic targeting of preleukemia cells in a mouse model of NPMI1 mutant acute myeloid leukemia; Science 367, 2020, 586-590.
Vardiman et al., The World Health Organization (WHO) classification of the myeloid neoplasms Blood (2002), 100(7), 2292-2302.

(56) References Cited

OTHER PUBLICATIONS

Xu et al: Design of the First-in-Class, Highly Potent Irreversible Inhibitor Targeting the Menin-MLL Protein-Protein Interaction; Angew. Chem. Int. Ed. 2018, 57, 1601-1605.
Xu et al: Discovery of M-808 as a Highly Potent, Covalent, Small-Molecule Inhibitor of the Menin-MLL Interaction with Strong in Vivo Antitumor Activity; J. Med. Chem. 2020, 63, 4997-5010.
Yoo et al., New drugs in prostate cancer, Prostate Int, 2016, 4, 37-42.

PIPERIDINES AS COVALENT MENIN INHIBITORS

BACKGROUND OF THE INVENTION

Field of the Invention

The present disclosure provides compounds as menin inhibitors and therapeutic methods of treating conditions and diseases wherein inhibition of menin provides a benefit.

Background Art

Mixed-lineage leukemia (MLL) is a proto-oncogene that was originally discovered at the site of chromosomal translocations in human leukemias. Due to chromosomal translocations, MLL is fused with more than 40 different partner proteins to yield a diverse collection of chimeric fusion proteins. The MLL protein is a histone methyltransferase that covalently modifies chromatin and is mutated in certain subsets of acute leukemia. Many of the fusion partners constitutively activate novel transcriptional effector properties of MLL that often correlate with its oncogenic potential in animal models of acute leukemia. MLL normally associates with a group of highly conserved cofactors to form a macromolecular complex that includes menin, a product of the MEN1 tumor suppressor gene. The MEN1 gene is mutated in heritable and sporadic endocrine tumors.

Menin is in involved in a diverse network of protein-protein interactions. Cierpicki and Grembecka, *Future Med. Chem.* 6:447-462 (2014). Overexpression of menin leads to inhibition of Ras-transformed cells. Menin interacts with the transcription factors JunD and NF-κB and represses their activation of gene transcription. Studies on these interacting proteins suggest that menin exerts its effects predominantly through inhibitory effects on transcription. But an alternative possibility is that menin mediates its effects through transcriptional activation of target genes. Additionally, menin interacts with RPA2, a component of a single-stranded DNA-binding protein involved in DNA repair and replication. Menin also interacts with FANCD2, a nuclear protein that plays a critical role in maintaining genome stability with breast cancer 1 gene (Brea1) product.

The mechanisms by which menin, which does not have significant homology with other proteins, functions as a tumor suppressor are not completely known. Menin plays a role in regulating cellular proliferation because Men1 knockout mice show increased proliferation in neuroendocrine tissues, down-modulation of menin in epithelial cells increases proliferation, and Men1 knockout fibroblasts proliferate more rapidly than wild-type cells as assayed by tritiated thymidine incorporation. MEN1 cells also have increased sensitivity to DNA-damaging agents. Menin interacts with promoters of HOX genes.

Certain oncogenic MLL fusion proteins stably associate with menin through a high-affinity interaction that is required for the initiation of MLL-mediated leukemogenesis. Menin is essential for maintenance of MLL-associated but no other oncogene induced myeloid transformation. Acute genetic ablation of menin reverses Hox gene expression mediated by MLL-menin promoter-associated complexes, and specifically eliminates the differentiation arrest and oncogenic properties of MLL-transformed leukemic blasts.

MLL fusion proteins, a consequence of acquired genetic aberrations, transform hematopoietic cells through two alternate mechanisms, by either constitutive transcriptional effector activity or inducing forced MLL dimerization and oligomerization. Both mechanisms result in the inappropriate expression of a subset of HOX genes, particularly HOXA9, whose consistent expression is a characteristic feature of human MLL leukemias.

Menin interacts with transcription activators, e.g., sc-Myb, MLL1, SMAD 1,3,5, Pem, Runx2, Hlbx9, ER, PPARγ, vitamin D receptor, transcription repressors, e.g., JunD, Sin3A, HDAC, EZH2, PRMT5, NFκB, Sirt1, CHES1, cell signaling proteins, e.g., AKT, SOS1/GEF, β-catenin, SMAD 1,3,5, NFκB, and other proteins, e.g., cell cycle: RPA2, ASK; DNA repair: FANCD2; cell structure: GFAP, vimenten, NMMHCIIA, IQGAP1; Others: HSP70, CHIP, ("menin-interacting proteins") involved in regulating gene transcription and cell signaling. Matkar, *Trends in Biochemical Sciences* 38: 394-402 (2013). Targeting menin interactions, e.g., menin-MLL interaction, with small molecules represents an attractive strategy to develop new anticancer agents. See, e.g., Cierpicki and Grembecka, *Future Med. Chem.* 6:447-462 (2014); He et al., *J. Med. Chem.* 57:1543-1556 (2014); and Borkin et al., *Cancer Cell* 27:589-602 (2015).

Small molecules that disrupt the interaction of MLL and menin are disclosed in U.S. Pat. Nos. 9,212,180 and 9,216,993; and U.S. Patent Application Publication Nos. 2011/0065690; 2014/0275070; 2016/0045504; and 2016/0046647. Peptides that disrupt the interaction of MLL and menin are disclosed in U.S. Patent Application Publication No. 2009/0298772.

There is an ongoing need for new agents, e.g., small molecules, for treating cancer and other diseases responsive to menin inhibition.

BRIEF SUMMARY OF THE INVENTION

In one aspect, the present disclosure provides piperidines, and related analogs, represented by any one or more of Formulae I-XXI, below, and the pharmaceutically acceptable salts and solvates, e.g., hydrates, thereof, collectively referred to herein as "Compounds of the Disclosure." Compounds of the Disclosure are inhibitors of menin and are thus useful in treating diseases or conditions wherein inhibition of menin provides a therapeutic benefit to a patient.

In another aspect, the present disclosure provides a method of irreversibly inhibiting menin in a patient, comprising administering to the patient an effective amount of a Compound of the Disclosure.

In another aspect, the present disclosure provides methods of treating a condition or disease by administering a therapeutically effective amount of a Compound of the Disclosure to a patient, e.g., a human, in need thereof. The disease or condition is treatable by inhibition menin, for example, a cancer, e.g., leukemia, a chronic autoimmune disorder, an inflammatory condition, a proliferative disorder, sepsis, or a viral infection. Also provided are methods of preventing the proliferation of unwanted proliferating cells, such as cancer, in a subject comprising administering a therapeutically effective amount of a Compound of the Disclosure to a subject at risk of developing a condition characterized by unwanted proliferating cells. In some embodiments, the Compounds of the Disclosure reduce the proliferation of unwanted cells by inducing apoptosis and/or differentiation in those cells.

In another aspect, the present disclosure provides a method of inhibiting menin in an individual, comprising administering to the individual an effective amount of at least one Compound of the Disclosure.

In another aspect, the present disclosure provides a pharmaceutical composition comprising a Compound of the Disclosure and an excipient and/or pharmaceutically acceptable carrier.

In another aspect, the present disclosure provides a composition comprising a Compound of the Disclosure and an excipient and/or pharmaceutically acceptable carrier for use treating diseases or conditions wherein inhibition of menin provides a benefit, e.g., cancer.

In another aspect, the present disclosure provides a composition comprising: (a) a Compound of the Disclosure; (b) a second therapeutically active agent; and (c) optionally an excipient and/or pharmaceutically acceptable carrier.

In another aspect, the present disclosure provides a Compound of the Disclosure for use in treatment of a disease or condition of interest, e.g., cancer.

In another aspect, the present disclosure provides a use of a Compound of the Disclosure for the manufacture of a medicament for treating a disease or condition of interest, e.g., cancer.

In another aspect, the present disclosure provides a kit comprising a Compound of the Disclosure, and, optionally, a packaged composition comprising a second therapeutic agent useful in the treatment of a disease or condition of interest, and a package insert containing directions for use in the treatment of a disease or condition, e.g., cancer.

In another aspect, the present disclosure provides methods of preparing Compounds of the Disclosure.

It is to be understood that both the foregoing summary and the following detailed description are exemplary and explanatory only, and are not restrictive of the invention as claimed.

DETAILED DESCRIPTION OF DRAWINGS

Figure 4:
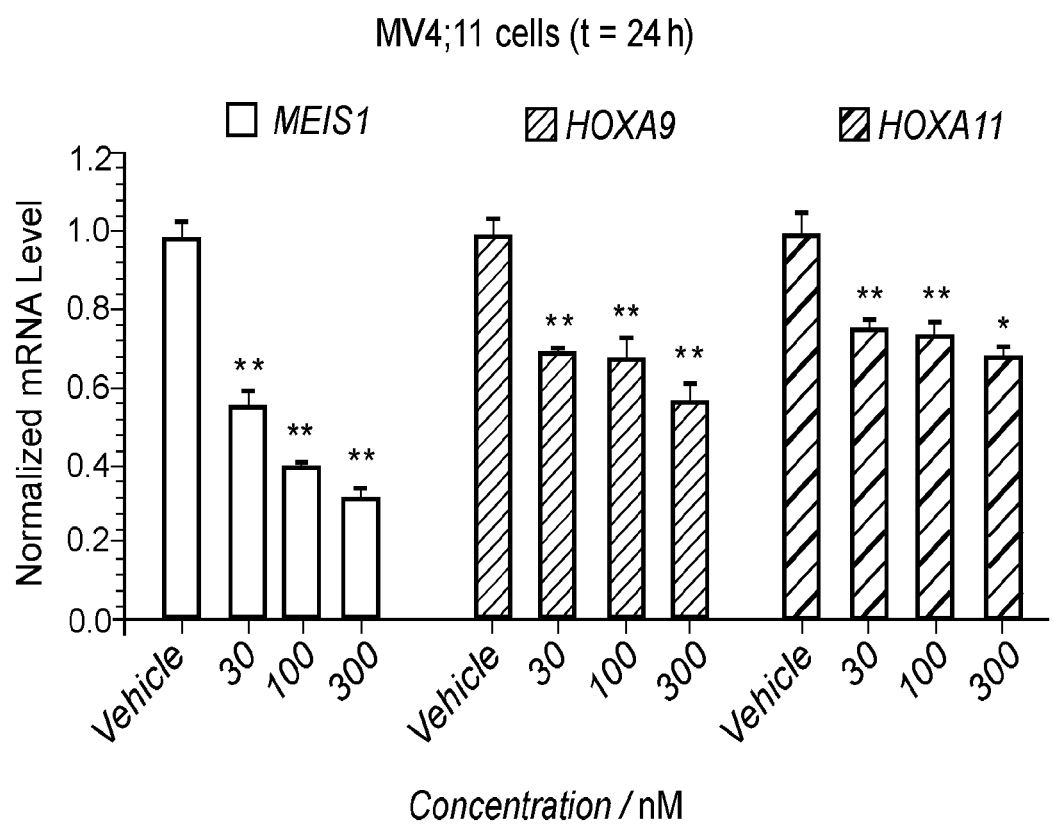

FIG. 4 is a bar graph showing that Cpd. No. 57 suppresses MEIS1 and HOXA gene expression in MV4;11 cell lines. Cells were treated with different concentrations of Cpd. No. 57 for 24 h. mRNA levels of MEIS1, HOXA9 and HOXA11 were determined by RT-PCR. *($p<0.05$), **($p<0.01$).

Figure 5:
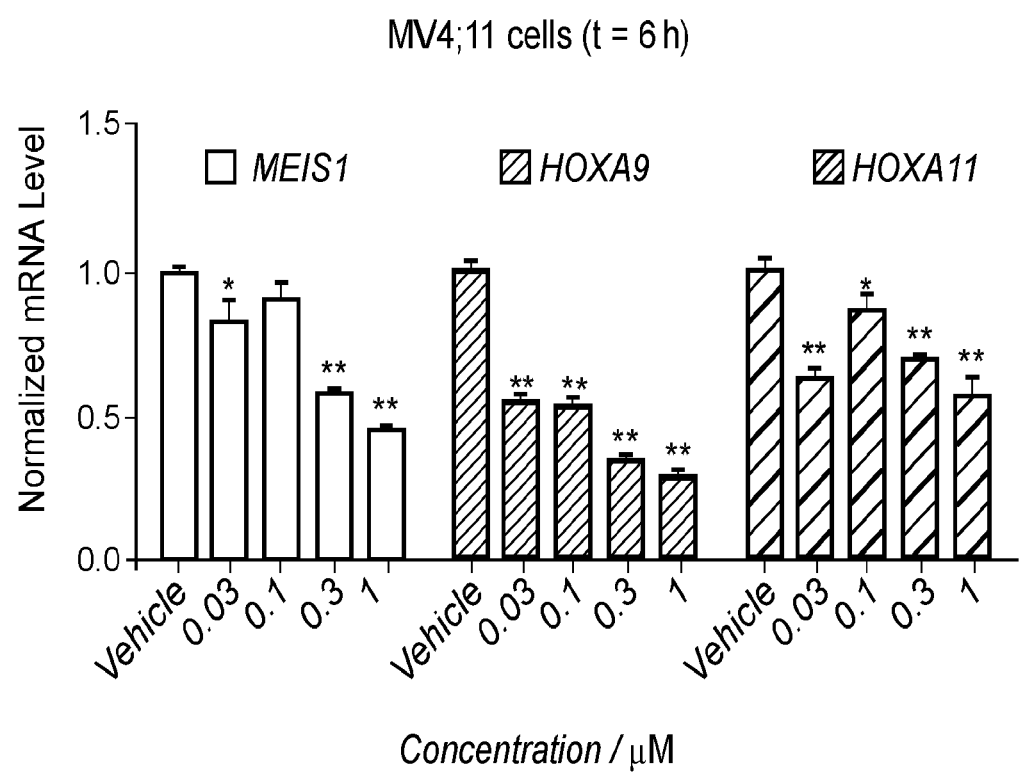

FIG. 5 is a bar graph showing that Cpd. No. 57 suppresses MEIS1 and HOXA gene expression in MV4;11 cell lines. Cells were treated with different concentrations of Cpd. No. 57 for 6 h. mRNA levels of MEIS1, HOXA9 and HOXA11 were determined by RT-PCR. *($p<0.05$), **($p<0.01$).

Figure 6:
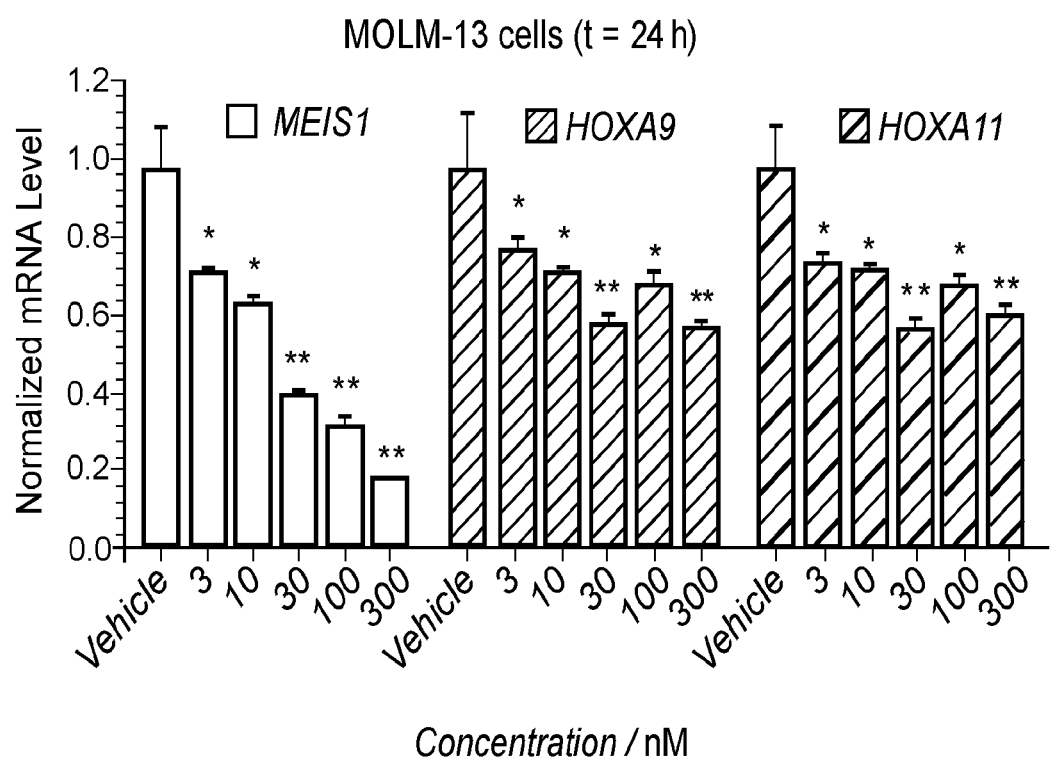

FIG. 6 is a bar graph showing that Cpd. No. 57 suppresses MEIS1 and HOXA gene expression in MOLM13 cell lines. Cells were treated with different concentrations of Cpd. No. 57 for 24 h. mRNA levels of MEIS1, HOXA9 and HOXA11 were determined by RT-PCR. *($p<0.05$), **($p<0.01$).

DETAILED DESCRIPTION OF THE INVENTION

Compounds of the Disclosure are menin inhibitors. In some embodiments, Compounds of the Disclosure covalently bind to and inhibit the function of menin.

In one embodiment, Compounds of the Disclosure are compounds represented by Formula I:

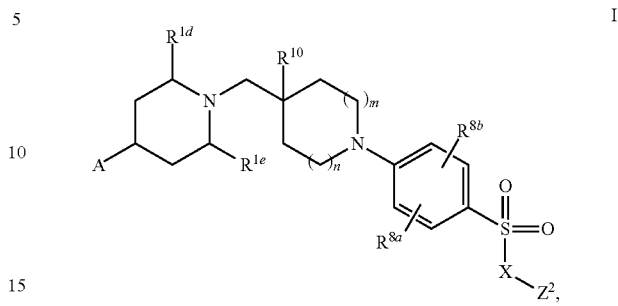

and the pharmaceutically acceptable salts and solvates thereof, wherein:

A is selected from the group consisting of:

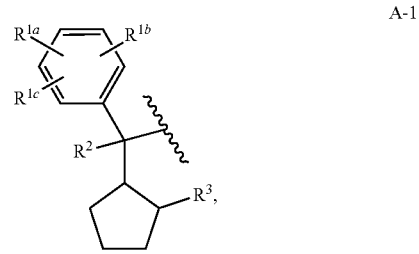

A-1

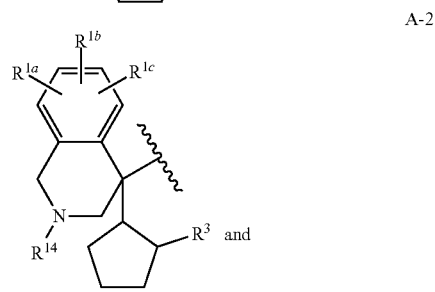

A-2

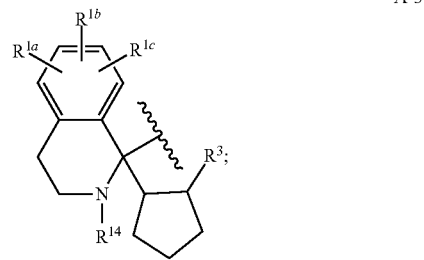

A-3

$R^{1a}$, $R^{1b}$, and $R^{1c}$ are each independently selected from the group consisting of hydrogen, halo, cyano, hydroxy, amino, $C_{1-4}$ alkyl, $C_{1-4}$ haloalkyl, and $C_{1-4}$ alkoxy;

$R^{1d}$ and $R^{1e}$ are independently selected from the group consisting of hydrogen and $C_{1-4}$ alkyl;

$R^2$ is selected from the group consisting of hydroxy, amino, cyano, and —$CH_2R^4$;

$R^3$ is selected from the group consisting of hydrogen, —OC(=O)$NR^{11a}R^{11b}$, —NHC(=O)$R^5$, and —$NHZ^1$;

$R^4$ is selected from the group consisting of amino, optionally substituted aryl, and optionally substituted heteroaryl;

$R^5$ is selected from the group consisting of —$NR^{12a}R^{12b}$, $C_{1-4}$ alkoxy, and $C_{1-4}$ alkyl;

X is selected from the group consisting of:

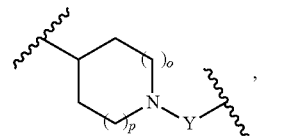
X-1

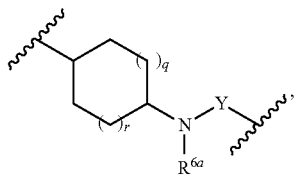
X-2

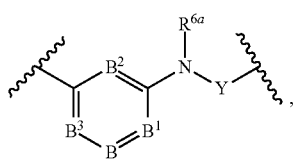
X-3

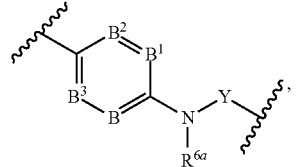
X-4

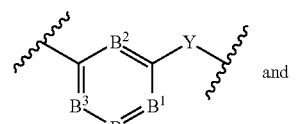
X-5 and

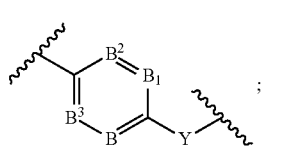
X-6 wherein Y is attached to $Z^2$; or

X is absent;

Y is selected from the group consisting of —C(=O)— and —S(=O)$_2$—;

$R^{6a}$ and $R^{6b}$ are independently selected from the group consisting of hydrogen and $C_{1-4}$ alkyl;

m, n, o, p, q, and r are each independently 0, 1, 2, or 3;

$Z^1$ is selected from the group consisting of —C(=O)$R^7$ and —S(=O)$_2R^7$;

$Z^2$ is selected from the group consisting of —CH=CHR$^{13}$, —C≡CR$^{13}$, —CH$_2$Cl, —CH$_2$Br, —CH$_2$I, alkyl, optionally substituted aryl, optionally substituted heteroaryl, and optionally substituted cycloalkyl, with proviso that $Z^2$ is —CH=CHR$^{13}$, —C≡CR$^{13}$, —CH$_2$Cl, —CH$_2$Br, or —CH$_2$I when $R^3$ is hydrogen, —OC(=O)NR$^{11a}$R$^{11b}$, or —NHC(=O)R$^5$, $R^7$ is selected from the group consisting of —CH=CHR$^{13}$, —C≡CR$^{13}$, —CH$_2$Cl, —CH$_2$Br, and —CH$_2$I;

$R^{8a}$ and $R^{8b}$ are independently selected from the group consisting of hydrogen, halo, cyano, hydroxy, amino, $C_{1-4}$ alkyl, $C_{1-4}$ haloalkyl, and $C_{1-4}$ alkoxy;

$R^{9a}$ is selected from the group consisting of hydrogen, halo, cyano, hydroxy, amino, $C_{1-4}$ alkyl, $C_{1-4}$ haloalkyl, and $C_{1-4}$ alkoxy;

$R^{10}$ is selected from the group consisting of hydrogen, halo, $C_{1-4}$ alkyl, and hydroxy;

$R^{11a}$ and $R^{11b}$ are independently selected from the group consisting of hydrogen and $C_{1-4}$ alkyl; or $R^{11a}$ and $R^{11b}$ taken together with the nitrogen atom to which they are attached form a 4- to 7-membered heterocyclo; and $R^{12a}$ and $R^{12b}$ are independently selected from the group consisting of hydrogen and $C_{1-4}$ alkyl; or $R^{12a}$ and $R^{12b}$ taken together with the nitrogen atom to which they are attached form a 4- to 7-membered heterocyclo;

$R^{13}$ is selected from the group consisting of hydrogen, $C_{1-4}$ alkyl, and (amino)alkyl;

$R^{14}$ is selected from the group consisting of hydrogen and $C_{1-4}$ alkyl; and B, $B^1$, $B^2$, and $B^3$ are each independently selected from the group consisting of =CR$^{9a}$— and =N—, with proviso that at least one of B, $B^1$, $B^2$, and $B^3$ is =CR$^{9a}$—.

In another embodiment, Compounds of the Disclosure are compounds represented by a compound having Formula I, and the pharmaceutically acceptable salts and solvates thereof, wherein $R^{1d}$ and $R^{1e}$ are hydrogen, and $Z^1$ is —C(=O)$R^7$.

In another embodiment, Compounds of the Disclosure are compounds represented by Formula I, and the pharmaceutically acceptable salts and solvates thereof, with the provisos that:

(1) when X is selected from the group consisting of X-1, X-2, X-3, X-4, X-5, and X-6; then $Z^2$ is selected from the group consisting of —CH=CHR$^{13}$, —C≡CR$^{13}$, —CH$_2$Cl, —CH$_2$Br, and —CH$_2$I; and $R^3$ is selected from the group consisting of hydrogen, —OC(=O)NR$^{11a}$R$^{11b}$, and —NHC(=O)R$^5$;

(2) when X is absent and $R^3$ is selected from the group consisting of hydrogen, —OC(=O)NR$^{11a}$R$^{11b}$, and —NHC(=O)R$^5$, then $Z^2$ is selected from the group consisting of —CH=CHR$^{13}$ and —C≡CR$^{13}$; and (3) when X is absent and $R^3$ is —NHZ$^1$, then $Z^2$ is selected from the group consisting of alkyl, optionally substituted aryl, optionally substituted heteroaryl, and optionally substituted cycloalkyl.

In another embodiment, Compounds of the Disclosure are compounds represented by a compound having Formula I, and the pharmaceutically acceptable salts and solvates thereof, wherein:

X is selected from the group consisting of X-1, X-2, X-3, X-4, X-5, and X-6;

$Z^2$ is selected from the group consisting of —CH=CHR$^{13}$, —C≡CR$^{13}$, —CH$_2$Cl, —CH$_2$Br, —CH$_2$I; and $R^3$ is selected from the group consisting of hydrogen, —OC(=O)NR$^{11a}$R$^{11b}$, and —NHC(=O)R$^5$.

In another embodiment, Compounds of the Disclosure are compounds represented by Formula I, and the pharmaceutically acceptable salts and solvates thereof, wherein:

X is absent;

$Z^2$ is selected from the group consisting of alkyl, optionally substituted aryl, optionally substituted heteroaryl, and optionally substituted cycloalkyl; and $R^3$ is —$NHZ^1$.

In another embodiment, Compounds of the Disclosure are compounds represented by Formula I, and the pharmaceutically acceptable salts and solvates thereof, wherein:

X is absent;

$Z^2$ is selected from the group consisting of —CH=$CHR^{13}$ and —C≡$CR^{13}$; and $R^3$ is selected from the group consisting of hydrogen, —OC(=O)$NR^{11a}R^{11b}$, and —NHC(=O)$R^5$.

In another embodiment Compounds of the Disclosure are compounds represented by Formula I, and the pharmaceutically acceptable salts and solvates thereof, wherein A is A-1, e.g., Compounds of the Disclosure are compounds represented by Formula I-A-I:

I-A-I

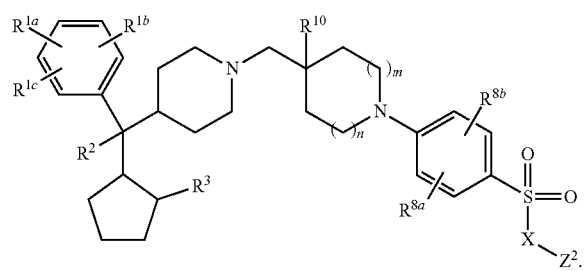

In another embodiment Compounds of the Disclosure are compounds represented by Formula I, and the pharmaceutically acceptable salts and solvates thereof, wherein A is A-2, e.g., Compounds of the Disclosure are compounds represented by Formula I-A-II:

I-A-II

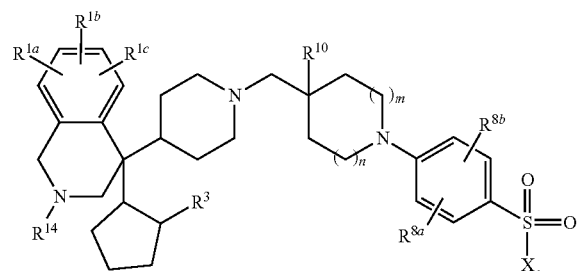

In another embodiment Compounds of the Disclosure are compounds represented by Formula I, and the pharmaceutically acceptable salts and solvates thereof, wherein A is A-3, e.g., Compounds of the Disclosure are compounds represented by Formula I-A-III:

I-A-III

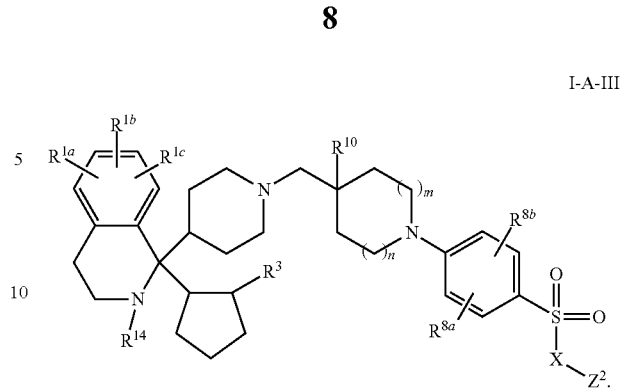

In another embodiment, Compounds of the Disclosure are compounds represented by any one or more of Formulae II-IX:

Formula II

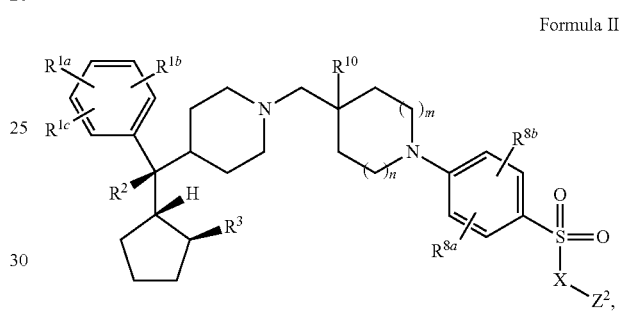

Formula III

Formula IV

Formula V

Formula VI

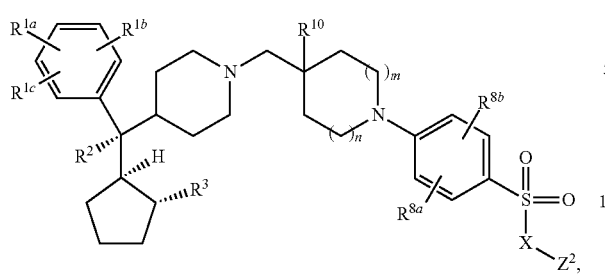

I-A-Ia

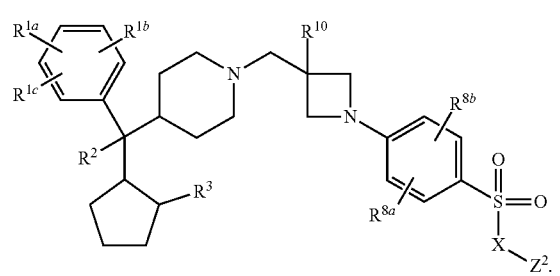

In another embodiment, Compounds of the Disclosure are compounds represented by any one or more of Formulae I-IX, and the pharmaceutically acceptable salts and solvates thereof, wherein m and n are 1, e.g., Compounds of the Disclosure are compounds represented by a compound having Formula I-A-Ib:

Formula VII

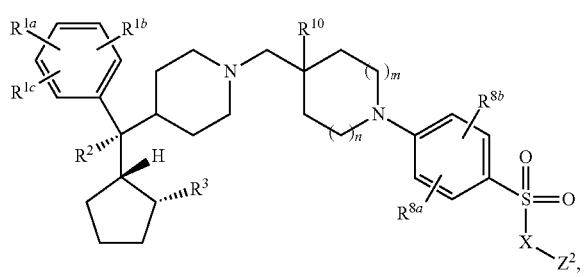

I-A-Ib

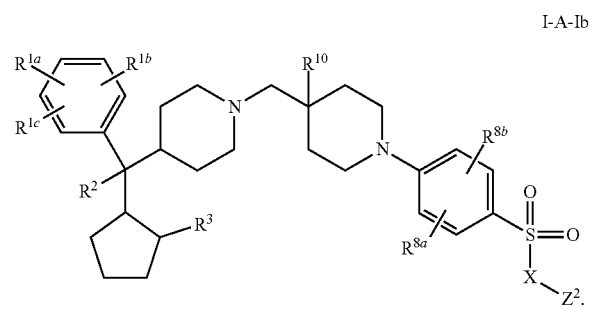

Formula VIII

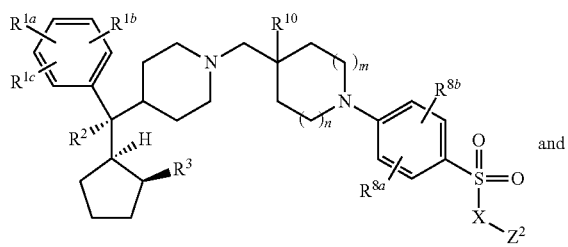
and

In another embodiment, Compounds of the Disclosure are compounds represented by any one or more of Formulae I-IX, and the pharmaceutically acceptable salts and solvates thereof, wherein m is 1 and n is 0, e.g., Compounds of the Disclosure are compounds represented by a compound having Formula I-A-Ic:

Formula IX

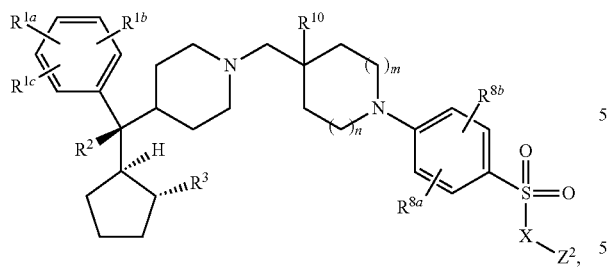

I-A-Ic

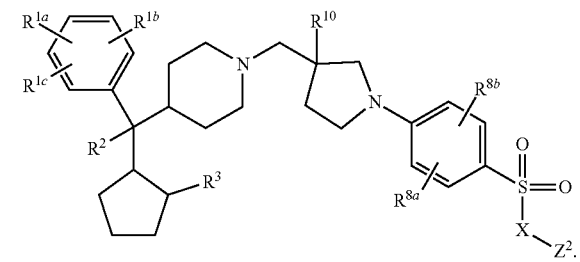

and the pharmaceutically acceptable salts and solvates thereof, wherein $R^{1a}$, $R^{1b}$, $R^{1c}$, $R^2$, $R^3$, $R^{8a}$, $R^{8b}$, $R^{10}$, X, $Z^2$, m, and n are as defined in connection with Formula I.

In another embodiment, Compounds of the Disclosure are compounds represented by any one or more of Formulae I-IX, and the pharmaceutically acceptable salts and solvates thereof, wherein m and n are 0, e.g., Compounds of the Disclosure are compounds represented by a compound having Formula I-A-Ia:

In another embodiment, Compounds of the Disclosure are compounds represented by any one or more of Formulae I-IX, and the pharmaceutically acceptable salts and solvates thereof, wherein $R^{8a}$ and $R^{8b}$ are hydrogen.

In another embodiment, Compounds of the Disclosure are compounds represented by any one or more of Formulae I-IX, and the pharmaceutically acceptable salts and solvates thereof, wherein $R^{1c}$ is hydrogen.

In another embodiment, Compounds of the Disclosure are compounds represented by any one or more of Formulae I-IX, and the pharmaceutically acceptable salts and solvates thereof, wherein B, $B^1$, $B^2$, and $B^3$ are =$CR^{9a}$—.

In another embodiment, Compounds of the Disclosure are compounds represented by any one or more of Formulae I-IX, and the pharmaceutically acceptable salts and solvates thereof, wherein B is =N—, and $B^1$, $B^2$, and $B^3$ are =$CR^{9a}$—.

In another embodiment, Compounds of the Disclosure are compounds represented by any one or more of Formulae I-IX, and the pharmaceutically acceptable salts and solvates thereof, wherein $B^1$ is =N—, and B, $B^2$, and $B^3$ are =$CR^{9a}$—.

In another embodiment, Compounds of the Disclosure are compounds represented by any one or more of Formulae I-IX, and the pharmaceutically acceptable salts and solvates thereof, wherein $B^2$ is =N—, and B, $B^1$, and $B^3$ are =$CR^{9a}$—.

In another embodiment, Compounds of the Disclosure are compounds represented by any one or more of Formulae I-IX, and the pharmaceutically acceptable salts and solvates thereof, wherein $B^3$ is =N—, and B, $B^1$, and $B^2$ are =$CR^{9a}$—.

In another embodiment, Compounds of the Disclosure are compounds represented by Formula X:

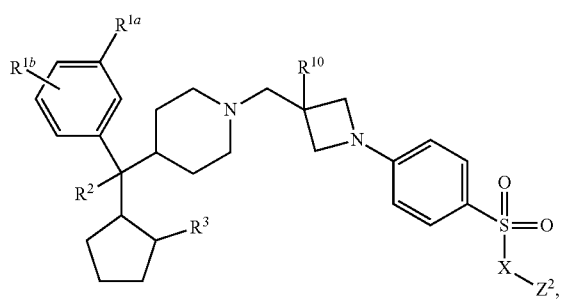

X and the pharmaceutically acceptable salts and solvates thereof, wherein:

X is selected from the group consisting of X-1, X-2, X-3, X-4, X-5, and X-6; or

X is absent;

$Z^2$ is selected from the group consisting of —CH=$CHR^{13}$ and —C≡$CR^{13}$;

$R^3$ is selected from the group consisting of —OC(=O)$NR^{11a}R^{11b}$, and —NHC(=O)$R^5$; and $R^{1a}$, $R^{1b}$, $R^2$, and $R^{10}$ are as defined in connection with Formula I.

In another embodiment, Compounds of the Disclosure are compounds represented by Formula XI:

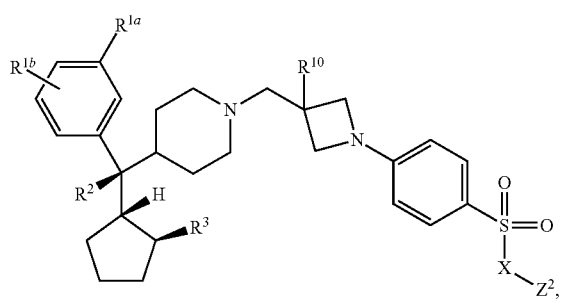

XI and the pharmaceutically acceptable salts and solvates thereof, wherein $R^{1a}$, $R^{1b}$, $R^2$, $R^3$, $R^{10}$, X, and $Z^2$ are as defined in connection with Formula X.

In another embodiment, Compounds of the Disclosure are compounds represented by Formula X or Formula XI, and the pharmaceutically acceptable salts and solvates thereof, wherein X is absent.

In another embodiment, Compounds of the Disclosure are compounds represented by any one or more of Formulae I-XI, and the pharmaceutically acceptable salts and solvates thereof, wherein X is X-1. In another embodiment, o and p are 0. In another embodiment, o and p are 1. In another embodiment, Y is —C(=O)—. In another embodiment, Y is —S(=O)$_2$—.

In another embodiment, Compounds of the Disclosure are compounds represented by any one or more of Formulae I-XI, and the pharmaceutically acceptable salts and solvates thereof, wherein X is X-2. In another embodiment, q and r are 0. In another embodiment, q and r are 1. In another embodiment, Y is —C(=O)—. In another embodiment, Y is —S(=O)$_2$—.

In another embodiment, Compounds of the Disclosure are compounds represented by any one or more of Formulae I-XI, and the pharmaceutically acceptable salts and solvates thereof, wherein X is X-3. In another embodiment, B, $B^1$, $B^2$, and $B^3$ are =$CR^{9a}$—. In another embodiment, $R^{9a}$ is hydrogen. In another embodiment, Y is —C(=O)—. In another embodiment, Y is —S(=O)$_2$—.

In another embodiment, Compounds of the Disclosure are compounds represented by any one or more of Formulae I-XI, and the pharmaceutically acceptable salts and solvates thereof, wherein X is X-4. In another embodiment, B, $B^1$, $B^2$, and $B^3$ are =$CR^{9a}$—. In another embodiment, $R^{9a}$ is hydrogen. In another embodiment, Y is —C(=O)—. In another embodiment, Y is —S(=O)$_2$—.

In another embodiment, Compounds of the Disclosure are compounds represented by any one or more of Formulae I-XI, and the pharmaceutically acceptable salts and solvates thereof, wherein X is X-5. In another embodiment, B, $B^1$, $B^2$, and $B^3$ are =$CR^{9a}$—. In another embodiment, $R^{9a}$ is hydrogen. In another embodiment, Y is —C(=O)—. In another embodiment, Y is —S(=O)$_2$—.

In another embodiment, Compounds of the Disclosure are compounds represented by any one or more of Formulae I-XI, and the pharmaceutically acceptable salts and solvates thereof, wherein X is X-6. In another embodiment, B, $B^1$, $B^2$, and $B^3$ are =$CR^{9a}$—. In another embodiment, $R^{9a}$ is hydrogen. In another embodiment, Y is —C(=O)—. In another embodiment, Y is —S(=O)$_2$—.

In another embodiment, Compounds of the Disclosure are compounds represented by any one or more of Formulae I-XI, and the pharmaceutically acceptable salts and solvates thereof, wherein $R^3$ is hydrogen.

In another embodiment, Compounds of the Disclosure are compounds represented by any one or more of Formulae I-XI, and the pharmaceutically acceptable salts and solvates thereof, wherein $R^3$ is —OC(=O)$NR^{11a}R^{11b}$. In another embodiment, $R^{11a}$ is —$CH_3$ and $R^{11b}$ is hydrogen.

In another embodiment, Compounds of the Disclosure are compounds represented by any one or more of Formulae I-XI, and the pharmaceutically acceptable salts and solvates thereof, wherein $R^3$ is —NHC(=O)$R^5$. In another embodiment, $R^5$ is selected from the group consisting of —$OCH_3$ and —$CH_2CH_3$.

In another embodiment, Compounds of the Disclosure are compounds represented by any one or more of Formulae I-XI, and the pharmaceutically acceptable salts and solvates thereof, wherein $Z^2$ is selected from the group consisting of —CH=CH$_2$ and —C≡CH.

In another embodiment, Compounds of the Disclosure are compounds represented by Formula XII:

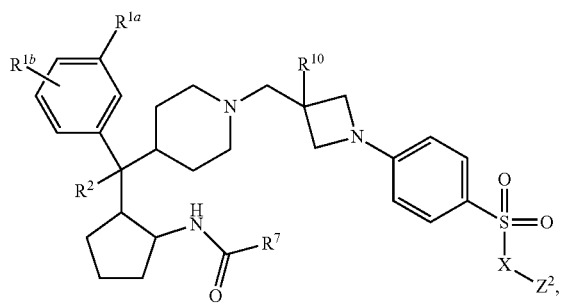

XII and the pharmaceutically acceptable salts and solvates thereof, wherein:

$Z^2$ is selected from the group consisting of alkyl, optionally substituted aryl, optionally substituted heteroaryl, and optionally substituted cycloalkyl; and $R^{1a}$, $R^{1b}$, $R^2$, $R^7$, and $R^{10}$ are as defined in connection with Formula I.

In another embodiment, Compounds of the Disclosure are compounds represented by Formula XIII:

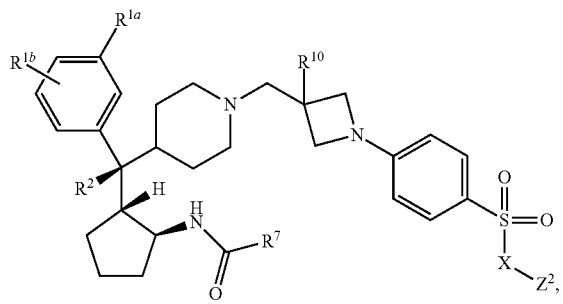

XIII and the pharmaceutically acceptable salts and solvates thereof, wherein $R^{1a}$, $R^{1b}$, $R^2$, $R^7$, and $R^{10}$ are as defined in connection with Formula XII.

In another embodiment, Compounds of the Disclosure are compounds represented by Formula XII or XIII, and the pharmaceutically acceptable salts and solvates thereof, wherein $R^7$ is —CH=CH$_2$.

In another embodiment, Compounds of the Disclosure are compounds represented by Formula XIV:

XIV

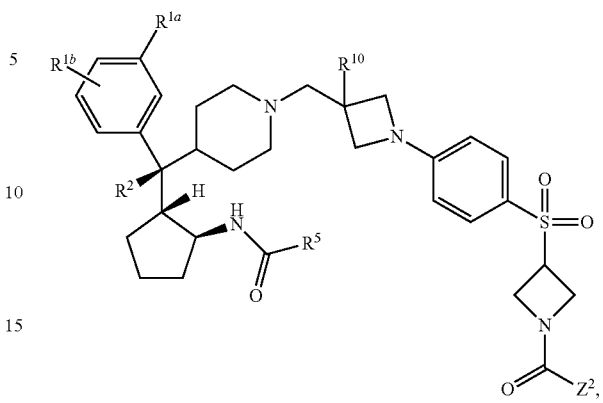

and the pharmaceutically acceptable salts and solvates thereof, wherein $R^{1a}$, $R^{1b}$, $R^2$, $R^5$, $R^{10}$, and $Z^2$ are as defined in connection with Formula I.

In another embodiment, Compounds of the Disclosure are compounds represented by Formula XV:

XV

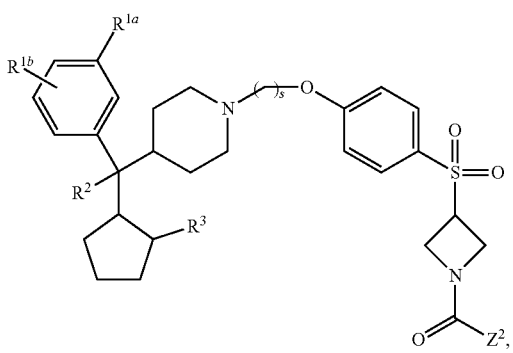

and the pharmaceutically acceptable salts and solvates thereof, wherein $R^3$ is selected from the group consisting of —OC(=O)NR$^{11a}$R$^{1b}$ and —NHC(=O)R; $R^{11a}$, $R^{11b}$, $R^2$, $R^5$, $R^{11a}$, $R^{11b}$ and $Z^2$ are as defined in connection with Formula I; and s is 2, 3, 4, or 5.

In another embodiment, Compounds of the Disclosure are compounds represented by Formula XVI:

XVI

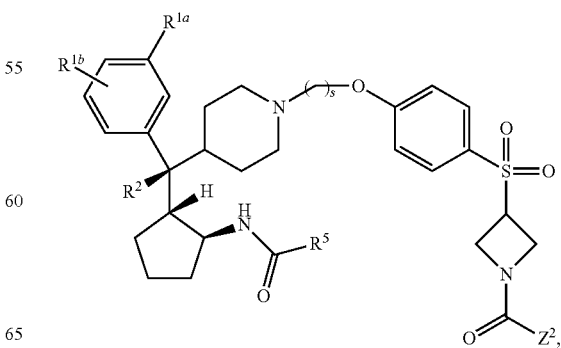

and the pharmaceutically acceptable salts and solvates thereof, wherein $R^{1a}$, $R^{1b}$, $R^2$, $R^5$, $Z^2$, and s are as defined in connection with Formula XV.

In another embodiment, Compounds of the Disclosure are compounds represented by Formula XVII:

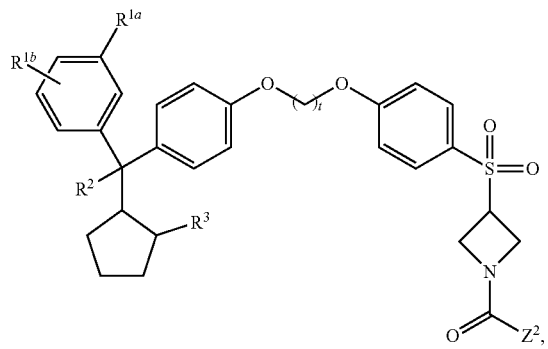

XVII and the pharmaceutically acceptable salts and solvates thereof, wherein: $R^3$ is selected from the group consisting of —OC(=O)NR$^{11a}$R$^{11b}$ and —NHC(=O)R$^5$; $R^{1a}$, $R^{1b}$, $R^2$, $R^5$, $R^{11a}$, $R^{11b}$ and $Z^2$ are as defined in connection with Formula I; and t is 2, 3, 4, or 5.

In another embodiment, Compounds of the Disclosure are compounds represented by Formula XVIII:

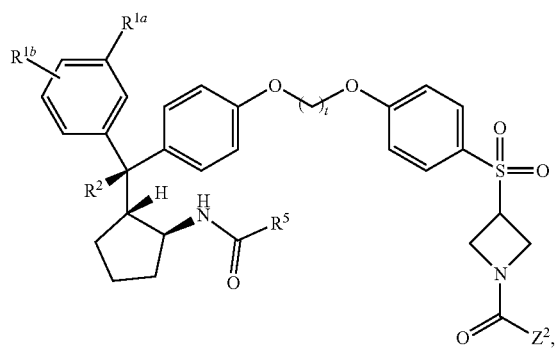

XVIII and the pharmaceutically acceptable salts and solvates thereof, wherein $R^{1a}$, $R^{1b}$, $R^2$, $R^5$, $Z^2$, and t are as defined in connection with Formula XVII.

In another embodiment, Compounds of the Disclosure are compounds represented by Formula XIX:

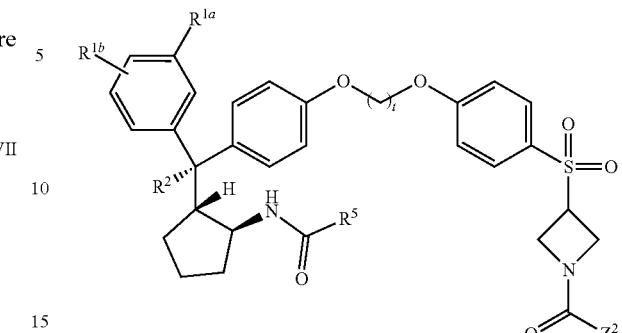

XIX and the pharmaceutically acceptable salts and solvates thereof, wherein $R^{1a}$, $R^{1b}$, $R^2$, $R^5$, and $Z^2$, and t are as defined in connection with Formula XVII.

In another embodiment, Compounds of the Disclosure are compounds represented by Formula XX:

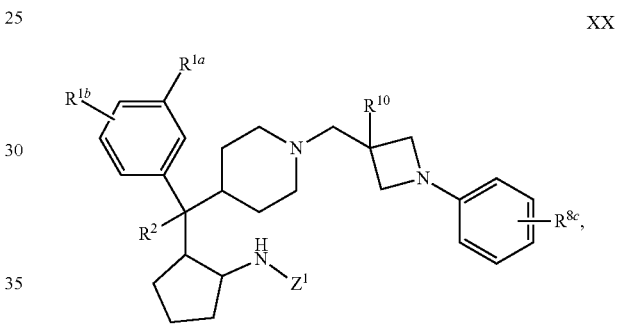

XX and the pharmaceutically acceptable salts and solvates thereof, wherein $R^{1a}$, $R^{1b}$, $R^2$, $R^{10}$, and $Z^1$ are as defined in connection with Formula I, and $R^{8c}$ is selected from the group consisting of hydrogen, halo, cyano, hydroxy, amino, $C_{1-4}$ alkyl, $C_{1-4}$ haloalkyl, and $C_{1-4}$ alkoxy.

In another embodiment, Compounds of the Disclosure are compounds represented by Formula XXI

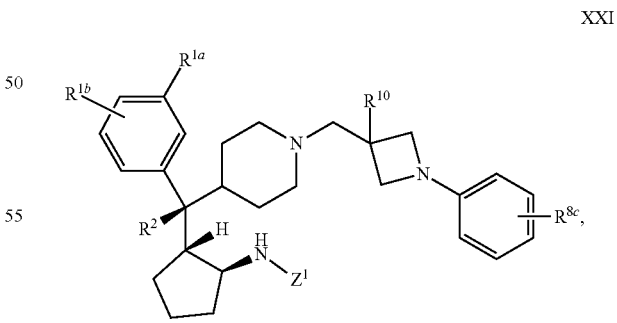

XXI and the pharmaceutically acceptable salts and solvates thereof, wherein $R^{1a}$, $R^{1b}$, $R^2$, $R^{8c}$, $R^{10}$, and $Z^1$ are as defined in connection with Formula XX.

In another embodiment, Compounds of the Disclosure are compounds represented by any one or more of Formulae I-XXI, and the pharmaceutically acceptable salts and solvates thereof, wherein $R^2$ is cyano.

In another embodiment, Compounds of the Disclosure are compounds represented by any one or more of Formulae I-XXI, and the pharmaceutically acceptable salts and solvates thereof, wherein $R^2$ is —$CH_2R^4$ and $R^4$ is optionally substituted heteroaryl. In another embodiment, $R^4$ is selected from the group consisting of:

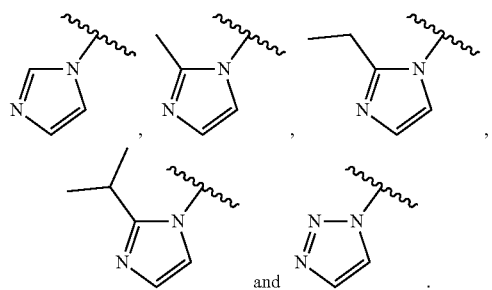

In another embodiment, Compounds of the Disclosure are compounds represented by any one or more of Formulae I-XXI, and the pharmaceutically acceptable salts and solvates thereof, wherein $R^{10}$ is hydrogen.

In another embodiment, Compounds of the Disclosure are compounds represented by any one or more of Formulae I-XXI, and the pharmaceutically acceptable salts and solvates thereof, wherein $R^{10}$ is fluoro.

In another embodiment, Compounds of the Disclosure are compounds represented by any one or more of Formulae I-XXI, and the pharmaceutically acceptable salts and solvates thereof, wherein $R^{1a}$ and $R^{1b}$ are independently selected from the group consisting of hydrogen and halogen.

In another embodiment, Compounds of the Disclosure are compounds represented by any one or more of Formulae I-XI or XIV-XXI, and the pharmaceutically acceptable salts and solvates thereof, wherein $Z^2$ is —CH=$CHR^{13}$, and $R^{13}$ is selected from the group consisting of hydrogen and $C_{1-4}$ alkyl. In another embodiment, $R^{13}$ is selected from the group consisting of hydrogen and methyl.

In another embodiment, Compounds of the Disclosure are compounds represented by any one or more of Formulae I-XI or XIV-XXI, and the pharmaceutically acceptable salts and solvates thereof, wherein $Z^2$ is —CH=$CHR^{13}$, $R^{13}$ is —$CH_2$—$NR^{22c}R^{22d}$; $R^{22c}$ and $R^{22d}$ are each independently selected from the group consisting of hydrogen and $C_{1-4}$ alkyl, or $R^{22c}$ and $R^{22d}$ are taken together to form a 4- to 8-membered optionally substituted heterocyclo.

In another embodiment, Compounds of the Disclosure are compounds represented by any one or more of Formulae I-XI or XIV-XXI, and the pharmaceutically acceptable salts and solvates thereof, wherein $Z^2$ is —CH=$CHR^{13}$, and $R^{13}$ is selected from the group consisting of hydrogen, methyl,

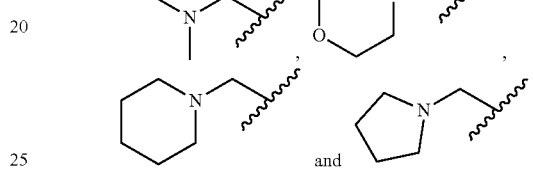

In another embodiment, Compounds of the Disclosure are compounds represented by Formula I selected from any one or more of the compounds of Table 1.

In another embodiment, Compounds of the Disclosure are compounds represented by Formula XV selected from any one or more of the compounds of Table 1A.

In another embodiment, Compounds of the Disclosure are compounds represented by Formula XVII selected from any one or more of the compounds of Table 1B.

In another embodiment, Compounds of the Disclosure are compounds represented by Formula XX selected from any one or more of the compounds of Table 1C

TABLE 1

| Cpd No. | Structure | Name |
|---|---|---|
| 1 | 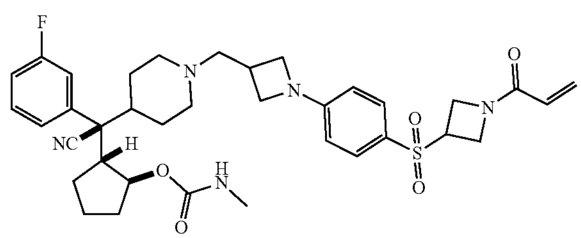 [SMILES: C=CC(=O)N1CC(S(=O)(=O)c2ccc(N3CC(CN4CCC([C@@](C#N)(c5cccc(F)c5)[C@H]5CCC[C@@H]5OC(=O)NC)CC4)C3)cc2)C1] | (1S,2R)-2-((S)-(1-((1-(4-((1-acryloylazetidin-3-yl)sulfonyl)phenyl)azetidin-3-yl)methyl)piperidin-4-yl)(cyano)(3-fluorophenyl)methyl)cyclopentyl methylcarbamate |
| 2 | 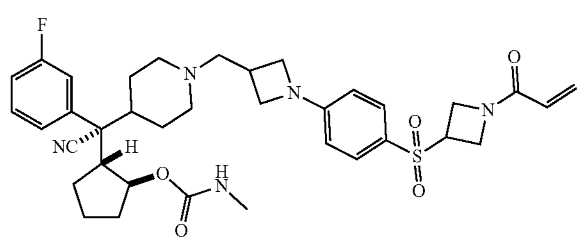 [SMILES: C=CC(=O)N1CC(S(=O)(=O)c2ccc(N3CC(CN4CCC([C@](C#N)(c5cccc(F)c5)[C@H]5CCC[C@@H]5OC(=O)NC)CC4)C3)cc2)C1] | (1S,2R)-2-((R)-(1-((1-(4-((1-acryloylazetidin-3-yl)sulfonyl)phenyl)azetidin-3-yl)methyl)piperidin-4-yl)(cyano)(3-fluorophenyl)methyl)cyclopentyl methylcarbamate |

TABLE 1-continued

| Cpd No. | Structure | Name |
|---|---|---|
| 3 | 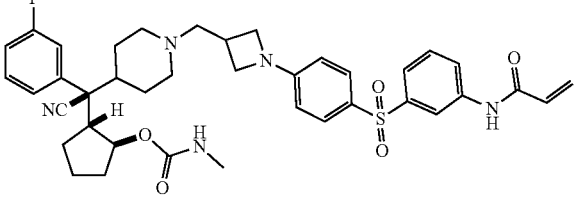 | (1S,2R)-2-((S)-(1-((1-(4-((3-acrylamidophenyl)sulfonyl)phenyl)azetidin-3-yl)methyl)piperidin-4-yl)(cyano)(3-fluorophenyl)methyl)cyclopentyl methylcarbamate |
| 4 | 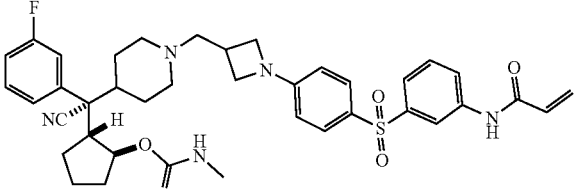 | (1S,2R)-2-((R)-(1-((1-(4-((3-acrylamidophenyl)sulfonyl)phenyl)azetidin-3-yl)methyl)piperidin-4-yl)(cyano)(3-fluorophenyl)methyl)cyclopentyl methylcarbamate |
| 5 | 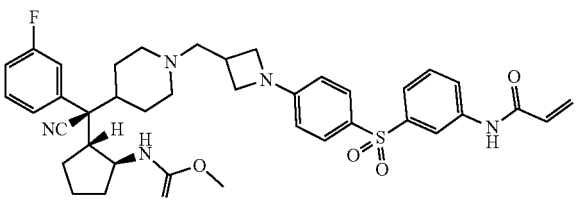 | methyl ((1S,2R)-2-((S)-(1-((1-(4-((3-acrylamidophenyl)sulfonyl)phenyl)azetidin-3-yl)methyl)piperidin-4-yl)(cyano)(3-fluorophenyl)methyl)cyclopentyl)carbamate |
| 6 | 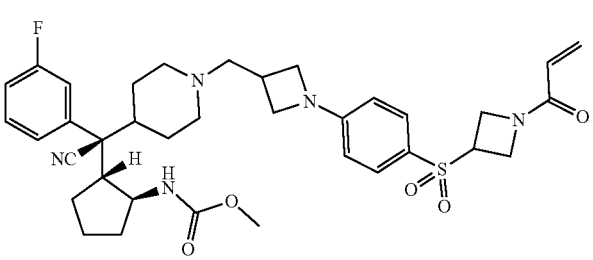 [SMILES: C=CC(=O)N1CC(S(=O)(=O)c2ccc(N3CC(CN4CCC([C@@](C#N)(c5cccc(F)c5)[C@H]5CCC[C@@H]5NC(=O)OC)CC4)C3)cc2)C1] | methyl ((1S,2R)-2-((S)-(1-((1-(4-((1-acryloylazetidin-3-yl)sulfonyl)phenyl)azetidin-3-yl)methyl)piperidin-4-yl)(cyano)(3-fluorophenyl)methyl)cyclopentyl)carbamate |
| 7 | 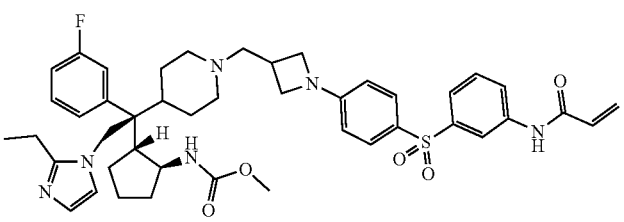 [SMILES: C=CC(=O)Nc1cccc(S(=O)(=O)c2ccc(N3CC(CN4CCC([C@@](Cn5ccnc5CC)(c5cccc(F)c5)[C@H]5CCC[C@@H]5NC(=O)OC)CC4)C3)cc2)c1] | methyl ((1S,2R)-2-((S)-1-(1-((1-(4-((3-acrylamidophenyl)sulfonyl)phenyl)azetidin-3-yl)methyl)piperidin-4-yl)-2-(2-ethyl-1H-imidazol-1-yl)-1-(3-fluorophenyl)ethyl)cyclopentyl)carbamate |
| 8 | 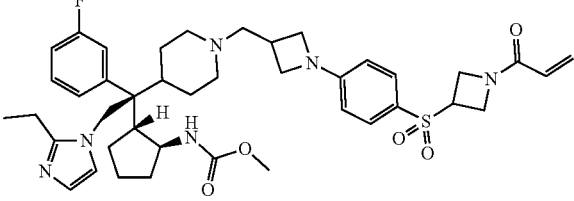 | methyl ((1S,2R)-2-((S)-1-(1-((1-(4-((1-acryloylazetidin-3-yl)sulfonyl)phenyl)azetidin-3-yl)methyl)piperidin-4-yl)-2-(2-ethyl-1H-imidazol-1-yl)-1-(3-fluorophenyl)ethyl)cyclopentyl)carbamate |
| 9 | 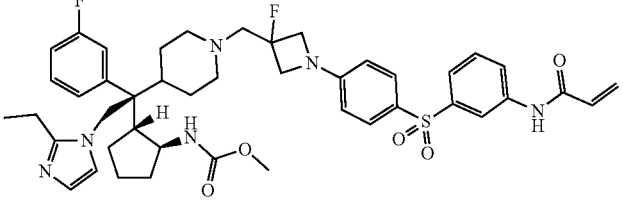 | methyl ((1S,2R)-2-((S)-1-(1-((1-(4-((3-acrylamidophenyl)sulfonyl)phenyl)-3-fluoroazetidin-3-yl)methyl)piperidin-4-yl)-2-(2-ethyl-1H-imidazol-1-yl)-1-(3-fluorophenyl)ethyl)cyclopentyl)carbamate |

TABLE 1-continued

| Cpd No. | Structure | Name |
|---|---|---|
| 10 | 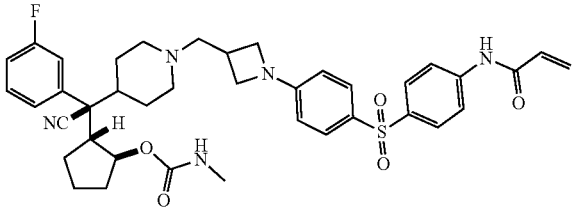 [SMILES: C=CC(=O)Nc1ccc(S(=O)(=O)c2ccc(N3CC(CN4CCC([C@@](C#N)(c5cccc(F)c5)[C@H]5CCC[C@@H]5OC(=O)NC)CC4)C3)cc2)cc1] | (1S,2R)-2-((S)-(1-((1-(4-((4-acrylamidophenyl)sulfonyl)phenyl)azetidin-3-yl)methyl)piperidin-4-yl)(cyano)(3-fluorophenyl)methyl)cyclopentyl methylcarbamate |
| 11 | 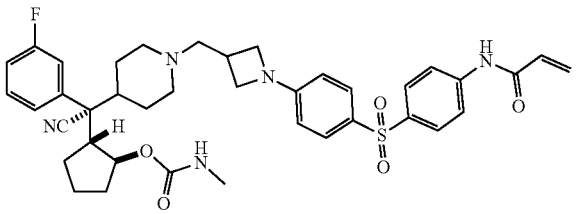 [SMILES: C=CC(=O)Nc1ccc(S(=O)(=O)c2ccc(N3CC(CN4CCC([C@](C#N)(c5cccc(F)c5)[C@H]5CCC[C@@H]5OC(=O)NC)CC4)C3)cc2)cc1] | (1S,2R)-2-((R)-(1-((1-(4-((4-acrylamidophenyl)sulfonyl)phenyl)azetidin-3-yl)methyl)piperidin-4-yl)(cyano)(3-fluorophenyl)methyl)cyclopentyl methylcarbamate |
| 12 | 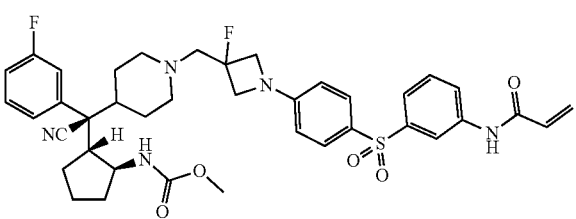 [SMILES: C=CC(=O)Nc1cccc(S(=O)(=O)c2ccc(N3CC(F)(CN4CCC([C@@](C#N)(c5cccc(F)c5)[C@H]5CCC[C@@H]5NC(=O)OC)CC4)C3)cc2)c1] | methyl ((1S,2R)-2-((S)-(1-((1-(4-((3-acrylamidophenyl)sulfonyl)phenyl)-3-fluoroazetidin-3-yl)methyl)piperidin-4-yl)(cyano)(3-fluorophenyl)methyl)cyclopentyl)carbamate |
| 13 | 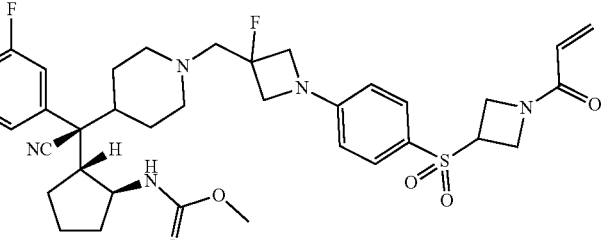 | methyl ((1S,2R)-2-((S)-(1-((1-(4-((1-acryloylazetidin-3-yl)sulfonyl)phenyl)-3-fluoroazetidin-3-yl)methyl)piperidin-4-yl)(cyano)(3-fluorophenyl)methyl)cyclopentyl)carbamate |
| 14 | 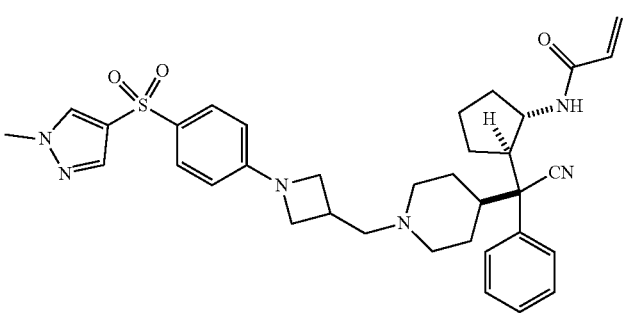 | N-((1S,2R)-2-((S)-cyano(1-((1-(4-((1-methyl-1H-pyrazol-4-yl)sulfonyl)phenyl)azetidin-3-yl)methyl)piperidin-4-yl)(phenyl)methyl)cyclopentyl)acrylamide |
| 15 | 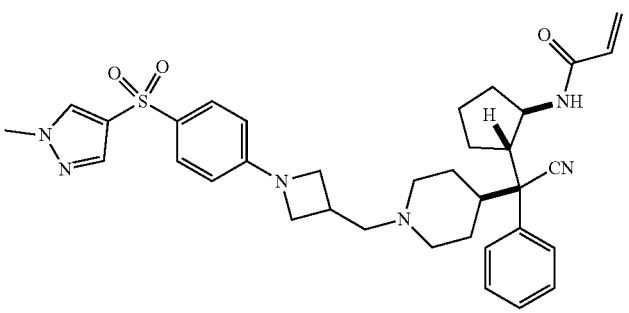 | N-((1R,2S)-2-((S)-cyano(1-((1-(4-((1-methyl-1H-pyrazol-4-yl)sulfonyl)phenyl)azetidin-3-yl)methyl)piperidin-4-yl)(phenyl)methyl)cyclopentyl)acrylamide |

TABLE 1-continued

| Cpd No. | Structure | Name |
|---|---|---|
| 16 | 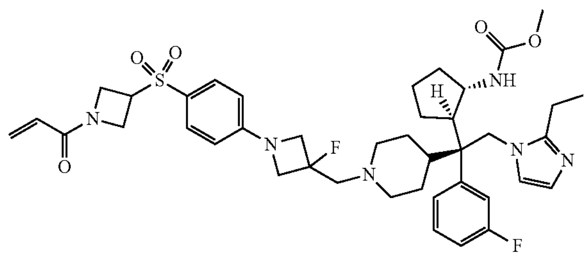 | methyl ((1S,2R)-2-((S)-1-(1-((1-(4-((1-acryloylazetidin-3-yl)sulfonyl)phenyl)-3-fluoroazetidin-3-yl)methyl)piperidin-4-yl)-2-(2-ethyl-1H-imidazol-1-yl)-1-(3-fluorophenyl)ethyl)cyclopentyl)carbamate |
| 17 | 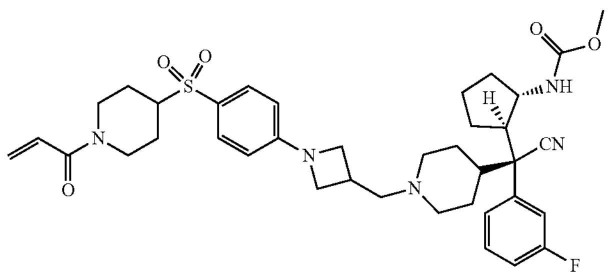 | methyl ((1S,2R)-2-((S)-(1-((1-(4-((1-acryloylpiperidin-4-yl)sulfonyl)phenyl)azetidin-3-yl)methyl)piperidin-4-yl)(cyano)(3-fluorophenyl)methyl)cyclopentyl)carbamate |
| 18 | 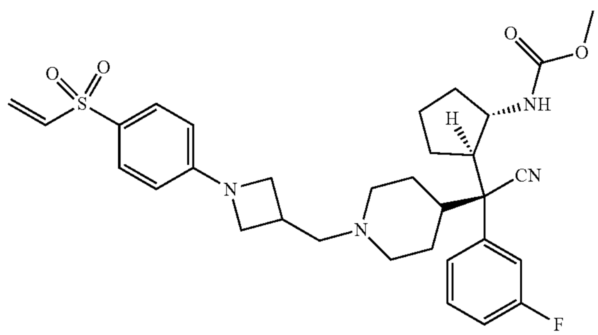 | methyl ((1S,2R)-2-((S)-cyano(3-fluorophenyl)(1-((1-(4-(vinylsulfonyl)phenyl)azetidin-3-yl)methyl)piperidin-4-yl)methyl)cyclopentyl)carbamate |
| 19 | 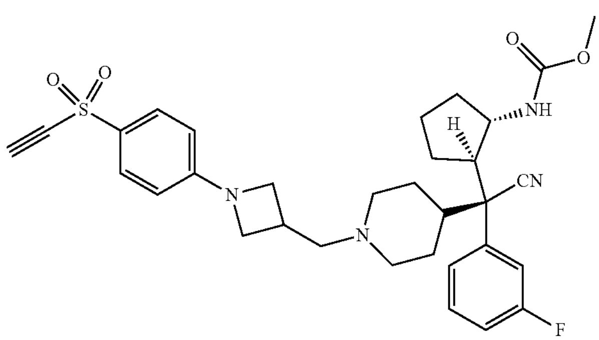 | methyl ((1S,2R)-2-((S)-cyano(1-((1-(4-(ethynylsulfonyl)phenyl)azetidin-3-yl)methyl)piperidin-4-yl)(3-fluorophenyl)methyl)cyclopentyl)carbamate |
| 20 | 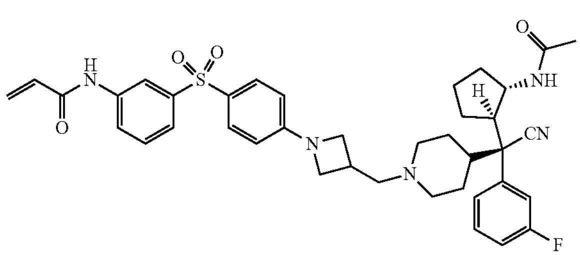 | N-(3-((4-(3-((4-((S)-((1R,2S)-2-acetamidocyclopentyl)(cyano)(3-fluorophenyl)methyl)piperidin-1-yl)methyl)azetidin-1-yl)phenyl)sulfonyl)phenyl)acrylamide |

TABLE 1-continued

| Cpd No. | Structure | Name |
|---|---|---|
| 21 | 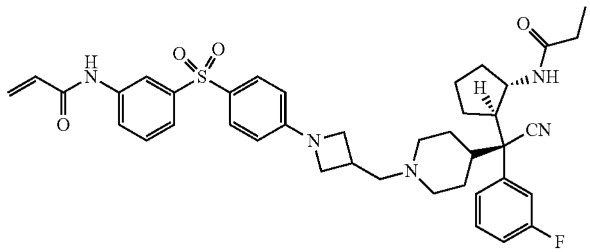 | N-(3-((4-(3-((4-((S)-cyano(3-fluorophenyl)((1R,2S)-2-propionamidocyclopentyl)methyl)piperidin-1-yl)methyl)azetidin-1-yl)phenyl)sulfonyl)phenyl)acrylamide |
| 22 | 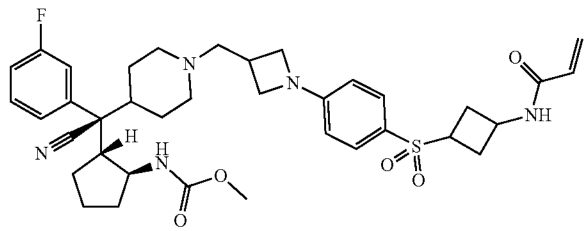 [SMILES: C=CC(=O)NC1CC(S(=O)(=O)c2ccc(N3CC(CN4CCC([C@@](C#N)(c5cccc(F)c5)[C@H]5CCC[C@@H]5NC(=O)OC)CC4)C3)cc2)C1] | methyl ((1S,2R)-2-((S)-(1-((1-(4-((3-acrylamidocyclobutyl)sulfonyl)phenyl)azetidin-3-yl)methyl)piperidin-4-yl)(cyano)(3-fluorophenyl)methyl)cyclopentyl)carbamate |
| 23 | 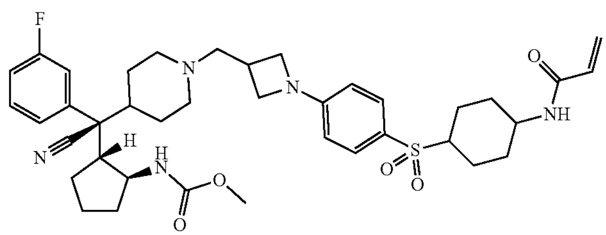 [SMILES: C=CC(=O)NC1CCC(S(=O)(=O)c2ccc(N3CC(CN4CCC([C@@](C#N)(c5cccc(F)c5)[C@H]5CCC[C@@H]5NC(=O)OC)CC4)C3)cc2)CC1] | methyl ((1S,2R)-2-((S)-(1-((1-(4-((4-acrylamidocyclohexyl)sulfonyl)phenyl)azetidin-3-yl)methyl)piperidin-4-yl)(cyano)(3-fluorophenyl)methyl)cyclopentyl)carbamate |
| 24 | 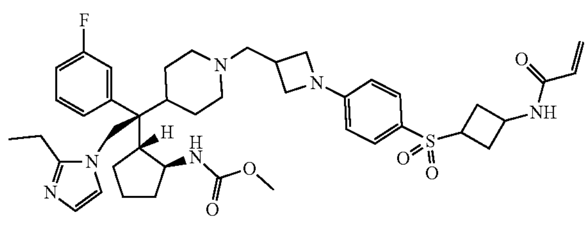 [SMILES: C=CC(=O)NC1CC(S(=O)(=O)c2ccc(N3CC(CN4CCC([C@@](Cn5ccnc5CC)(c5cccc(F)c5)[C@H]5CCC[C@@H]5NC(=O)OC)CC4)C3)cc2)C1] | methyl ((1S,2R)-2-((S)-1-(1-((1-(4-((3-acrylamidocyclobutyl)sulfonyl)phenyl)azetidin-3-yl)methyl)piperidin-4-yl)-2-(2-ethyl-1H-imidazol-1-yl)-1-(3-fluorophenyl)ethyl)cyclopentyl)carbamate |
| 25 | 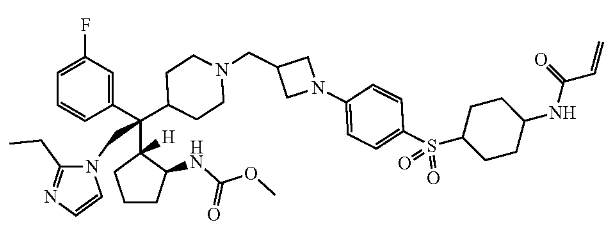 [SMILES: C=CC(=O)NC1CCC(S(=O)(=O)c2ccc(N3CC(CN4CCC([C@@](Cn5ccnc5CC)(c5cccc(F)c5)[C@H]5CCC[C@@H]5NC(=O)OC)CC4)C3)cc2)CC1] | methyl ((1S,2R)-2-((S)-1-(1-((1-(4-((4-acrylamidocyclohexyl)sulfonyl)phenyl)azetidin-3-yl)methyl)piperidin-4-yl)-2-(2-ethyl-1H-imidazol-1-yl)-1-(3-fluorophenyl)ethyl)cyclopentyl)carbamate |
| 26 | 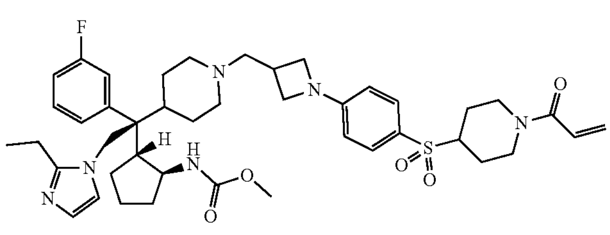 [SMILES: C=CC(=O)N1CCC(S(=O)(=O)c2ccc(N3CC(CN4CCC([C@@](Cn5ccnc5CC)(c5cccc(F)c5)[C@H]5CCC[C@@H]5NC(=O)OC)CC4)C3)cc2)CC1] | methyl ((1S,2R)-2-((S)-1-(1-((1-(4-((1-acryloylpiperidin-4-yl)sulfonyl)phenyl)azetidin-3-yl)methyl)piperidin-4-yl)-2-(2-ethyl-1H-imidazol-1-yl)-1-(3-fluorophenyl)ethyl)cyclopentyl)carbamate |

TABLE 1-continued

| Cpd No. | Structure | Name |
|---|---|---|
| 27 | 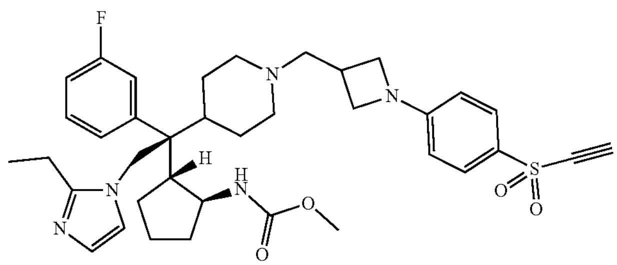 [SMILES: C#CS(=O)(=O)c1ccc(N2CC(CN3CCC([C@@](Cn4ccnc4CC)(c4cccc(F)c4)[C@H]4CCC[C@@H]4NC(=O)OC)CC3)C2)cc1] | methyl ((1S,2R)-2-((S)-2-(2-ethyl-1H-imidazol-1-yl)-1-(1-((1-(4-(ethynylsulfonyl)phenyl)azetidin-3-yl)methyl)piperidin-4-yl)-1-(3-fluorophenyl)ethyl)cyclopentyl)carbamate |
| 28 | 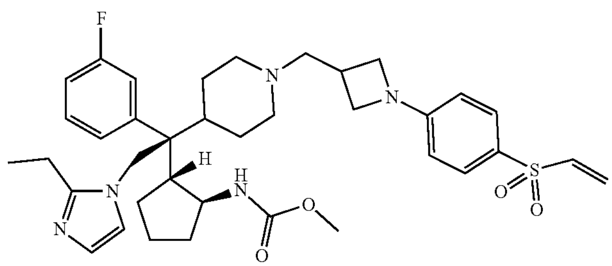 [SMILES: C=CS(=O)(=O)c1ccc(N2CC(CN3CCC([C@@](Cn4ccnc4CC)(c4cccc(F)c4)[C@H]4CCC[C@@H]4NC(=O)OC)CC3)C2)cc1] | methyl ((1S,2R)-2-((S)-2-(2-ethyl-1H-imidazol-1-yl)-1-(3-fluorophenyl)-1-(1-((1-(4-(vinylsulfonyl)phenyl)azetidin-3-yl)methyl)piperidin-4-yl)ethyl)cyclopentyl)carbamate |
| 29 | 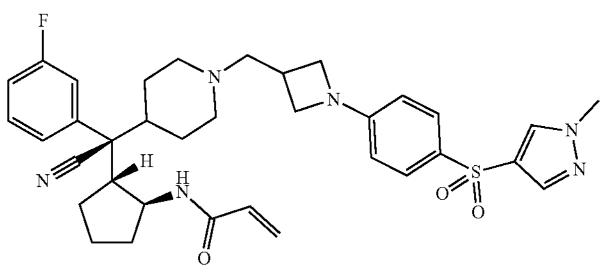 [SMILES: C=CC(=O)N[C@H]1CCC[C@@H]1[C@](C#N)(c1cccc(F)c1)C1CCN(CC2CN(c3ccc(S(=O)(=O)c4cnn(C)c4)cc3)C2)CC1] | N-((1S,2R)-2-((S)-cyano(3-fluorophenyl)(1-((1-(4-((1-methyl-1H-pyrazol-4-yl)sulfonyl)phenyl)azetidin-3-yl)methyl)piperidin-4-yl)methyl)cyclopentyl)acrylamide |
| 30 | 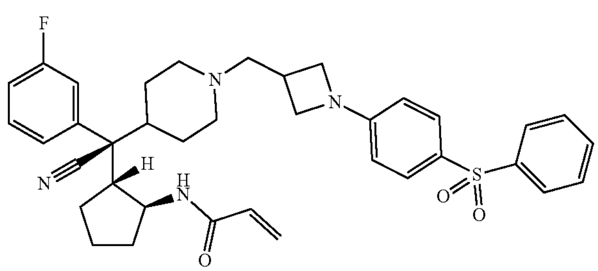 [SMILES: C=CC(=O)N[C@H]1CCC[C@@H]1[C@](C#N)(c1cccc(F)c1)C1CCN(CC2CN(c3ccc(S(=O)(=O)c4ccccc4)cc3)C2)CC1] | N-((1S,2R)-2-((S)-cyano(3-fluorophenyl)(1-((1-(4-(phenylsulfonyl)phenyl)azetidin-3-yl)methyl)piperidin-4-yl)methyl)cyclopentyl)acrylamide |
| 31 | 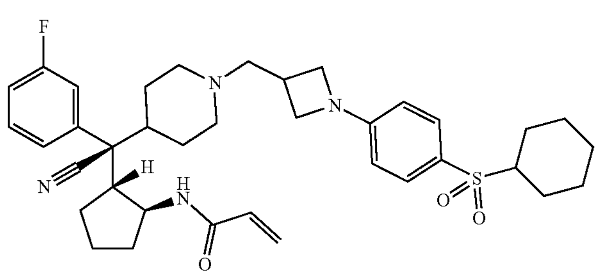 [SMILES: C=CC(=O)N[C@H]1CCC[C@@H]1[C@](C#N)(c1cccc(F)c1)C1CCN(CC2CN(c3ccc(S(=O)(=O)C4CCCCC4)cc3)C2)CC1] | N-((1S,2R)-2-((S)-cyano(1-((1-(4-(cyclohexylsulfonyl)phenyl)azetidin-3-yl)methyl)piperidin-4-yl)(3-fluorophenyl)methyl)cyclopentyl)acrylamide |

TABLE 1-continued

| Cpd No. | Structure | Name |
|---|---|---|
| 32 | 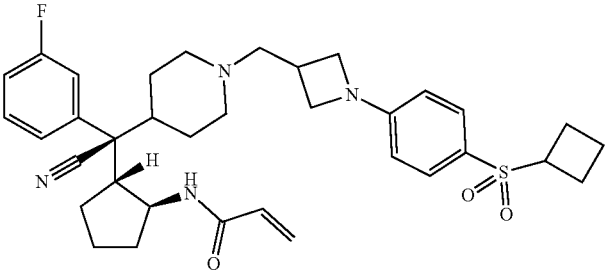 [SMILES: C=CC(=O)N[C@H]1CCC[C@@H]1[C@](C#N)(c1cccc(F)c1)C1CCN(CC2CN(c3ccc(S(=O)(=O)C4CCC4)cc3)C2)CC1] | N-((1S,2R)-2-((S)-cyano(1-((1-(4-(cyclobutylsulfonyl)phenyl)azetidin-3-yl)methyl)piperidin-4-yl)(3-fluorophenyl)methyl)cyclopentyl)acrylamide |
| 33 | 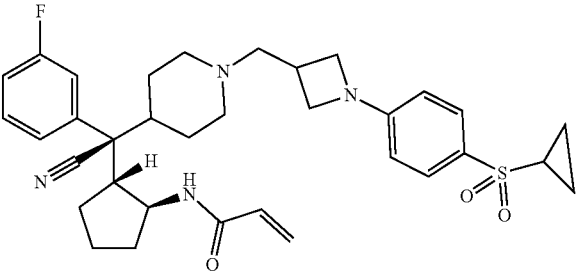 [SMILES: C=CC(=O)N[C@H]1CCC[C@@H]1[C@](C#N)(c1cccc(F)c1)C1CCN(CC2CN(c3ccc(S(=O)(=O)C4CC4)cc3)C2)CC1] | N-((1S,2R)-2-((S)-cyano(1-((1-(4-(cyclopropylsulfonyl)phenyl)azetidin-3-yl)methyl)piperidin-4-yl)(3-fluorophenyl)methyl)cyclopentyl)acrylamide |
| 34 | 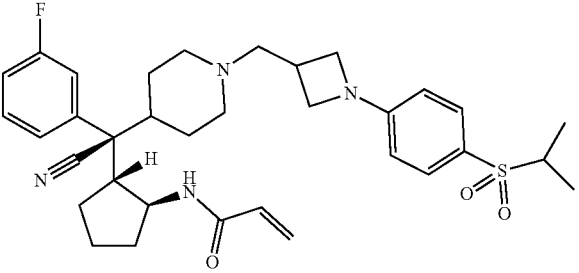 [SMILES: C=CC(=O)N[C@H]1CCC[C@@H]1[C@](C#N)(c1cccc(F)c1)C1CCN(CC2CN(c3ccc(S(=O)(=O)C(C)C)cc3)C2)CC1] | N-((1S,2R)-2-((S)-cyano(3-fluorophenyl)(1-((1-(4-(isopropylsulfonyl)phenyl)azetidin-3-yl)methyl)piperidin-4-yl)methyl)cyclopentyl)acrylamide |
| 35 | 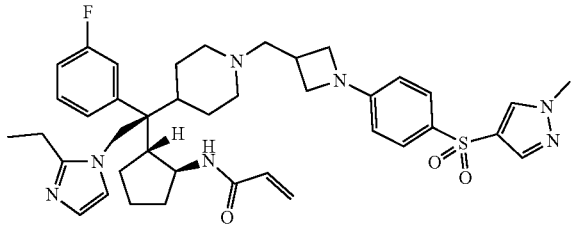 [SMILES: C=CC(=O)N[C@H]1CCC[C@@H]1[C@](Cn1ccnc1CC)(c1cccc(F)c1)C1CCN(CC2CN(c3ccc(S(=O)(=O)c4cnn(C)c4)cc3)C2)CC1] | N-((1S,2R)-2-((S)-2-(2-ethyl-1H-imidazol-1-yl)-1-(3-fluorophenyl)-1-(1-((1-(4-((1-methyl-1H-pyrazol-4-yl)sulfonyl)phenyl)azetidin-3-yl)methyl)piperidin-4-yl)ethyl)cyclopentyl)acrylamide |
| 36 | 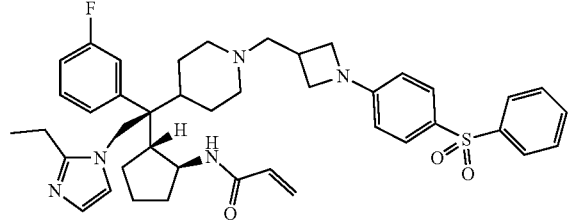 [SMILES: C=CC(=O)N[C@H]1CCC[C@@H]1[C@](Cn1ccnc1CC)(c1cccc(F)c1)C1CCN(CC2CN(c3ccc(S(=O)(=O)c4ccccc4)cc3)C2)CC1] | N-((1S,2R)-2-((S)-2-(2-ethyl-1H-imidazol-1-yl)-1-(3-fluorophenyl)-1-(1-((1-(4-(phenylsulfonyl)phenyl)azetidin-3-yl)methyl)piperidin-4-yl)ethyl)cyclopentyl)acrylamide |
| 37 | 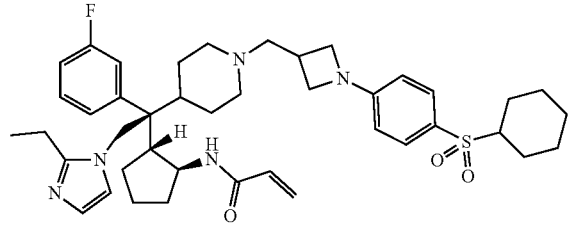 [SMILES: C=CC(=O)N[C@H]1CCC[C@@H]1[C@](Cn1ccnc1CC)(c1cccc(F)c1)C1CCN(CC2CN(c3ccc(S(=O)(=O)C4CCCCC4)cc3)C2)CC1] | N-((1S,2R)-2-((S)-1-(1-((1-(4-(cyclohexylsulfonyl)phenyl)azetidin-3-yl)methyl)piperidin-4-yl)-2-(2-ethyl-1H-imidazol-1-yl)-1-(3-fluorophenyl)ethyl)cyclopentyl)acrylamide |

TABLE 1-continued

| Cpd No. | Structure | Name |
|---|---|---|
| 38 | 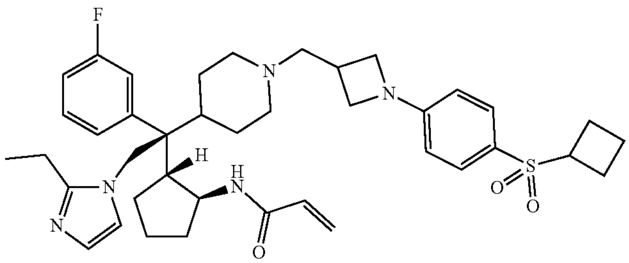 [SMILES: C=CC(=O)N[C@H]1CCC[C@@H]1[C@](Cn1ccnc1CC)(c1cccc(F)c1)C1CCN(CC2CN(c3ccc(S(=O)(=O)C4CCC4)cc3)C2)CC1] | N-((1S,2R)-2-((S)-1-(1-((1-(4-(cyclobutylsulfonyl)phenyl)azetidin-3-yl)methyl)piperidin-4-yl)-2-(2-ethyl-1H-imidazol-1-yl)-1-(3-fluorophenyl)ethyl)cyclopentyl)acrylamide |
| 39 | 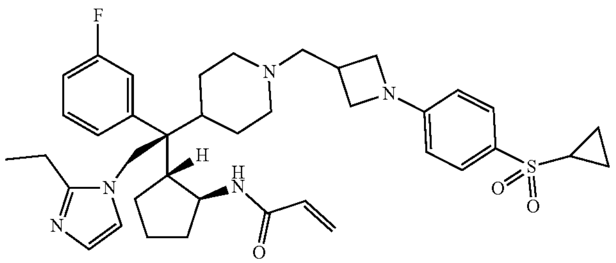 [SMILES: C=CC(=O)N[C@H]1CCC[C@@H]1[C@](Cn1ccnc1CC)(c1cccc(F)c1)C1CCN(CC2CN(c3ccc(S(=O)(=O)C4CC4)cc3)C2)CC1] | N-((1S,2R)-2-((S)-1-(1-((1-(4-(cyclopropylsulfonyl)phenyl)azetidin-3-yl)methyl)piperidin-4-yl)-2-(2-ethyl-1H-imidazol-1-yl)-1-(3-fluorophenyl)ethyl)cyclopentyl)acrylamide |
| 40 | 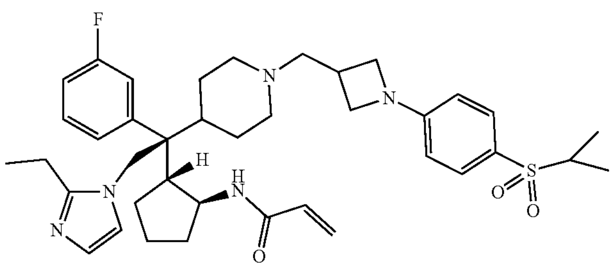 [SMILES: C=CC(=O)N[C@H]1CCC[C@@H]1[C@](Cn1ccnc1CC)(c1cccc(F)c1)C1CCN(CC2CN(c3ccc(S(=O)(=O)C(C)C)cc3)C2)CC1] | N-((1S,2R)-2-((S)-2-(2-ethyl-1H-imidazol-1-yl)-1-(3-fluorophenyl)-1-(1-((1-(4-(isopropylsulfonyl)phenyl)azetidin-3-yl)methyl)piperidin-4-yl)ethyl)cyclopentyl)acrylamide |
| 41 | 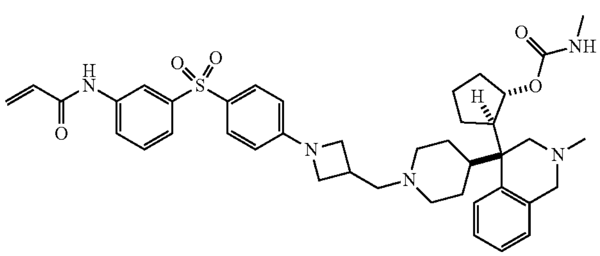 | (1S,2R)-2-((S)-4-(1-((1-(4-((3-acrylamidophenyl)sulfonyl)phenyl)azetidin-3-yl)methyl)piperidin-4-yl)-2-methyl-1,2,3,4-tetrahydroisoquinolin-4-yl)cyclopentyl methylcarbamate |
| 42 | 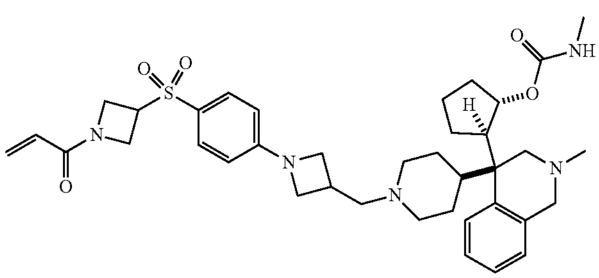 | (1S,2R)-2-((S)-4-(1-((1-(4-((1-acryloylazetidin-3-yl)sulfonyl)phenyl)azetidin-3-yl)methyl)piperidin-4-yl)-2-methyl-1,2,3,4-tetrahydroisoquinolin-4-yl)cyclopentyl methylcarbamate |

TABLE 1-continued

| Cpd No. | Structure | Name |
|---|---|---|
| 43 | 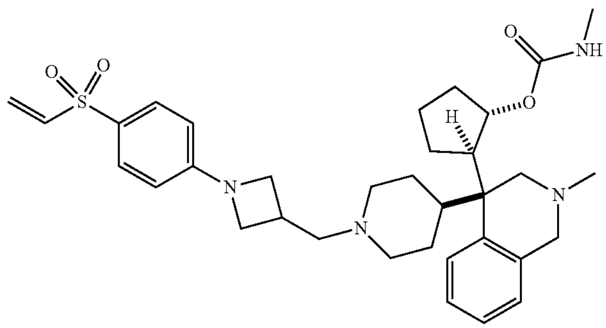 | (1S,2R)-2-((S)-2-methyl-4-(1-((1-(4-(vinylsulfonyl)phenyl)azetidin-3-yl)methyl)piperidin-4-yl)-1,2,3,4-tetrahydroisoquinolin-4-yl)cyclopentyl methylcarbamate |
| 44 | 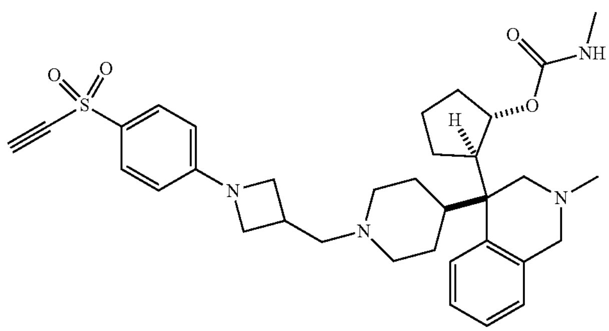 | (1S,2R)-2-((S)-4-(1-((1-(4-(ethynylsulfonyl)phenyl)azetidin-3-yl)methyl)piperidin-4-yl)-2-methyl-1,2,3,4-tetrahydroisoquinolin-4-yl)cyclopentyl methylcarbamate |
| 45 | 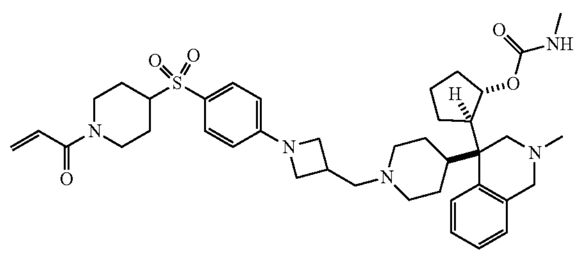 | (1S,2R)-2-((S)-4-(1-((1-(4-((1-acryloylpiperidin-4-yl)sulfonyl)phenyl)azetidin-3-yl)methyl)piperidin-4-yl)-2-methyl-1,2,3,4-tetrahydroisoquinolin-4-yl)cyclopentyl methylcarbamate |
| 46 | 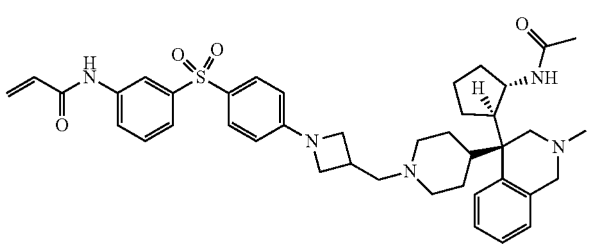 | N-(3-((4-(3-((4-((S)-4-((1R,2S)-2-acetamidocyclopentyl)-2-methyl-1,2,3,4-tetrahydroisoquinolin-4-yl)piperidin-1-yl)methyl)azetidin-1-yl)phenyl)sulfonyl)phenyl)acrylamide |
| 47 | 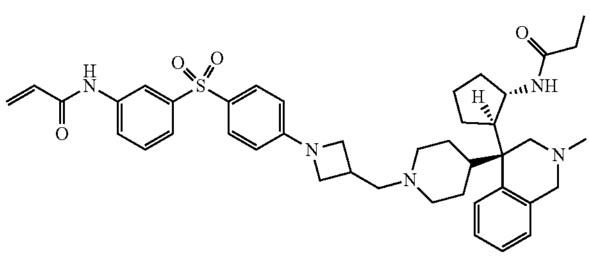 | N-(3-((4-(3-((4-((S)-2-methyl-4-((1R,2S)-2-propionamidocyclopentyl)-1,2,3,4-tetrahydroisoquinolin-4-yl)piperidin-1-yl)methyl)azetidin-1-yl)phenyl)sulfonyl)phenyl)acrylamide |

TABLE 1-continued

| Cpd No. | Structure | Name |
|---|---|---|
| 48 | 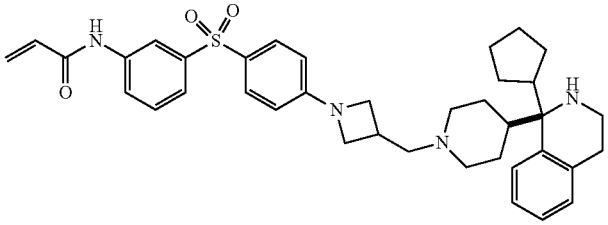 | (R)-N-(3-((4-(3-((4-(1-cyclopentyl-1,2,3,4-tetrahydroisoquinolin-1-yl)piperidin-1-yl)methyl)azetidin-1-yl)phenyl)sulfonyl)phenyl)acrylamide |
| 49 | 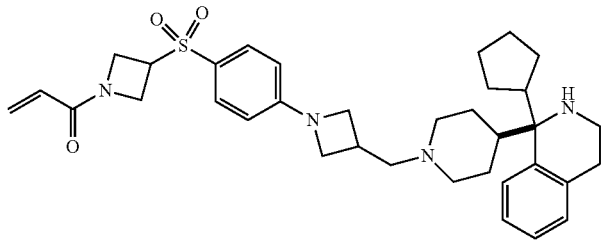 | (R)-1-(3-((4-(3-((4-(1-cyclopentyl-1,2,3,4-tetrahydroisoquinolin-1-yl)piperidin-1-yl)methyl)azetidin-1-yl)phenyl)sulfonyl)azetidin-1-yl)prop-2-en-1-one |
| 50 | 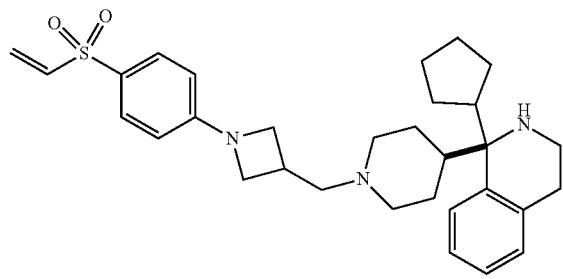 | (R)-1-cyclopentyl-1-(1-((1-(4-(vinylsulfonyl)phenyl)azetidin-3-yl)methyl)piperidin-4-yl)-1,2,3,4-tetrahydroisoquinoline |
| 51 | 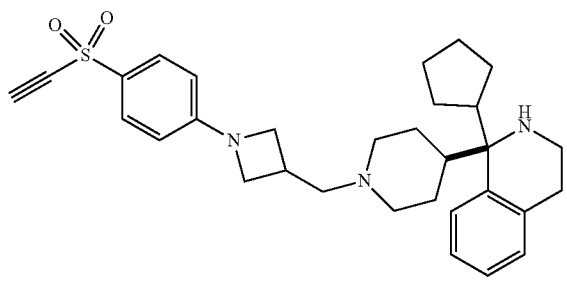 | (R)-1-cyclopentyl-1-(1-((1-(4-(ethynylsulfonyl)phenyl)azetidin-3-yl)methyl)piperidin-4-yl)-1,2,3,4-tetrahydroisoquinoline |
| 52 | 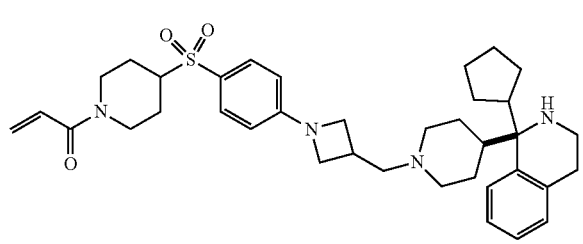 | (R)-1-(4-((4-(3-((4-(1-cyclopentyl-1,2,3,4-tetrahydroisoquinolin-1-yl)piperidin-1-yl)methyl)azetidin-1-yl)phenyl)sulfonyl)piperidin-1-yl)prop-2-en-1-one |

TABLE 1-continued

| Cpd No. | Structure | Name |
|---|---|---|
| 53 | 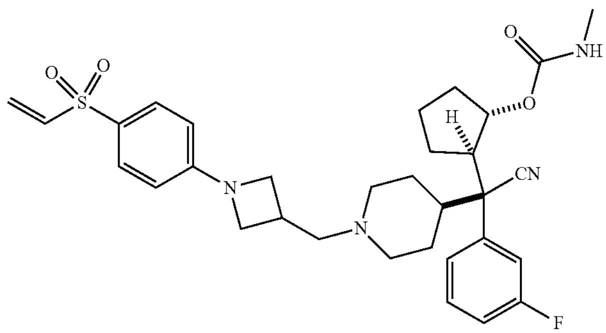 | (1S,2R)-2-((S)-cyano(3-fluorophenyl)(1-((1-(4-(vinylsulfonyl)phenyl)azetidin-3-yl)methyl)piperidin-4-yl)methyl)cyclopentyl methylcarbamate |
| 54 | 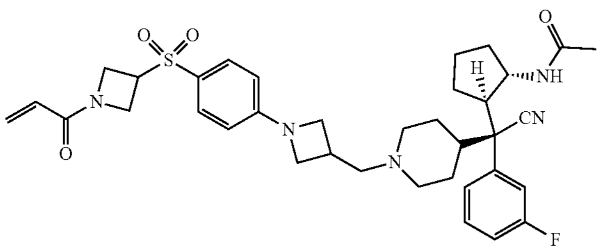 | N-((1S,2R)-2-((S)-(1-((1-(4-((1-acryloylazetidin-3-yl)sulfonyl)phenyl)azetidin-3-yl)methyl)piperidin-4-yl)(cyano)(3-fluorophenyl)methyl)cyclopentyl)acetamide |
| 55 | 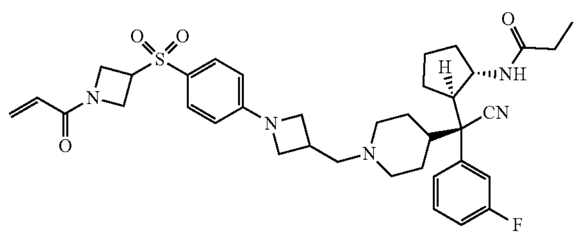 | N-((1S,2R)-2-((S)-(1-((1-(4-((1-acryloylazetidin-3-yl)sulfonyl)phenyl)azetidin-3-yl)methyl)piperidin-4-yl)(cyano)(3-fluorophenyl)methyl)cyclopentyl)propionamide |
| 56 | 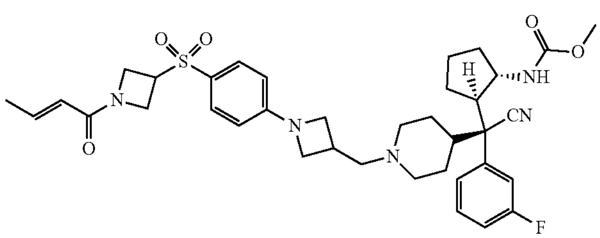 | methyl ((1S,2R)-2-((S)-(1-((1-(4-((1-((E)-but-2-enoyl)azetidin-3-yl)sulfonyl)phenyl)azetidin-3-yl)methyl)piperidin-4-yl)(cyano)(3-fluorophenyl)methyl)cyclopentyl)carbamate |
| 57 | 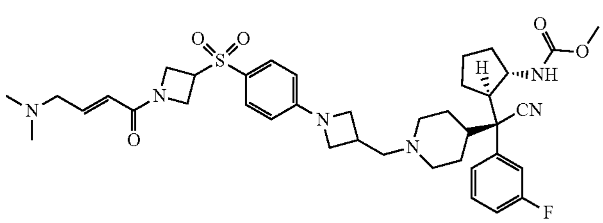 | methyl ((1S,2R)-2-((S)-cyano(1-((1-(4-((1-((E)-4-(dimethylamino)but-2-enoyl)azetidin-3-yl)sulfonyl)phenyl)azetidin-3-yl)methyl)piperidin-4-yl)(3-fluorophenyl)methyl)cyclopentyl)carbamate |
| 58 | 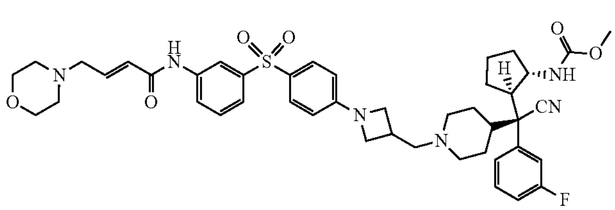 | methyl ((1S,2R)-2-((S)-cyano(3-fluorophenyl)(1-((1-(4-((3-((E)-4-morpholinobut-2-enamido)phenyl)sulfonyl)phenyl)azetidin-3-yl)methyl)piperidin-4-yl)methyl)cyclopentyl)carbamate |

TABLE 1-continued

| Cpd No. | Structure | Name |
|---|---|---|
| 59 | 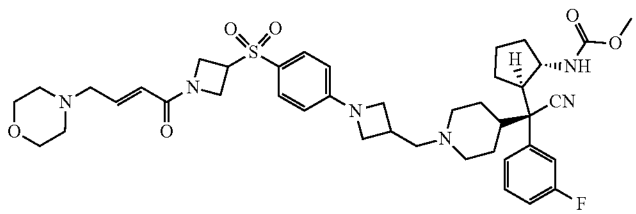 | methyl ((1S,2R)-2-((S)-cyano(3-fluorophenyl)(1-((1-(4-((1-((E)-4-morpholinobut-2-enoyl)azetidin-3-yl)sulfonyl)phenyl)azetidin-3-yl)methyl)piperidin-4-yl)methyl)cyclopentyl)carbamate |
| 60 | 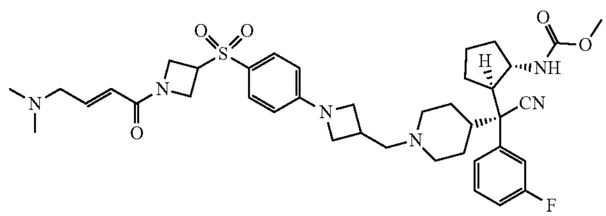 | methyl ((1S,2R)-2-((R)-cyano(1-((1-(4-(1-((E)-4-(dimethylamino)but-2-enoyl)azetidin-3-yl)sulfonyl)phenyl)azetidin-3-yl)methyl)piperidin-4-yl)(3-fluorophenyl)methyl)cyclopentyl)carbamate |
| 61 | 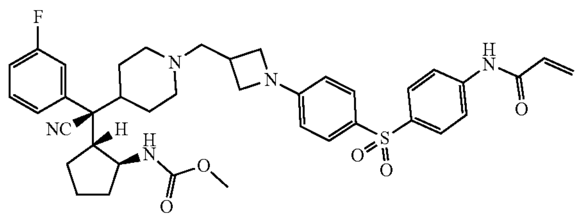 [SMILES: C=CC(=O)Nc1ccc(S(=O)(=O)c2ccc(N3CC(CN4CCC([C@@](C#N)(c5cccc(F)c5)[C@H]5CCC[C@@H]5NC(=O)OC)CC4)C3)cc2)cc1] | methyl ((1S,2R)-2-((S)-(1-((1-(4-((4-acrylamidophenyl)sulfonyl)phenyl)azetidin-3-yl)methyl)piperidin-4-yl)(cyano)(3-fluorophenyl)methyl)cyclopentyl)carbamate |
| 62 | 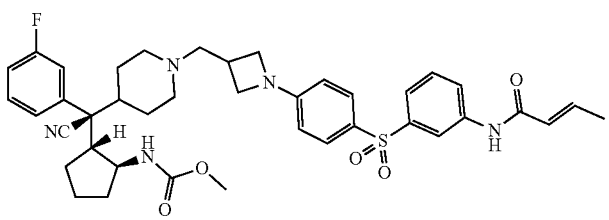 [SMILES: C/C=C/C(=O)Nc1cccc(S(=O)(=O)c2ccc(N3CC(CN4CCC([C@@](C#N)(c5cccc(F)c5)[C@H]5CCC[C@@H]5NC(=O)OC)CC4)C3)cc2)c1] | methyl ((1S,2R)-2-((S)-(1-((1-(4-((3-((E)-but-2-enamido)phenyl)sulfonyl)phenyl)azetidin-3-yl)methyl)piperidin-4-yl)(cyano)(3-fluorophenyl)methyl)cyclopentyl)carbamate |
| 63 | 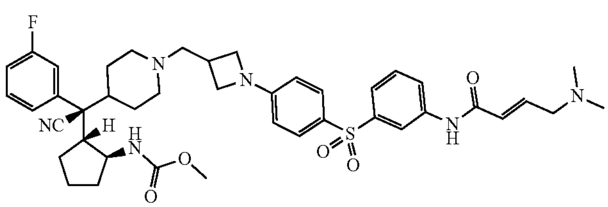 [SMILES: COC(=O)N[C@H]1CCC[C@@H]1[C@](C#N)(c1cccc(F)c1)C1CCN(CC2CN(c3ccc(S(=O)(=O)c4cccc(NC(=O)/C=C/CN(C)C)c4)cc3)C2)CC1] | methyl ((1S,2R)-2-((S)-cyano(1-((1-(4-((3-((E)-4-(dimethylamino)but-2-enamido)phenyl)sulfonyl)phenyl)azetidin-3-yl)methyl)piperidin-4-yl)(3-fluorophenyl)methyl)cyclopentyl)carbamate |
| 66 | 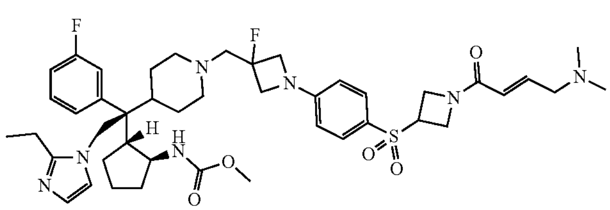 [SMILES: CCc1nccn1C[C@@](c1cccc(F)c1)(C1CCN(CC2(F)CN(c3ccc(S(=O)(=O)C4CN(C(=O)/C=C/CN(C)C)C4)cc3)C2)CC1)[C@H]1CCC[C@@H]1NC(=O)OC] | methyl ((1S,2R)-2-((S)-1-(1-((1-(4-((1-((E)-4-(dimethylamino)but-2-enoyl)azetidin-3-yl)sulfonyl)phenyl)-3-fluoroazetidin-3-yl)methyl)piperidin-4-yl)-2-(2-ethyl-1H-imidazol-1-yl)-1-(3-fluorophenyl)ethyl)cyclopentyl)carbamate |
| 67 | 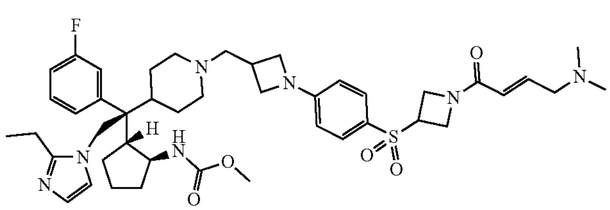 [SMILES: CCc1nccn1C[C@@](c1cccc(F)c1)(C1CCN(CC2CN(c3ccc(S(=O)(=O)C4CN(C(=O)/C=C/CN(C)C)C4)cc3)C2)CC1)[C@H]1CCC[C@@H]1NC(=O)OC] | methyl ((1S,2R)-2-((S)-1-(1-((1-(4-((1-((E)-4-(dimethylamino)but-2-enoyl)azetidin-3-yl)sulfonyl)phenyl)azetidin-3-yl)methyl)piperidin-4-yl)-2-(2-ethyl-1H-imidazol-1-yl)-1-(3-fluorophenyl)ethyl)cyclopentyl)carbamate |

TABLE 1-continued

| Cpd No. | Structure | Name |
|---|---|---|
| 69 | 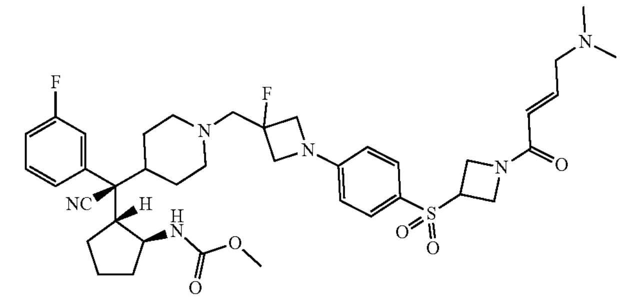 [SMILES: COC(=O)N[C@H]1CCC[C@@H]1[C@](C#N)(c1cccc(F)c1)C1CCN(CC2(F)CN(c3ccc(S(=O)(=O)C4CN(C(=O)/C=C/CN(C)C)C4)cc3)C2)CC1] | methyl ((1S,2R)-2-((S)-cyano(1-((1-(4-((1-((E)-4-(dimethylamino)but-2-enoyl)azetidin-3-yl)sulfonyl)phenyl)-3-fluoroazetidin-3-yl)methyl)piperidin-4-yl)(3-fluorophenyl)methyl)cyclopentyl)carbamate |
| 70 | 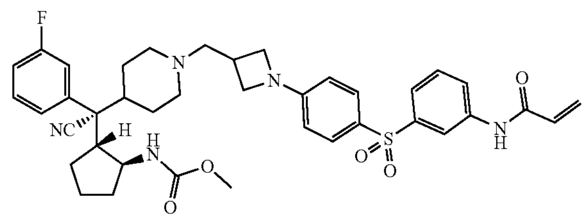 [SMILES: C=CC(=O)Nc1cccc(S(=O)(=O)c2ccc(N3CC(CN4CCC([C@](C#N)(c5cccc(F)c5)[C@H]5CCC[C@@H]5NC(=O)OC)CC4)C3)cc2)c1] | methyl ((1S,2R)-2-((R)-(1-((1-(4-((3-acrylamidophenyl)sulfonyl)phenyl)azetidin-3-yl)methyl)piperidin-4-yl)(cyano)(3-fluorophenyl)methyl)cyclopentyl)carbamate |
| 71 | 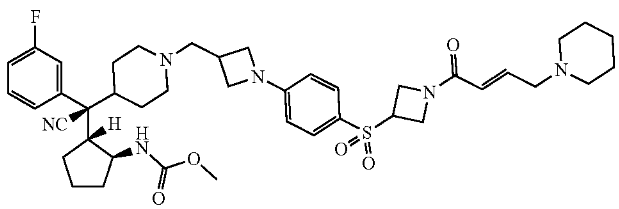 [SMILES: COC(=O)N[C@H]1CCC[C@@H]1[C@](C#N)(c1cccc(F)c1)C1CCN(CC2CN(c3ccc(S(=O)(=O)C4CN(C(=O)/C=C/CN5CCCCC5)C4)cc3)C2)CC1] | methyl ((1S,2R)-2-((S)-cyano(3-fluorophenyl)(1-((1-(4-((1-((E)-4-(piperidin-1-yl)but-2-enoyl)azetidin-3-yl)sulfonyl)phenyl)azetidin-3-yl)methyl)piperidin-4-yl)methyl)cyclopentyl)carbamate |
| 72 | 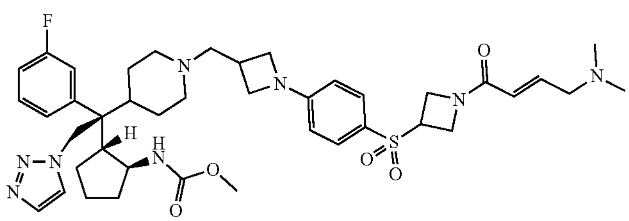 [SMILES: COC(=O)N[C@H]1CCC[C@@H]1[C@](Cn1ccnn1)(c1cccc(F)c1)C1CCN(CC2CN(c3ccc(S(=O)(=O)C4CN(C(=O)/C=C/CN(C)C)C4)cc3)C2)CC1] | methyl ((1S,2R)-2-((S)-1-(1-((1-(4-((1-((E)-4-(dimethylamino)but-2-enoyl)azetidin-3-yl)sulfonyl)phenyl)azetidin-3-yl)methyl)piperidin-4-yl)-1-(3-fluorophenyl)-2-(1H-1,2,3-triazol-1-yl)ethyl)cyclopentyl)carbamate |
| 73 | 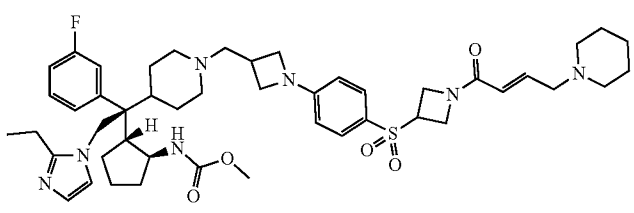 [SMILES: CCc1nccn1C[C@@](c1cccc(F)c1)(C1CCN(CC2CN(c3ccc(S(=O)(=O)C4CN(C(=O)/C=C/CN5CCCCC5)C4)cc3)C2)CC1)[C@H]1CCC[C@@H]1NC(=O)OC] | methyl ((1S,2R)-2-((S)-2-(2-ethyl-1H-imidazol-1-yl)-1-(3-fluorophenyl)-1-(1-((1-(4-((1-((E)-4-(piperidin-1-yl)but-2-enoyl)azetidin-3-yl)sulfonyl)phenyl)azetidin-3-yl)methyl)piperidin-4-yl)ethyl)cyclopentyl)carbamate |
| 74 | 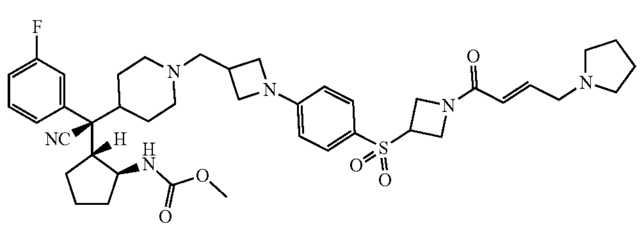 [SMILES: COC(=O)N[C@H]1CCC[C@@H]1[C@](C#N)(c1cccc(F)c1)C1CCN(CC2CN(c3ccc(S(=O)(=O)C4CN(C(=O)/C=C/CN5CCCC5)C4)cc3)C2)CC1] | methyl ((1S,2R)-2-((S)-cyano(3-fluorophenyl)(1-((1-(4-((1-((E)-4-(pyrrolidin-1-yl)but-2-enoyl)azetidin-3-yl)sulfonyl)phenyl)azetidin-3-yl)methyl)piperidin-4-yl)methyl)cyclopentyl)carbamate |

TABLE 1-continued

| Cpd No. | Structure | Name |
|---|---|---|
| 75 | 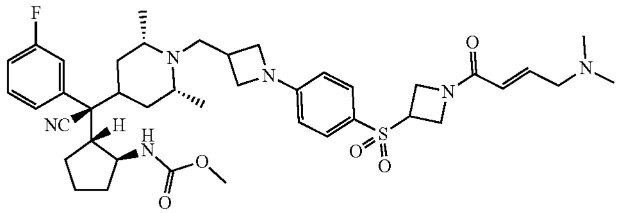 [SMILES: COC(=O)N[C@H]1CCC[C@@H]1[C@](C#N)(c1cccc(F)c1)C1C[C@@H](C)N(CC2CN(c3ccc(S(=O)(=O)C4CN(C(=O)/C=C/CN(C)C)C4)cc3)C2)[C@@H](C)C1] | methyl ((1S,2R)-2-((1S)-cyano((2R,6S)-1-((1-(4-((1-((E)-4-(dimethylamino)but-2-enoyl)azetidin-3-yl)sulfonyl)phenyl)azetidin-3-yl)methyl)-2,6-dimethylpiperidin-4-yl)(3-fluorophenyl)methyl)cyclopentyl)carbamate |
| 76 | 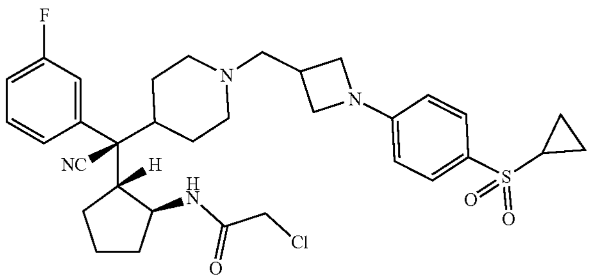 [SMILES: N#C[C@@](c1cccc(F)c1)(C1CCN(CC2CN(c3ccc(S(=O)(=O)C4CC4)cc3)C2)CC1)[C@H]1CCC[C@@H]1NC(=O)CCl] | 2-chloro-N-((1S,2R)-2-((S)-cyano(1-((1-(4-(cyclopropylsulfonyl)phenyl)azetidin-3-yl)methyl)piperidin-4-yl)(3-fluorophenyl)methyl)cyclopentyl)acetamide |
| 77 | 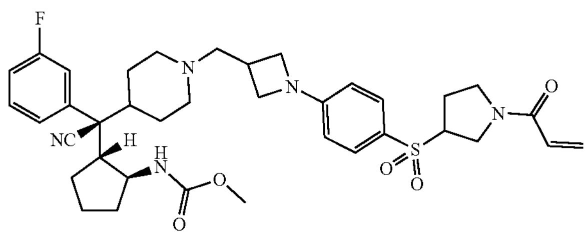 [SMILES: C=CC(=O)N1CCC(S(=O)(=O)c2ccc(N3CC(CN4CCC([C@@](C#N)(c5cccc(F)c5)[C@H]5CCC[C@@H]5NC(=O)OC)CC4)C3)cc2)C1] | methyl ((1S,2R)-2-((1S)-(1-((1-(4-((1-acryloylpyrrolidin-3-yl)sulfonyl)phenyl)azetidin-3-yl)methyl)piperidin-4-yl)(cyano)(3-fluorophenyl)methyl)cyclopentyl)carbamate |
| 78 | 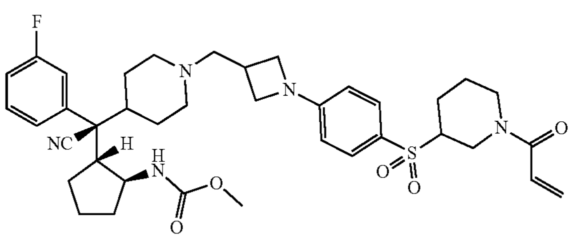 [SMILES: C=CC(=O)N1CCCC(S(=O)(=O)c2ccc(N3CC(CN4CCC([C@@](C#N)(c5cccc(F)c5)[C@H]5CCC[C@@H]5NC(=O)OC)CC4)C3)cc2)C1] | methyl ((1S,2R)-2-((1S)-(1-((1-(4-((1-acryloylpiperidin-3-yl)sulfonyl)phenyl)azetidin-3-yl)methyl)piperidin-4-yl)(cyano)(3-fluorophenyl)methyl)cyclopentyl)carbamate |

TABLE 1A

| Cpd No. | Structure | Name |
|---|---|---|
| 68 | 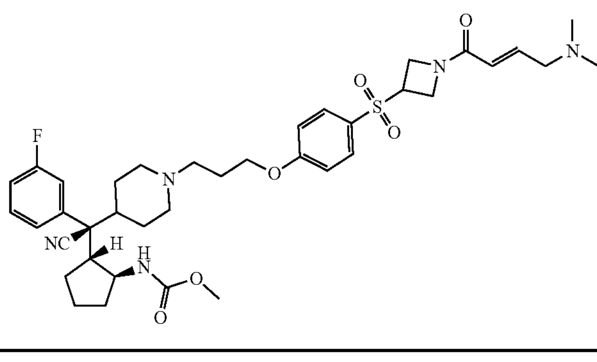 | methyl ((1S,2R)-2-((S)-cyano(1-(3-(4-((1-((E)-4-(dimethylamino)but-2-enoyl)azetidin-3-yl)sulfonyl)phenoxy)propyl)piperidin-4-yl)(3-fluorophenyl)methyl)cyclopentyl)carbamate |

TABLE 1B

| Cpd No. | Structure | Name |
|---|---|---|
| 64 | 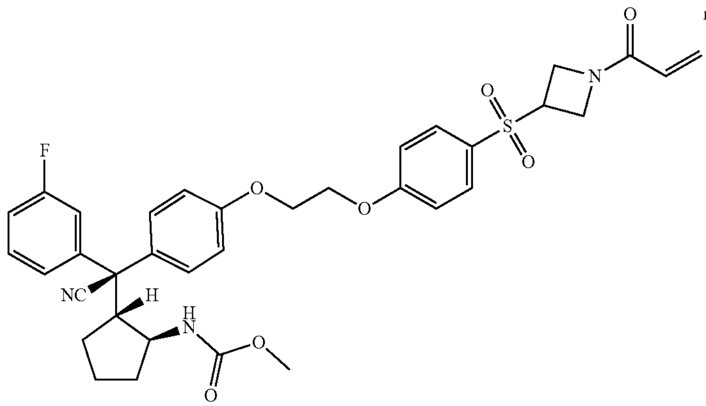 [SMILES: C=CC(=O)N1CC(S(=O)(=O)c2ccc(OCCOc3ccc([C@@](C#N)(c4cccc(F)c4)[C@H]4CCC[C@@H]4NC(=O)OC)cc3)cc2)C1] | methyl ((1S,2R)-2-((R)-(4-(2-(4-((1-acryloylazetidin-3-yl)sulfonyl)phenoxy)ethoxy)phenyl)(cyano)(3-fluorophenyl)methyl)cyclopentyl)carbamate |
| 65 | 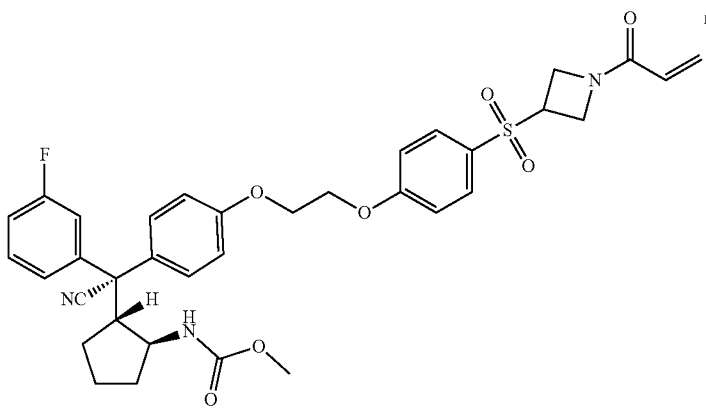 [SMILES: C=CC(=O)N1CC(S(=O)(=O)c2ccc(OCCOc3ccc([C@](C#N)(c4cccc(F)c4)[C@H]4CCC[C@@H]4NC(=O)OC)cc3)cc2)C1] | methyl ((1S,2R)-2-((S)-(4-(2-(4-((1-acryloylazetidin-3-yl)sulfonyl)phenoxy)ethoxy)phenyl)(cyano)(3-fluorophenyl)methyl)cyclopentyl)carbamate |

TABLE 1C

| Cpd No. | Structure | Name |
|---|---|---|
| 79 | 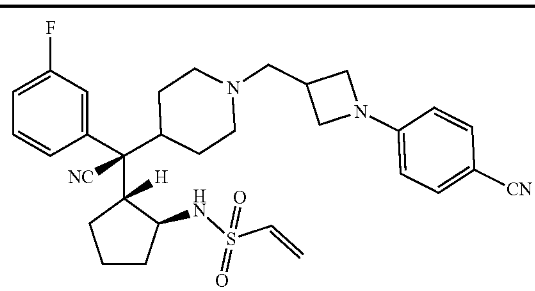 | N-((1S,2R)-2-((S)-cyano(1-((1-(4-cyanophenyl)azetidin-3-yl)methyl)piperidin-4-yl)(3-fluorophenyl)methyl)cyclopentyl)ethenesulfonamide |
| 80 | 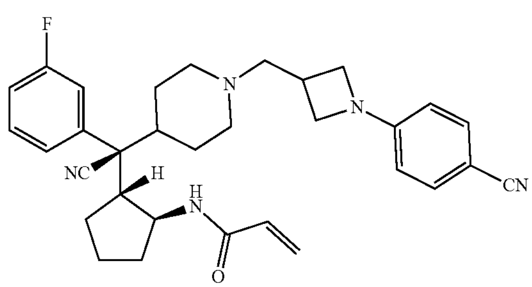 [SMILES: C=CC(=O)N[C@H]1CCC[C@@H]1[C@](C#N)(c1cccc(F)c1)C1CCN(CC2CN(c3ccc(C#N)cc3)C2)CC1] | N-((1S,2R)-2-((S)-cyano(1-((1-(4-cyanophenyl)azetidin-3-yl)methyl)piperidin-4-yl)(3-fluorophenyl)methyl)cyclopentyl)acrylamide |

TABLE 1C-continued

| Cpd No. | Structure | Name |
|---|---|---|
| 81 | 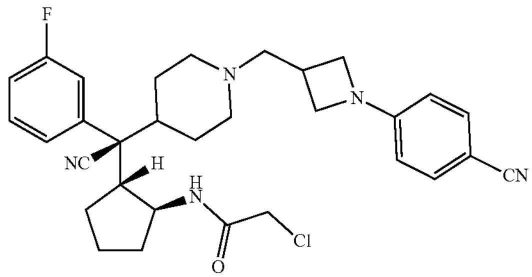 [SMILES: N#Cc1ccc(N2CC(CN3CCC([C@@](C#N)(c4cccc(F)c4)[C@H]4CCC[C@@H]4NC(=O)CCl)CC3)C2)cc1] | 2-chloro-N-((1S,2R)-2-((S)-cyano(1-((1-(4-cyanophenyl)azetidin-3-yl)methyl)piperidin-4-yl)(3-fluorophenyl)methyl)cyclopentyl)acetamide |
| 82 | 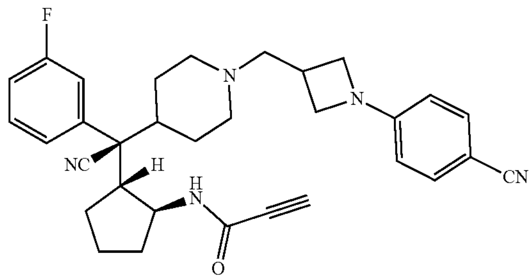 [SMILES: C#CC(=O)N[C@H]1CCC[C@@H]1[C@](C#N)(c1cccc(F)c1)C1CCN(CC2CN(c3ccc(C#N)cc3)C2)CC1] | N-((1S,2R)-2-((S)-cyano(1-((1-(4-cyanophenyl)azetidin-3-yl)methyl)piperidin-4-yl)(3-fluorophenyl)methyl)cyclopentyl)propiolamide |

Compounds of the Disclosure inhibit menin and are useful in the treatment of a variety of diseases and conditions. In particular, Compounds of the Disclosure are useful in methods of treating a disease or condition wherein inhibition of menin provides a benefit, for example, cancers and proliferative diseases. Methods of the disclosure comprise administering a therapeutically effective amount of a Compound of the Disclosure to an individual in need thereof. The present methods also encompass administering a second therapeutic agent to the individual in addition to the Compound of the Disclosure. The second therapeutic agent is selected from drugs known as useful in treating the disease or condition afflicting the individual in need thereof, e.g., a chemotherapeutic agent and/or radiation known as useful in treating a particular cancer.

Salts, hydrates, and solvates of the Compounds of the Disclosure can also be used in the methods disclosed herein. The present disclosure further includes all possible stereoisomers and geometric isomers of Compounds of the Disclosure to include both racemic compounds and optically active isomers. When a Compound of the Disclosure is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the Compounds of the Disclosure are possible, the present disclosure is intended to include all tautomeric forms of the compounds.

The present disclosure encompasses the preparation and use of salts of Compounds of the Disclosure. As used herein, the pharmaceutical "pharmaceutically acceptable salt" refers to salts or zwitterionic forms of Compounds of the Disclosure. Salts of Compounds of the Disclosure can be prepared during the final isolation and purification of the compounds or separately by reacting the compound with an acid having a suitable cation. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate, or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, ethanol, and the like, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1): Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present disclosure provides Compounds of the Disclosure as menin inhibitors for the treatment of diseases and conditions wherein inhibition of menin has a beneficial effect. Compounds of the Disclosure typically have a binding affinity ($IC_{50}$) to menin of less than 100 μM, e.g., less than 50 μM, less than 25 μM, and less than μM, less than about 1 μM, less than about 0.5 μM, less than about 0.1 μM, less than about 0.05 μM, or less than about 0.01 μM. In one embodiment, the present disclosure relates to a method of treating an individual suffering from a disease or condition wherein inhibition of menin provides a benefit comprising administering a therapeutically effective amount of a Compound of the Disclosure to an individual in need thereof.

Diseases and conditions mediated by menin can be treated by administering Compounds of the Disclosure because these compounds are inhibitors of menin. The present disclosure is thus directed generally to a method for treating a condition or disorder responsive to inhibition of menin, in an animal, e.g., a human, suffering from, or at risk of suffering from, the condition or disorder, the method comprising administering to the animal an effective amount of one or more Compounds of the Disclosure.

The present disclosure is further directed to a method of inhibiting menin in an animal in need thereof, said method comprising administering to the animal an effective amount of at least one Compound of the Disclosure.

The methods of the present disclosure can be accomplished by administering a Compound of the Disclosure as the neat compound or as a pharmaceutical composition. Administration of a pharmaceutical composition, or neat compound of a Compound of the Disclosure, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a Compound of the Disclosure and, optionally, a second therapeutic agent, packaged separately or together, and an insert having instructions for using these active agents.

In one embodiment, a Compound of the Disclosure is administered in conjunction with a second therapeutic agent useful in the treatment of a disease or condition wherein inhibition of menin provides a benefit. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered. The Compound of the Disclosure therefore can be used in conjunction with one or more second therapeutic agents, for example, but not limited to, anticancer agents.

Diseases and conditions treatable by the methods of the present disclosure include, but are not limited to, cancer and other proliferative disorders, inflammatory diseases, sepsis, autoimmune disease, and viral infection. In one embodiment, a human patient is treated with a Compound of the Disclosure, or a pharmaceutical composition comprising a Compound of the Disclosure, wherein the compound is administered in an amount sufficient to inhibit menin activity in the patient.

In one embodiment, the disease to be treated by the Compound of the Disclosure is cancer. Examples of treatable cancers include, but are not limited to, any one or more of the cancers of Table 2.

TABLE 2

| | |
|---|---|
| adrenal cancer | lymphoepithelioma |
| acinic cell carcinoma | lymphoma |
| acoustic neuroma | acute lymphocytic leukemia |
| acral lentigious melanoma | acute myelogeous leukemia |
| acrospiroma | chronic lymphocytic leukemia |
| acute eosinophilic leukemia | liver cancer |
| acute erythroid leukemia | small cell lung cancer |
| acute lymphoblastic leukemia | non-small cell lung cancer |
| acute megakaryoblastic leukemia | MALT lymphoma |
| acute monocytic leukemia | malignant fibrous histiocytoma |
| acute promyelocytic leukemia | malignant peripheral nerve sheath tumor |
| adenocarcinoma | malignant triton tumor |
| adenoid cystic carcinoma | mantle cell lymphoma |
| adenoma | marginal zone B-cell lymphoma |
| adenomatoid odontogenic tumor | mast cell leukemia |
| adenosquamous carcinoma | mediastinal germ cell tumor |
| adipose tissue neoplasm | medullary carcinoma of the breast |
| adrenocortical carcinoma | medullary thyroid cancer, |
| adult T-cell leukemia/lymphoma | medulloblastoma |
| aggressive NK-cell leukemia | melanoma, |

TABLE 2-continued

| | |
|---|---|
| AIDS-related lymphoma | meningioma, |
| alveolar rhabdomyosarcoma | merkel cell cancer |
| alveolar soft part sarcoma | mesothelioma |
| ameloblastic fibroma | metastatic urothelial carcinoma |
| anaplastic large cell lymphoma | mixed Mullerian tumor |
| anaplastic thyroid cancer | mucinous tumor |
| angioimmunoblastic T-cell lymphoma, | multiple myeloma |
| angiomyolipoma | muscle tissue neoplasm |
| angiosarcoma | mycosis fungoides |
| astrocytoma | myxoid liposarcoma |
| atypical teratoid rhabdoid tumor | myxoma |
| B-cell chronic lymphocytic leukemia | myxosarcoma |
| B-cell prolymphocytic leukemia | nasopharyngeal carcinoma |
| B-cell lymphoma | neurinoma |
| basal cell carcinoma | neuroblastoma |
| biliary tract cancer | neurofibroma |
| bladder cancer | neuroma |
| blastoma | nodular melanoma |
| bone cancer | ocular cancer |
| Brenner tumor | oligoastrocytoma |
| Brown tumor | oligodendroglioma |
| Burkitt's lymphoma | oncocytoma |
| breast cancer | optic nerve sheath meningioma |
| brain cancer | optic nerve tumor |
| carcinoma | oral cancer |
| carcinoma in situ | osteosarcoma |
| carcinosarcoma | ovarian cancer |
| cartilage tumor | Pancoast tumor |
| cementoma | papillary thyroid cancer |
| myeloid sarcoma | paraganglioma |
| chondroma | pinealoblastoma |
| chordoma | pineocytoma |
| choriocarcinoma | pituicytoma |
| choroid plexus papilloma | pituitary adenoma |
| clear-cell sarcoma of the kidney | pituitary tumor |
| craniopharyngioma | plasmacytoma |
| cutaneous T-cell lymphoma | polyembryoma |
| cervical cancer | precursor T-lymphoblastic lymphoma |
| colorectal cancer | primary central nervous system lymphoma |
| Degos disease | primary effusion lymphoma |
| desmoplastic small round cell tumor | preimary peritoneal cancer |
| diffuse large B-cell lymphoma | prostate cancer |
| dysembryoplastic neuroepithelial tumor, | pancreatic cancer |
| dysgerminoma | pharyngeal cancer |
| embryonal carcinoma | pseudomyxoma periotonei |
| endocrine gland neoplasm | renal cell carcinoma |
| endodermal sinus tumor | renal medullary carcinoma |
| enteropathy-associated T-cell lymphoma | retinoblastoma |
| esophageal cancer | rhabdomyoma |
| fetus in fetu | rhabdomyosarcoma |
| fibroma | Richter's transformation |
| fibrosarcoma | rectal cancer |
| follicular lymphoma | sarcoma |
| follicular thyroid cancer | Schwannomatosis |
| ganglioneuroma | seminoma |
| gastrointestinal cancer | Sertoli cell tumor |
| germ cell tumor | sex cord-gonadal stromal tumor |
| gestational choriocarcinoma | signet ring cell carcinoma |
| giant cell fibroblastoma | skin cancer |
| giant cell tumor of the bone | small blue round cell tumors |
| glial tumor | small cell carcinoma |
| glioblastoma multiforme | soft tissue sarcoma |
| glioma | somatostatinoma |
| gliomatosis cerebri | soot wart |
| glucagonoma | spinal tumor |
| gonadoblastoma | splenic marginal zone lymphoma |
| granulosa cell tumor | squamous cell carcinoma |
| gynandroblastoma | synovial sarcoma |
| gallbladder cancer | Sezary's disease |
| gastric cancer | small intestine cancer |
| hairy cell leukemia | squamous carcinoma |
| hemangioblastoma | stomach cancer |
| head and neck cancer | T-cell lymphoma |
| hemangiopericytoma | testicular cancer |
| hematological malignancy | thecoma |
| hepatoblastoma | thyroid cancer |
| hepatosplenic T-cell lymphoma | transitional cell carcinoma |
| Hodgkin's lymphoma | throat cancer |

TABLE 2-continued

| | |
|---|---|
| non-Hodgkin's lymphoma | urachal cancer |
| invasive lobular carcinoma | urogenital cancer |
| intestinal cancer | urothelial carcinoma |
| kidney cancer | uveal melanoma |
| laryngeal cancer | uterine cancer |
| lentigo maligna | verrucous carcinoma |
| lethal midline carcinoma | visual pathway glioma |
| leukemia | vulvar cancer |
| leydig cell tumor | vaginal cancer |
| liposarcoma | Waldenstrom's macroglobulinemia |
| lung cancer | Warthin's tumor |
| lymphangioma | Wilms' tumor |
| lymphangiosarcoma | |

In another embodiment, the cancer is a leukemia, for example a leukemia selected from acute monocytic leukemia, acute myelogenous leukemia, chronic myelogenous leukemia, chronic lymphocytic leukemia and mixed lineage leukemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In another embodiment, the present disclosure provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

Compounds of the Disclosure can also treat infectious and noninfectious inflammatory events and autoimmune and other inflammatory diseases by administration of an effective amount of a present compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendictitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In another embodiment, the present disclosure provides a method of treating systemic inflammatory response syndromes, such as LPS-induced endotoxic shock and/or bacteria-induced sepsis by administration of an effective amount of a Compound of the Disclosure to a mammal, in particular a human in need of such treatment.

In another embodiment, the present disclosure provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatitis B virus, and hepatitis C virus.

In another embodiment, the present disclosure provides therapeutic method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of a Compound of the Disclosure to a subject in need of such therapy.

In another embodiment, the present disclosure provides a method of regulating endogenous or heterologous promoter activity by contacting a cell with a Compound of the Disclosure.

In methods of the present disclosure, a therapeutically effective amount of a Compound of the Disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the patient, and ultimately is determined by the attendant physician. Dosage amounts and intervals can be adjusted individually to provide plasma levels of the menin inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A Compound of the Disclosure used in a method of the present disclosure can be administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, about 0.05, about 0.5, about 5, about 10, about 20, about 30, about 40, about 50, about 100, about 150, about 200, about 250, about 300, about 350, about 400, about 450, or about 500 milligrams, including all doses between 0.005 and 500 milligrams.

The dosage of a composition containing a Compound of the Disclosure, or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

As stated above, a Compound of the Disclosure can be administered in combination with a second therapeutically active agent. In some embodiments, the second therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, chemotherapeutic agents or other anti-proliferative agents can be combined with Compound of the Disclosure to treat proliferative diseases and cancer. Examples of therapies and anticancer agents that can be used in combination with Compounds of the Disclosure include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Examples of antiproliferative compounds include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include, but are not limited to, steroids, such as atamestane, exemestane, and formestane, and non-steroids, such as aminoglutethimide, roglethimide, pyridoglutethimide, trilostane, testolactone, ketoconazole, vorozole, fadrozole, anastrozole, and letrozole.

Nonlimiting anti-estrogens include, but are not limited to, tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Exemplary topoisomerase I inhibitors include, but are not limited to, topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; vinca alkaloids, such as vinblastine, vinblastine sulfate, vincristine, and vincristine sulfate, and vinorelbine; discodermolides; cochicine and epothilones and derivatives thereof.

Exemplary nonlimiting alkylating agents include cyclophosphamide, ifosfamide, melphalan, and nitrosoureas, such as carmustine and lomustine.

Exemplary nonlimiting cyclooxygenase inhibitors include Cox-2 inhibitors, 5-alkyl substituted 2-arylaminophenylacetic acid and derivatives, such as celecoxib, rofecoxib, etoricoxib, valdecoxib, or a 5-alkyl-2-arylaminophenylacetic acid, such as lumiracoxib.

Exemplary nonlimiting matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary nonlimiting mTOR inhibitors include compounds that inhibit the mammalian target of rapamycin (mTOR) and possess antiproliferative activity such as sirolimus, everolimus, CCI-779, and ABT578.

Exemplary nonlimiting antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Exemplary nonlimiting platin compounds include carboplatin, cis-platin, cisplatinum, and oxaliplatin.

Exemplary nonlimiting methionine aminopeptidase inhibitors include bengamide or a derivative thereof and PPI-2458.

Exemplary nonlimiting bisphosphonates include etridonic acid, clodronic acid, tiludronic acid, pamidronic acid, alendronic acid, ibandronic acid, risedronic acid, and zoledronic acid.

Exemplary nonlimiting antiproliferative antibodies include trastuzumab, trastuzumab-DM1, cetuximab, bevacizumab, rituximab, PR064553, and 2C4. The term "antibody" is meant to include intact monoclonal antibodies, polyclonal antibodies, multispecific antibodies formed from at least two intact antibodies, and antibody fragments, so long as they exhibit the desired biological activity.

Exemplary nonlimiting heparanase inhibitors include compounds that target, decrease, or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras, for example, a farnesyl transferase inhibitor, such as L-744832, DK8G557, tipifarnib, and lonafarnib.

Exemplary nonlimiting telomerase inhibitors include compounds that target, decrease, or inhibit the activity of telomerase, such as compounds that inhibit the telomerase receptor, such as telomestatin.

Exemplary nonlimiting proteasome inhibitors include compounds that target, decrease, or inhibit the activity of the proteasome including, but not limited to, bortezomid.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, I-β-D-arabinofuransylcytosine (ara-c), and bisulfan; and ALK inhibitors, which are compounds which target, decrease, or inhibit anaplastic lymphoma kinase.

Exemplary nonlimiting Flt-3 inhibitors include PKC412, midostaurin, a staurosporine derivative, SU11248, and MLN518.

Exemplary nonlimiting HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino, 17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidine-amine derivatives, such as imatinib, SU101, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Axl receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, Cl-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a Compound of the Disclosure, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

Other examples of second therapeutic agents, one or more of which a Compound of the Disclosure also can be combined, include, but are not limited to: a treatment for Alzheimer's Disease, such as donepezil and rivastigmine; a treatment for Parkinson's Disease, such as L-DOPA/carbidopa, entacapone, ropinrole, pramipexole, bromocriptine, pergolide, trihexephendyl, and amantadine; an agent for treating multiple sclerosis (MS) such as beta interferon (e.g., AVONEX® and REBIF®), glatiramer acetate, and mitoxantrone; a treatment for asthma, such as albuterol and montelukast; an agent for treating schizophrenia, such as zyprexa, risperdal, seroquel, and haloperidol; an anti-inflammatory agent, such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor, such as an acetylcholinesterase inhibitor, an MAO inhibitor, an interferon, an anti-convulsant, an ion channel blocker, riluzole, or an anti-Parkinson's agent; an agent for treating cardiovascular disease, such as a beta-blocker, an ACE inhibitor, a diuretic, a nitrate, a calcium channel blocker, or a statin; an agent for treating liver disease, such as a corticosteroid, cholestyramine, an interferon, and an anti-viral agent; an agent for treating blood disorders, such as a corticosteroid, an anti-leukemic agent, or a growth factor; or an agent for treating immunodeficiency disorders, such as gamma globulin.

The above-mentioned second therapeutically active agents, one or more of which can be used in combination with a Compound of the Disclosure, are prepared and administered as described in the art.

Compounds of the Disclosure typically are administered in admixture with a pharmaceutical carrier selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compound of the Disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of the Disclosure can be readily combined with pharmaceutically acceptable carriers well-known in the art. Standard pharmaceutical carriers are described in Remington's Pharmaceutical Sciences, Mack Publishing Co., Easton, Pa., 19th ed. 1995. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration.

To facilitate an understanding of the present disclosure, a number of terms and phrases are defined below.

In the present disclosure, the term "halo" as used by itself or as part of another group refers to —Cl, —F, —Br, or —I.

In the present disclosure, the term "nitro" as used by itself or as part of another group refers to —$NO_2$.

In the present disclosure, the term "cyano" as used by itself or as part of another group refers to —CN.

In the present disclosure, the term "hydroxy" as used by itself or as part of another group refers to —OH.

In the present disclosure, the term "alkyl" as used by itself or as part of another group refers to unsubstituted straight- or branched-chain aliphatic hydrocarbons containing from one to twelve carbon atoms, i.e., $C_{1-12}$ alkyl, or the number of carbon atoms designated, e.g., a $C_1$ alkyl such as methyl, a $C_2$ alkyl such as ethyl, a $C_3$ alkyl such as propyl or isopropyl, a $C_{1-3}$ alkyl such as methyl, ethyl, propyl, or isopropyl, and so on. In one embodiment, the alkyl is a $C_{1-10}$ alkyl. In another embodiment, the alkyl is a $C_{1-6}$ alkyl. In another embodiment, the alkyl is a $C_{1-4}$ alkyl. In another embodiment, the alkyl is a straight chain $C_{1-10}$ alkyl. In another embodiment, the alkyl is a branched chain $C_{3-10}$ alkyl. In another embodiment, the alkyl is a straight chain $C_{1-6}$ alkyl. In another embodiment, the alkyl is a branched chain $C_{3-6}$ alkyl. In another embodiment, the alkyl is a straight chain $C_{1-4}$ alkyl. In another embodiment, the alkyl is a branched chain $C_{3-4}$ alkyl. In another embodiment, the alkyl is a straight or branched chain $C_{3-4}$ alkyl. Non-limiting exemplary $C_{1-10}$ alkyl groups include methyl, ethyl, propyl, isopropyl, butyl, sec-butyl, tert-butyl, iso-butyl, 3-pentyl, hexyl, heptyl, octyl, nonyl, and decyl. Non-limiting exemplary $C_{1-4}$ alkyl groups include methyl, ethyl, propyl, isopropyl, butyl, sec-butyl, tert-butyl, and iso-butyl.

In the present disclosure, the term "optionally substituted alkyl" as used by itself or as part of another group refers to an alkyl that is either unsubstituted or substituted with one, two, or three substituents independently selected from the group consisting of nitro, haloalkoxy, aryloxy, aralkyloxy, alkylthio, sulfonamido, alkylcarbonyl, arylcarbonyl, alkylsulfonyl, arylsulfonyl, carboxy, carboxyalkyl, and alkylcarbonyloxy. In one embodiment, the optionally substituted alkyl is substituted with two substituents. In another embodiment, the optionally substituted alkyl is substituted with one substituent. In another embodiment, the optionally substituted alkyl is unsubstituted. Non-limiting exemplary substituted alkyl groups include —$CH_2CH_2NO_2$, —$CH_2SO_2CH_3$, $CH_2CH_2SO_2CH_3$, —$CH_2CH_2CO_2H$, —$CH_2SCH_3$, —$CH_2CH_2SO_2CH_3$, —$CH_2CH_2COPh$, and —$CH_2OC(=O)CH_3$.

In the present disclosure, the term "cycloalkyl" as used by itself or as part of another group refers to unsubstituted saturated or partially unsaturated, e.g., containing one or two double bonds, cyclic aliphatic hydrocarbons containing one to three rings having from three to twelve carbon atoms, i.e., $C_{3-12}$ cycloalkyl, or the number of carbons designated. In one embodiment, the cycloalkyl has two rings. In another embodiment, the cycloalkyl has one ring. In another embodiment, the cycloalkyl is saturated. In another embodiment, the cycloalkyl is unsaturated. In another embodiment, the cycloalkyl is a $C_{3-8}$ cycloalkyl. In another embodiment, the cycloalkyl is a $C_{3-6}$ cycloalkyl. The term "cycloalkyl" is meant to include groups wherein a ring —$CH_2$— is replaced with a —C(=O)—. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, cyclopentenyl, and cyclopentanone.

In the present disclosure, the term "optionally substituted cycloalkyl" as used by itself or as part of another group refers to a cycloalkyl that is either unsubstituted or substituted with one, two, or three substituents independently selected from the group consisting of halo, nitro, cyano, hydroxy, alkylcarbonyloxy, cycloalkylcarbonyloxy, amino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, (heterocyclo)alkyl, —OC(=O)-amino, —N($R^{19a}$)C(=O)—$R^{19b}$, and —N($R^{20a}$)$SO_2$—$R^{20b}$, wherein $R^{19a}$ is selected from the group consisting of hydrogen and alkyl, $R^{19b}$ is selected from the group consisting of amino, alkoxy, alkyl, and optionally substituted aryl, $R^{20a}$ is selected from the group consisting of hydrogen and alkyl, and $R^{20b}$ is selected from the group consisting of amino, alkyl, and optionally substituted aryl. The term optionally substituted cycloalkyl includes cycloalkyl groups having a fused optionally substituted aryl, e.g., phenyl, or fused optionally substituted heteroaryl, e.g., pyridyl. An optionally substituted cycloalkyl having a fused optionally substituted aryl or fused optionally substituted heteroaryl group may be attached to the remainder of the molecule at any available carbon atom on the cycloalkyl ring. In one embodiment, the optionally substituted cycloalkyl is substituted with two substituents. In another embodiment, the optionally substituted cycloalkyl is substituted with one substituent. In another embodiment, the optionally substituted cycloalkyl is unsubstituted.

In the present disclosure, the term "aryl" as used by itself or as part of another group refers to unsubstituted monocyclic or bicyclic aromatic ring systems having from six to fourteen carbon atoms, i.e., a $C_{6-14}$ aryl. Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is phenyl or naphthyl.

In the present disclosure, the term "optionally substituted aryl" as used herein by itself or as part of another group refers to an aryl that is either unsubstituted or substituted with one to five substituents independently selected from the group consisting of halo, nitro, cyano, hydroxy, amino, alkylamino, dialkylamino, optionally substituted alkyl, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, haloalkylsulfonyl cycloalkylsulfonyl, (cycloalkyl)alkylsulfonyl, arylsulfonyl, heteroarylsulfonyl, heterocyclosulfonyl, carboxy, carboxyalkyl, optionally substituted cycloalkyl, alkenyl, alkynyl, optionally substituted aryl, optionally substituted heteroaryl, optionally substituted heterocyclo, alkoxycarbonyl, alkoxyalkyl, (amino)alkyl, (carboxamido)alkyl, and (heterocyclo)alkyl.

In one embodiment, the optionally substituted aryl is an optionally substituted phenyl. In another embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. In another embodiment, the optionally substituted phenyl is unsubstituted. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, 3-chloro-4-fluorophenyl, 4-(pyridin-4-ylsulfonyl) phenyl The term optionally substituted aryl includes phenyl groups having a fused optionally substituted cycloalkyl or fused optionally substituted heterocyclo group. An optionally substituted phenyl having a fused optionally substituted cycloalkyl or fused optionally substituted heterocyclo group may be attached to the remainder of the molecule at any available carbon atom on the phenyl ring. Non-limiting examples include:

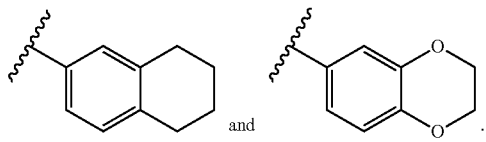 [SMILES: *c1ccc2c(c1)CCCC2 ; *c1ccc2c(c1)OCCO2]

In the present disclosure, the term "alkenyl" as used by itself or as part of another group refers to an alkyl containing one, two or three carbon-to-carbon double bonds. In one embodiment, the alkenyl has one carbon-to-carbon double bond. In another embodiment, the alkenyl is a $C_{2-6}$ alkenyl. In another embodiment, the alkenyl is a $C_{2-4}$ alkenyl. Non-limiting exemplary alkenyl groups include ethenyl, propenyl, isopropenyl, butenyl, sec-butenyl, pentenyl, and hexenyl.

In the present disclosure, the term "optionally substituted alkenyl" as used herein by itself or as part of another group refers to an alkenyl that is either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, heteroaryl, and optionally substituted heterocyclo.

In the present disclosure, the term "alkynyl" as used by itself or as part of another group refers to an alkyl containing one to three carbon-to-carbon triple bonds. In one embodiment, the alkynyl has one carbon-to-carbon triple bond. In another embodiment, the alkynyl is a $C_{2-6}$ alkynyl. In another embodiment, the alkynyl is a $C_{2-4}$ alkynyl. Non-limiting exemplary alkynyl groups include ethynyl, propynyl, butynyl, 2-butynyl, pentynyl, and hexynyl groups.

In the present disclosure, the term "optionally substituted alkynyl" as used herein by itself or as part refers to an alkynyl that is either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, cycloalkyl, alkenyl, alkynyl, optionally substituted aryl, optionally substituted heteroaryl, and heterocyclo.

In the present disclosure, the term "haloalkyl" as used by itself or as part of another group refers to an alkyl substituted by one or more fluorine, chlorine, bromine and/or iodine atoms. In one embodiment, the alkyl group is substituted by one, two, or three fluorine and/or chlorine atoms. In another embodiment, the haloalkyl group is a $C_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

In the present disclosure, the term "hydroxyalkyl" as used by itself or as part of another group refers to an alkyl substituted with one, two, or three hydroxy groups. In one embodiment, the hydroxyalkyl is a monohydroxyalkyl, i.e., a hydroxyalkyl substituted with one hydroxy group. In another embodiment, the hydroxyalkyl is a dihydroxyalkyl, i.e., a hydroxyalkyl substituted with two hydroxy groups. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

In the present disclosure, the term "(cycloalkyl)alkyl," as used by itself or as part of another group refers to an alkyl substituted with an optionally substituted cycloalkyl. In one embodiment, the (cycloalkyl) alkyl, is a "($C_{3-6}$ cycloalkyl) $C_{1-4}$ alkyl," i.e., a $C_{1-4}$ alkyl substituted with an optionally substituted $C_{3-6}$ cycloalkyl. Non-limiting exemplary (cycloalkyl) alkyl groups include:

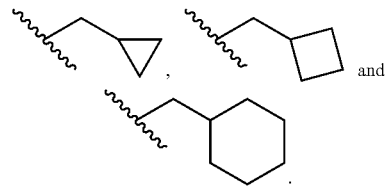

In the present disclosure, the term "alkylsulfonyl" as used by itself or as part of another group refers to a sulfonyl, i.e., $-SO_2-$, substituted with an optionally substituted alkyl. A non-limiting exemplary alkylsulfonyl group is $-SO_2CH_3$.

In the present disclosure, the term "haloalkylsulfonyl" as used by itself or as part of another group refers to a sulfonyl, i.e., $-SO_2-$, substituted with a haloalkyl. A non-limiting exemplary alkylsulfonyl group is $-SO_2CF_3$.

In the present disclosure, the term "cycloalkylsulfonyl" as used by itself or as part of another group refers to a sulfonyl, i.e., $-SO_2-$, substituted with an optionally substituted cycloalkyl. Non-limiting exemplary alkylsulfonyl group include $-SO_2$-cyclopropyl and $-SO_2$-cyclopenyl.

In the present disclosure, the term "(cycloalkyl)alkylsulfonyl" as used by itself or as part of another group refers to a sulfonyl, i.e., $-SO_2-$, substituted with a (cycloalkyl)alkyl. Non-limiting exemplary (cycloalkyl)alkylsulfonyl groups include:

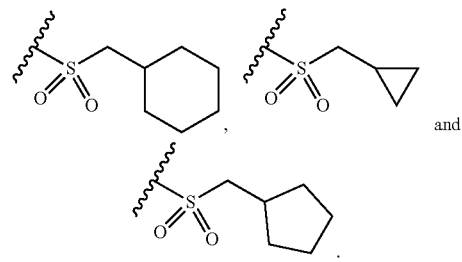

In the present disclosure, the term "arylsulfonyl" as used by itself or as part of another group refers to a sulfonyl, i.e., $-SO_2-$, substituted with an optionally substituted aryl. A non-limiting exemplary arylsulfonyl group is $-SO_2Ph$.

In the present disclosure, the term "heteroarylsulfonyl" as used by itself or as part of another group refers to a sulfonyl, i.e., $-SO_2-$, substituted with an optionally substituted heteroaryl group. Non-limiting exemplary heteroarylsulfonyl groups include:

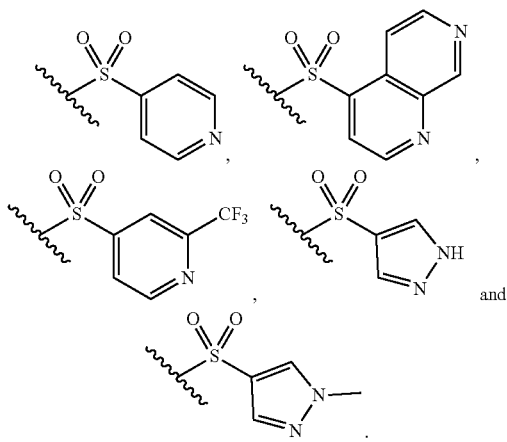

In the present disclosure, the term "heterocyclosulfonyl" as used by itself or as part of another group refers to a sulfonyl, i.e., —SO$_2$—, substituted with an optionally substituted heterocyclo group. A non-limiting exemplary heterocyclosulfonyl group is:

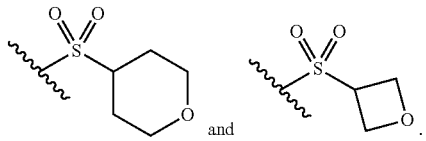 [SMILES: *S(=O)(=O)C1CCOCC1 ; *S(=O)(=O)C1COC1]

In the present disclosure, the term "sulfonamido" as used by itself or as part of another group refers to a radical of the formula —SO$_2$NR$^{21a}$R$^{21b}$, wherein R$^{21a}$ and R$^{21b}$ are each independently selected from the group consisting of hydrogen, optionally substituted alkyl, and optionally substituted aryl, or R$^{21a}$ and R$^{21b}$ taken together with the nitrogen to which they are attached from a 3- to 8-membered heterocyclo group. Non-limiting exemplary sulfonamido groups include —SO$_2$NH$_2$, —SO$_2$N(H)CH$_3$, —SO$_2$N(CH$_3$)$_2$, and —SO$_2$N(H)Ph.

In the present disclosure, the term "alkoxy" as used by itself or as part of another group refers to an optionally substituted alkyl, optionally substituted cycloalkyl, optionally substituted alkenyl, or optionally substituted alkynyl attached to a terminal oxygen atom. In one embodiment, the alkoxy is an optionally substituted alkyl attached to a terminal oxygen atom. In one embodiment, the alkoxy group is a C$_{1-6}$ alkyl attached to a terminal oxygen atom. In another embodiment, the alkoxy group is a C$_{1-4}$ alkyl attached to a terminal oxygen atom. Non-limiting exemplary alkoxy groups include methoxy, ethoxy, tert-butoxy, and —OCH$_2$SO$_2$CH$_3$.

In the present disclosure, the term "alkylthio" as used by itself or as part of another group refers to an optionally substituted alkyl attached to a terminal sulfur atom. In one embodiment, the alkylthio group is a C$_{1-4}$ alkylthio group. Non-limiting exemplary alkylthio groups include —SCH$_3$ and —SCH$_2$CH$_3$.

In the present disclosure, the term "alkoxyalkyl" as used by itself or as part of another group refers to an optionally substituted alkyl substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

In the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

In the present disclosure, the term "aryloxy" as used by itself or as part of another group refers to an optionally substituted aryl attached to a terminal oxygen atom. A non-limiting exemplary aryloxy group is PhO—.

In the present disclosure, the term "aralkyloxy" as used by itself or as part of another group refers to an aralkyl attached to a terminal oxygen atom. Non-limiting exemplary aralkyloxy groups include PhCH$_2$O— and PhCH$_2$CH$_2$O—.

In the present disclosure, the term "heteroaryl" refers to unsubstituted monocyclic and bicyclic aromatic ring systems having 5 to 14 ring atoms, i.e., a 5- to 14-membered heteroaryl, wherein at least one carbon atom of one of the rings is replaced with a heteroatom independently selected from the group consisting of oxygen, nitrogen and sulfur. In one embodiment, the heteroaryl contains 1, 2, 3, or 4 heteroatoms independently selected from the group consisting of oxygen, nitrogen and sulfur. In one embodiment, the heteroaryl has three heteroatoms. In another embodiment, the heteroaryl has two heteroatoms. In another embodiment, the heteroaryl has one heteroatom. In another embodiment, the heteroaryl is a 5- to 10-membered heteroaryl. In another embodiment, the heteroaryl is a 5- or 6-membered heteroaryl. In another embodiment, the heteroaryl has 5 ring atoms, e.g., thienyl, a 5-membered heteroaryl having four carbon atoms and one sulfur atom. In another embodiment, the heteroaryl has 6 ring atoms, e.g., pyridyl, a 6-membered heteroaryl having five carbon atoms and one nitrogen atom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is selected from the group consisting of thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl), isoxazolyl (e.g., isoxazol-3-yl, isoxazol-4-yl, and isoxazol-5-yl), and indazolyl (e.g., 1H-indazol-3-yl). The term "heteroaryl" is also meant to include possible N-oxides. A non-limiting exemplary N-oxide is pyridyl N-oxide.

In one embodiment, the heteroaryl is a 5- or 6-membered heteroaryl. In one embodiment, the heteroaryl is a 5-membered heteroaryl, i.e., the heteroaryl is a monocyclic aromatic ring system having 5 ring atoms wherein at least one carbon atom of the ring is replaced with a heteroatom independently selected from nitrogen, oxygen, and sulfur. Non-limiting exemplary 5-membered heteroaryl groups include thienyl, furyl, pyrrolyl, oxazolyl, pyrazolyl, imidazolyl, thiazolyl, isothiazolyl, and isoxazolyl. In another embodiment, the heteroaryl is a 6-membered heteroaryl, e.g., the heteroaryl is a monocyclic aromatic ring system having 6 ring atoms wherein at least one carbon atom of the ring is replaced with a nitrogen atom. Non-limiting exemplary 6-membered heteroaryl groups include pyridyl, pyrazinyl, pyrimidinyl, and pyridazinyl.

In the present disclosure, the term "optionally substituted heteroaryl" as used by itself or as part of another group refers to a heteroaryl that is either unsubstituted or substituted with one two, three, or four substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, haloalkylsulfonyl cycloalkylsulfonyl, (cycloalkyl)alkylsulfonyl, arylsulfonyl, heteroarylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, and (heterocyclo)alkyl. In one embodiment, the optionally substituted heteroaryl has one substituent. In another embodiment, the optionally substituted heteroaryl is unsubstituted. Any available carbon or nitrogen atom can be substituted. The term optionally substituted heteroaryl includes heteroaryl groups having a fused optionally substituted cycloalkyl or fused optionally substituted heterocyclo group. An optionally substituted heteroaryl having a fused optionally substituted cycloalkyl or fused optionally substituted heterocyclo group may be attached to the remainder of the molecule at any available carbon atom on the heteroaryl ring.

In the present disclosure, the term "heterocyclo" as used by itself or as part of another group refers to unsubstituted saturated and partially unsaturated, e.g., containing one or two double bonds, cyclic groups containing one, two, or three rings having from three to fourteen ring members, i.e., a 3- to 14-membered heterocyclo, wherein at least one carbon atom of one of the rings is replaced with a heteroatom. Each heteroatom is independently selected from the group consisting of oxygen, sulfur, including sulfoxide and sulfone, and/or nitrogen atoms, which can be oxidized or quaternized. The term "heterocyclo" includes groups wherein a ring —CH$_2$— is replaced with a —C(=O)—, for example, cyclic ureido groups such as 2-imidazolidinone and cyclic amide groups such as β-lactam, γ-lactam, δ-lactam, ε-lactam, and piperazin-2-one. The term "heterocyclo" also includes groups having fused optionally substituted aryl groups, e.g., indolinyl or chroman-4-yl. In one embodiment, the heterocyclo group is a C$_{4-6}$ heterocyclo, i.e., a 4-, 5- or 6-membered cyclic group, containing one ring and one or two oxygen and/or nitrogen atoms. In one embodiment, the heterocyclo group is a C$_{4-6}$ heterocyclo containing one ring and one nitrogen atom. The heterocyclo can be optionally linked to the rest of the molecule through any available carbon or nitrogen atom. Non-limiting exemplary heterocyclo groups include azetidinyl, dioxanyl, tetrahydropyranyl, 2-oxopyrrolidin-3-yl, piperazin-2-one, piperazine-2,6-dione, 2-imidazolidinone, piperidinyl, morpholinyl, piperazinyl, pyrrolidinyl, and indolinyl.

In the present disclosure, the term "optionally substituted heterocyclo" as used herein by itself or part of another group refers to a heterocyclo that is either unsubstituted or substituted with one, two, three, or four substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, cycloalkylcarbonyl, alkoxycarbonyl, CF$_3$C(=O)—, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, or (heterocyclo)alkyl. Substitution may occur on any available carbon or nitrogen atom, or both. Non-limiting exemplary substituted heterocyclo groups include:

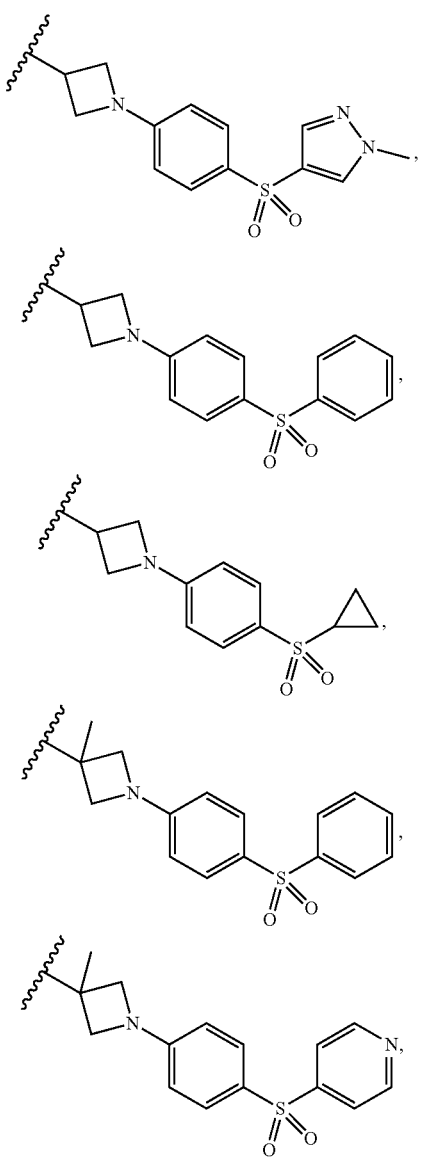

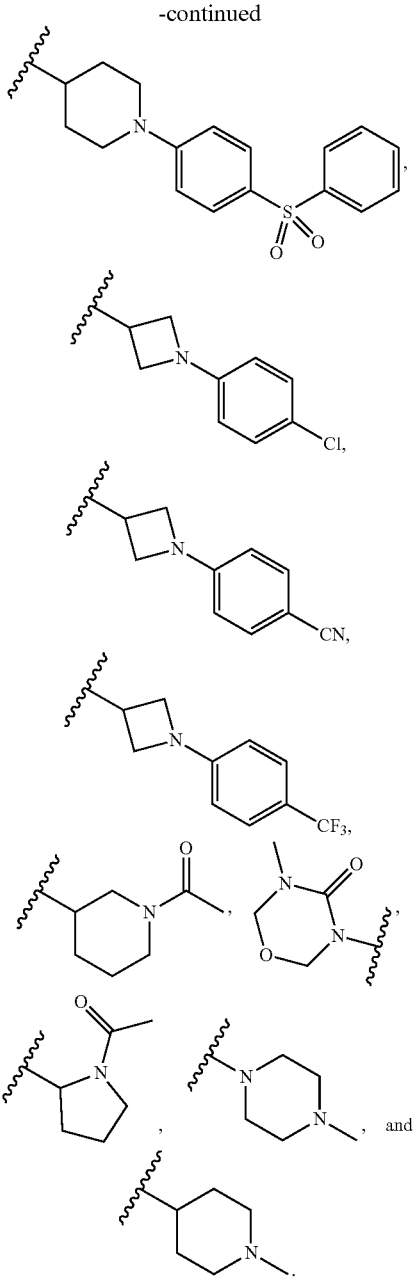

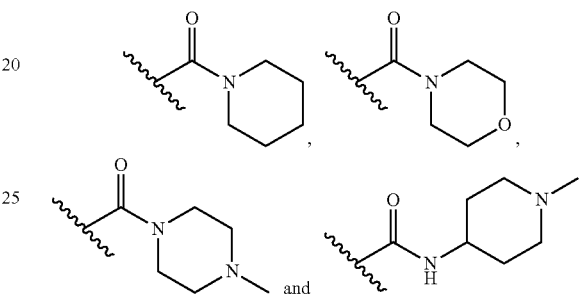

In the present disclosure, the term "amino" as used by itself or as part of another group refers to a radical of the formula —NR$^{22a}$R$^{22b}$, wherein R$^{22a}$ and R$^{22b}$ are each independently selected from the group consisting of hydrogen, alkyl, aralkyl, hydroxyalkyl, optionally substituted cycloalkyl, optionally substituted aryl, optionally substituted heterocyclo, and optionally substituted heteroaryl, or R$^{22a}$ and R$^{22b}$ are taken together to form a 3- to 8-membered optionally substituted heterocyclo. Non-limiting exemplary amino groups include —NH$_2$ and —N(H)(CH$_3$).

In the present disclosure, the term "(amino)alkyl" as used by itself or as part of another group refers to an alkyl substituted with an amino. Non-limiting exemplary (amino)alkyl groups include —CH$_2$CH$_2$NH$_2$, and —CH$_2$CH$_2$N(H)CH$_3$, —CH$_2$CH$_2$N(CH$_3$)$_2$, and —CH$_2$N(H)-cyclopropyl.

In the present disclosure, the term "carboxamido" as used by itself or as part of another group refers to a radical of the formula —C(=O)NR$^{23a}$R$^{23b}$, wherein R$^{23a}$ and R$^{23b}$ are each independently selected from the group consisting of hydrogen, optionally substituted alkyl, hydroxyalkyl, optionally substituted cycloalkyl, optionally substituted aryl, optionally substituted heterocyclo, and optionally substituted heteroaryl, or R$^{23a}$ and R$^{23b}$ taken together with the nitrogen to which they are attached form a 3- to 8-membered optionally substituted heterocyclo group. In one embodiment, R$^{23a}$ and R$^{23b}$ are each independently hydrogen or optionally substituted alkyl. In one embodiment, R$^{23a}$ and R$^{23b}$ are taken together to taken together with the nitrogen to which they are attached form a 3- to 8-membered optionally substituted heterocyclo group. Non-limiting exemplary carboxamido groups include —CONH$_2$, —CON(H)CH$_3$, —CON(CH$_3$)$_2$, —CON(H)Ph, In the present disclosure, the term "alkylcarbonyl" as used by itself or as part of another group refers to a carbonyl group, i.e., —C(=O)—, substituted with an alkyl. Non-limiting exemplary alkylcarbonyl groups include —C(=O)CH$_3$ and —C(=O)CH$_2$CH$_2$CH$_2$CH$_3$.

In the present disclosure, the term "cycloalkylcarbonyl" as used by itself or as part of another group refers to a carbonyl group, i.e., —C(=O)—, substituted with a cycloalkyl. A non-limiting exemplary cycloalkylcarbonyl group is —C(=O)-cyclopropyl.

In the present disclosure, the term "arylcarbonyl" as used by itself or as part of another group refers to a carbonyl group, i.e., —C(=O)—, substituted with an optionally substituted aryl. A non-limiting exemplary arylcarbonyl group is —COPh.

In the present disclosure, the term "alkoxycarbonyl" as used by itself or as part of another group refers to a carbonyl group, i.e., —C(=O)—, substituted with an alkoxy. In one embodiment, the alkoxy is a C$_{1-4}$ alkoxy. Non-limiting exemplary alkoxycarbonyl groups include —C(=O)OMe, —C(=O)OEt, and —C(=O)OtBu.

In the present disclosure, the term "(alkoxycarbonyl)alkyl" as used by itself or as part of another group refers to an alkyl substituted by an alkoxycarbonyl group. Non-limiting exemplary (alkoxycarbonyl)alkyl groups include —CH$_2$C(=O)OMe, —CH$_2$C(=O)OEt, and —CH$_2$C(=O)OtBu.

In the present disclosure, the term "carboxy" as used by itself or as part of another group refers to a radical of the formula —CO$_2$H.

In the present disclosure, the term "carboxyalkyl" as used by itself or as part of another group refers to an alkyl substituted with a —CO$_2$H. A non-limiting exemplary carboxyalkyl group is —CH$_2$CO$_2$H.

In the present disclosure, the term "aralkyl" as used by itself or as part of another group refers to an alkyl substituted with one, two, or three optionally substituted aryl groups. In one embodiment, aralkyl is a $C_{1-4}$ alkyl substituted with one optionally substituted $C_5$ or $C_6$ aryl group. In another embodiment, the aralkyl is a $C_1$ alkyl substituted with one optionally substituted aryl group. In another embodiment, the aralkyl is a $C_2$ alkyl substituted with one optionally substituted aryl group. In another embodiment, the aralkyl is a $C_3$ alkyl substituted with one optionally substituted aryl group. In one embodiment, the aralkyl is a $C_1$ or $C_2$ alkyl substituted with one optionally substituted phenyl group. Non-limiting exemplary aralkyl groups include benzyl, phenethyl, —CHPh$_2$, —CH(CH$_3$)Ph, —CH$_2$(4-F-Ph), —CH$_2$(4-Me-Ph), —CH$_2$(4-CF$_3$-Ph), and —CH(4-F-Ph)$_2$.

In the present disclosure, the term "(heterocyclo)alkyl" as used by itself or part of another group refers to an alkyl substituted with an optionally substituted heterocyclo group. In one embodiment, the (heterocyclo)alkyl is a $C_{1-4}$ alkyl substituted with one optionally substituted heterocyclo group. Non-limiting exemplary (heterocyclo)alkyl groups include:

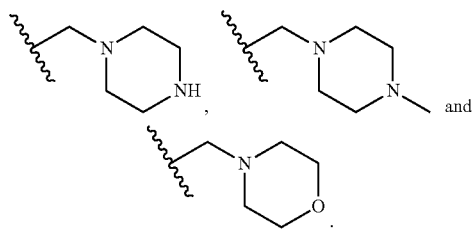

In the present disclosure, the term "(heteroaryl)alkyl" as used by itself or part of another group refers to an alkyl substituted with an optionally substituted heteroaryl group. In one embodiment, the (heteroaryl)alkyl is a $C_{1-4}$ alkyl substituted with one optionally substituted heteroaryl group. In another embodiment, the (heteroaryl)alkyl is a $C_1$ alkyl substituted with one optionally substituted heteroaryl group Non-limiting exemplary (heteroaryl)alkyl groups include:

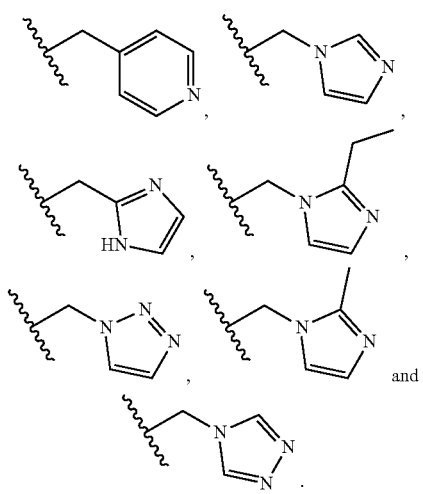

In the present disclosure, the term "(carboxamido)alkyl" as used by itself or as part of another group refers to an alkyl substituted with one or two carboxamido groups. In one embodiment, the (carboxamido)alkyl is a $C_{1-4}$ alkyl substituted with one carboxamido group, i.e., a (carboxamido)$C_{1-4}$ alkyl. In another embodiment, the (carboxamido)alkyl is a $C_{1-4}$ alkyl substituted with two carboxamido groups. Non-limiting exemplary (carboxamido)alkyl groups include —CH$_2$CONH$_2$, —C(H)CH$_3$—CONH$_2$, and —CH$_2$CON(H)CH$_3$.

In the present disclosure, the term "(aryloxy)alkyl" as used by itself or as part of another group refers to an alkyl substituted with an aryloxy group. In one embodiment, the "(aryloxy)alkyl" is a $C_{1-4}$ alkyl substituted with an aryloxy. In one embodiment, the "(aryloxy)alkyl" is a $C_{2-4}$ alkyl substituted with an aryloxy. Non-limiting exemplary (aryloxy)alkyl groups include —CH$_2$CH$_2$OPh and —CH$_2$CH$_2$CH$_2$OPh.

In the present disclosure, the term "alkylcarbonyloxy" as used by itself or as part of another group refers to an oxy, e.g., —O—, substituted with an alkylcarbonyl group. Non-limiting exemplary "alkylcarbonyloxy" groups include —OC(=O)CH$_2$CH$_3$, —OC(=O)CH$_3$, i.e., acetoxy, —OC(=O)CH$_2$CH$_2$CH$_3$, and —OC(=O)CH(CH$_3$)$_2$.

In the present disclosure, the term "cycloalkylcarbonyloxy" as used by itself or as part of another group refers to an oxy, e.g., —O—, substituted with an cycloalkylcarbonyl group. Non-limiting exemplary "cycloalkylcarbonyloxy" groups include —OC(=O)-cyclopropyl and —OC(=O)-cyclopenyl.

The term "menin inhibitor" or "inhibitor of menin" as used herein refers to a compound that disrupts, e.g., inhibits, the menin-MLL fusion protein interaction.

The term "a disease or condition wherein inhibition of menin provides a benefit" pertains to a disease or condition in which menin and/or the interaction of menin with a menin-interacting protein is important or necessary, e.g., for the onset, progress, or expression of that disease or condition, or a disease or a condition which is known to be treated by a menin inhibitor. Examples of such conditions include, but are not limited to, a cancer, a chronic autoimmune disease, an inflammatory disease, a proliferative disease, sepsis, and a viral infection. One of ordinary skill in the art is readily able to determine whether a compound treats a disease or condition mediated by menin for any particular cell type, for example, by assays which conveniently can be used to assess the activity of particular compounds.

The term "second therapeutic agent" refers to a therapeutic agent different from a Compound of the Disclosure and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, Compounds of the Disclosure are menin inhibitors and can be used in treating diseases and conditions wherein menin inhibition provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a Compound of the Disclosure to an individual in need of such treatment.

Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce menin interactions in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a Compound of the Disclosure can be administered at the same time or sequentially in any order at different points in time as a second therapeutic agent. A Compound of the Disclosure and the second therapeutic agent can be administered separately, in any appropriate form and by any suitable route. When a Compound of the Disclosure and the second therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a Compound of the Disclosure and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart.

The use of the terms "a", "an", "the", and similar referents in the context of this disclosure (especially in the context of the claims) are to be construed to cover both the singular and the plural, unless otherwise indicated. Recitation of ranges of values herein are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

The term "about," as used herein, includes the recited number ±10%. Thus, "about 10" means 9 to 11.

EXAMPLES

Example 1

Synthesis of methyl ((1S,2R)-2-((S)-1-(1-((1-(4-((3-acrylamidophenyl)sulfonyl)phenyl)azetidin-3-yl)methyl)piperidin-4-yl)-2-(2-ethyl-1H-imidazol-1-yl)-1-(3-fluorophenyl)ethyl)cyclopentyl) (Cpd. No. 7)

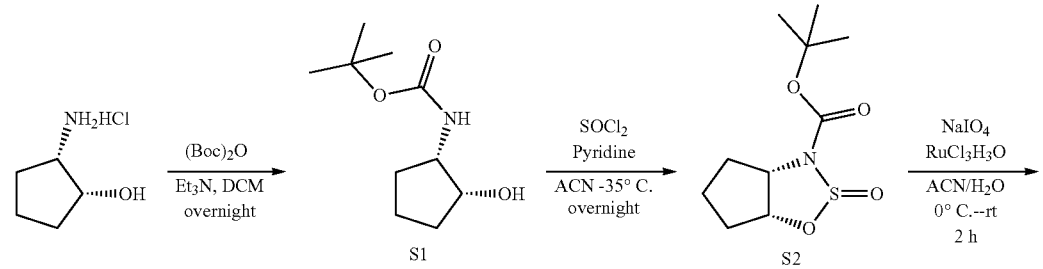

-continued
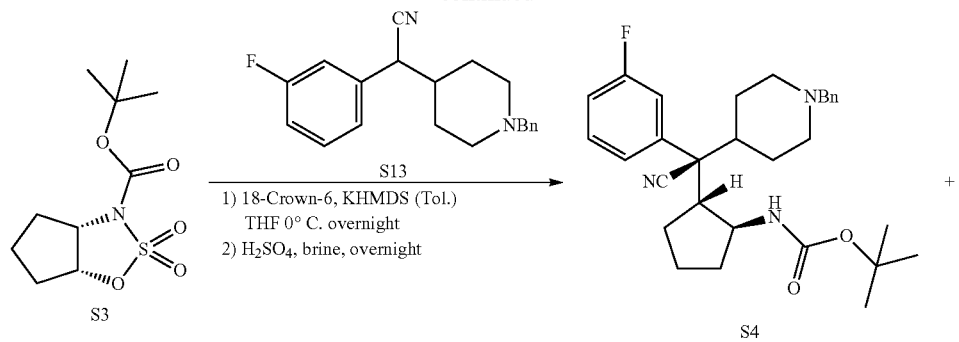
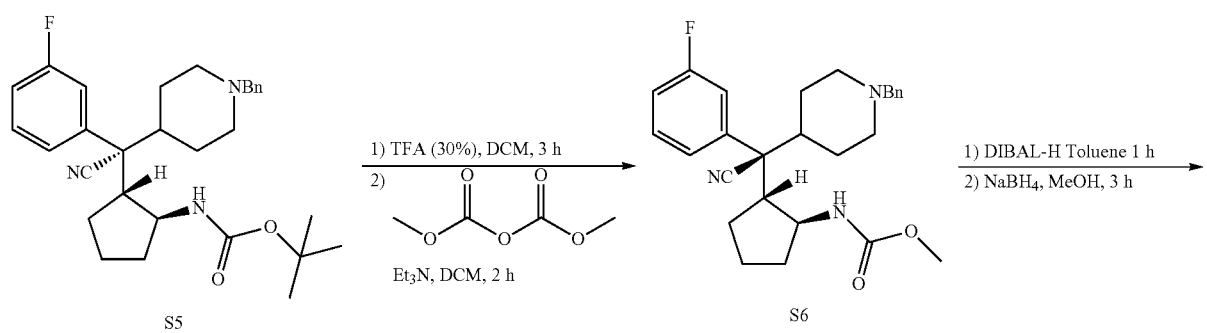
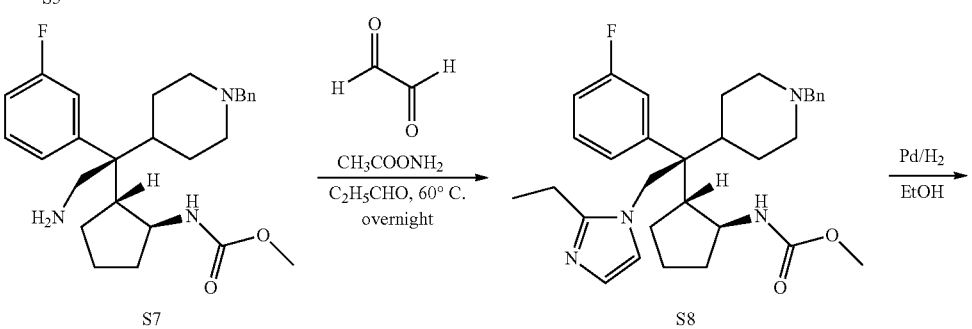
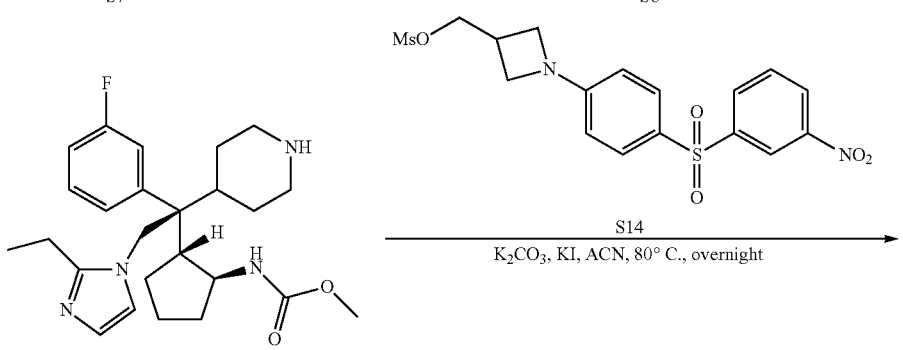
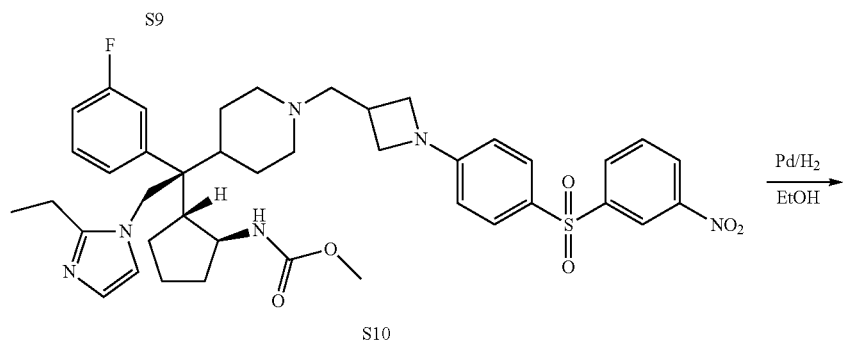

-continued

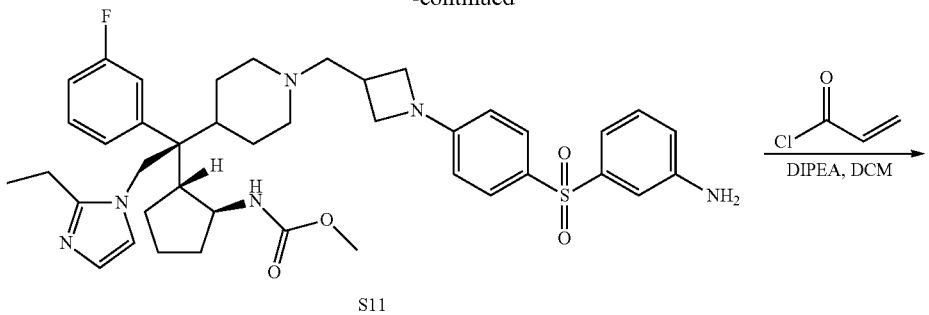

S11

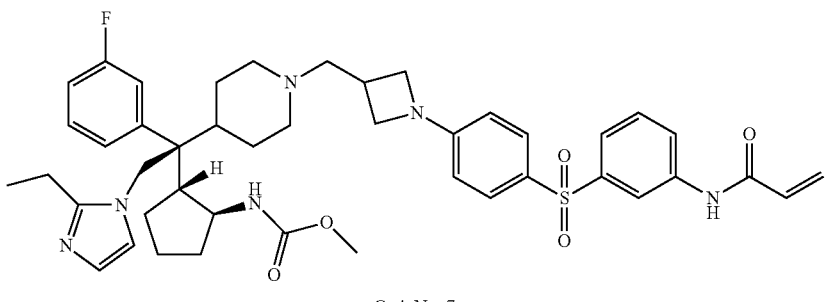

Cpd. No. 7

Synthesis of tert-butyl ((1S,2R)-2-hydroxycyclopentyl)carbamate (S1)

Triethylamine (4.46 mL, 31.98 mmol) was added to a solution of (1R,2S)-2-aminocyclopentanol hydrochloride (2.2 g, 15.99 mmol) in DCM (22 mL). The solution was cooled to 0° C. then Boc$_2$O (3.84 g, 17.59 mmol) was added and the reaction was allowed to warm to RT. After overnight, H$_2$O and DCM were added and stirred until the solid disappeared then the aqueous layer was extracted three time with DCM, concentrated and purified by column chromatography (DCM/EtOAc gradient) to produce 3.2 g of S1.

Synthesis of tert-butyl (3aS,6aR)-tetrahydrocyclopenta[d][1,2,3]oxathiazole-3(3aH)-carboxylate 2-oxide (S2)

A solution of S1 (3.2 g, 15.9 mmol) in 15 mL of CH$_3$CN was added to a solution, at –35° C., of thionyl chloride (1.45 mL, 19.9 mmol) in dry CH$_3$CN (25 mL). Next, pyridine (3.86 mL, 47.7 mmol) was slowly added and the reaction was allowed to slowly warm to RT. After overnight, the solvent was removed; water and EtOAc were added and stirred for 20 minutes. The organic layer was separated and the aqueous layer was extracted three more times with EtOAc, dried over Na$_2$SO$_4$, filtered, concentrated, and purified by column chromatography (DCM/EtOAc gradient) to produce 2.74 g (70%) of S2.

Synthesis of tert-butyl (3aS,6aR)-tetrahydrocyclopenta[d][1,2,3]oxathiazole-3(3aH)-carboxylate 2,2-dioxide (S3)

S2 (2.74 g, 11.08 mmol) was dissolved in CH$_3$CN (18 mL) and H$_2$O (18 mL) and cooled to 0° C. RuCl$_3$.3H$_2$O (11 mg) was added followed by addition of NaIO$_4$ (4.74 g, 22.16 mmol) in portions. The mixture was stirred at RT for 2 hours (Check TLC to make sure the S2 is consumed). After the reaction was complete, the aqueous layer was extracted three times with diethyl ether, dried over Na$_2$SO$_4$, filtered, concentrated, and purified by column chromatography (DCM/EtOAc gradient) to produce 2.76 g (95%) of S3 as a white solid.

Synthesis of tert-butyl ((1S,2R)-2-((S)-(1-benzylpiperidin-4-yl)(cyano)(3-fluorophenyl)methyl)cyclopentyl)carbamate (S4) and tert-butyl ((1S,2R)-2-((R)-(1-benzylpiperidin-4-yl)(cyano)(3-fluorophenyl)methyl)cyclopentyl)carbamate (S5)

Compound S13 (2.18 g, 7.07 mmol, 1 equiv), 18-Crown-6 (5.61 g, 21.21 mmol, 3 equiv), and S3 (5.58 g, 21.21 mmol, 3 equiv) were added to a dry RB-flask then covered with a kimwipe and put in a desiccator that was put under vacuum for 1-2 days. After the vacuuming step, the flask was removed from the desiccator and quickly capped with a septum and the system was vacuumed for another hour then put under N$_2$ atmosphere. The contents in the flask were then dissolved with 60 mL of freshly distilled THF (stir until all contents are completely dissolved). The solution was then briefly vacuumed then put under nitrogen atmosphere—this purging was repeated two more times. The reaction was cooled to 0° C., KHMDS (0.5M in toluene, 42.4 mL, 21.21 mmol) was added dropwise and then the reaction was allowed to warm to RT and left to proceed overnight. After overnight at RT, 1M H$_2$SO$_4$ (21 mL, 3 equiv) was added and the solution was stirred for 5 hr then EtOAc was added and the solution was slowly quenched with NaHCO$_3$, extracted three times, and concentrated to give crude mixture S4:S5. The crude was purified by column chromatograph using a gradient of DCM to EtOAc to produce 2.5 g (73%) of S4:S5 in a 1:1 mixture.

Synthesis of Methyl ((1S,2R)-2-((R)-(1-benzylpiperidin-4-yl)(cyano)(3-fluorophenyl)methyl)-2-methylcyclopentyl)carbamate (S6)

5 mL of trifluoroacetic acid was added to a solution of mixture of S4 and S5 (2.5 g, 5.08 mmol) in 12 mL of DCM. After stirring for 2 h at room temperature, the mixture was concentrated in vacuum, diluted with 50 mL of DCM again, basified with 30 mL of saturated aqueous NaHCO$_3$, extracted three times with DCM, dried over Na$_2$SO$_4$, filtered and concentrated to give 2 g of crude intermediate 2-((1R, 2S)-2-aminocyclopentyl)-2-(1-benzylpiperidin-4-yl)-2-(3-fluorophenyl)acetonitrile, which was used for next step without further purification. Triethylamine (1.42 mL, 10.22 mmol) was added to a solution of intermediate 2-((1R,2S)-2-aminocyclopentyl)-2-(1-benzylpiperidin-4-yl)-2-(3-fluorophenyl)acetonitrile (2 g, 5.11 mmol) in DCM (50 mL). The solution was cooled to 0° C. then dimethyl dicarbonate (0.66 mL, 6.13 mmol) was added and the reaction was allowed to warm to RT. After 2 h, H$_2$O and DCM were added, then the aqueous layer was extracted three time with DCM, concentrated to give crude mixture product. The mixture was separated by prep-HPLC to give 0.9 g (39%) of enantiopure product S6.

Synthesis of Methyl ((1S,2R)-2-((S)-2-amino-1-(1-benzylpiperidin-4-yl)-1-(3-fluorophenyl)ethyl) cyclopentyl)carbamate (S7)

To an ice cold solution of the intermediate S6 (300 mg, 0.67 mmol) in toluene (3 mL) was added diisobutylaluminiumhydride (25% in toluene, 2.24 mL) under argon. The mixture was then allowed to warm to room temperature and stirred for 20 min. The mixture was cooled to 0° C. and quenched by careful addition of IM aqueous NaOH (1 mL). The suspension was stirred for another 10 minutes, and filtered. The filtrate was extracted with ethyl acetate, dried over Na$_2$SO$_4$ and evaporated. The residue was dried in vacuum and then dissolved in methanol (10 mL). NaBH$_4$ (50 mg, 1.33 mmol) was added into the mixture, and the reaction mixture was stirred at room temperature overnight. The mixture was concentrated in vacuum and diluted with ethyl acetate and water. The mixture was extracted with ethyl acetate, dried (Na$_2$SO$_4$), and the solvent was evaporated to give the title compound (250 mg, 82%) without further purification.

Synthesis of Methyl ((1S,2R)-2-((S)-1-(1-benzylpiperidin-4-yl)-2-(2-ethyl-1H-imidazol-1-yl)-1-(3-fluorophenyl)ethyl) cyclopentyl)carbamate (S8)

NH$_4$Ac (116 mg, 1.54 mmol) was added to a solution of crude S7 (350 mg, 0.77 mmol), propionaldehyde (0.57 mL, 7.7 mmol), oxalaldehyde (0.18 mL, 1.54 mmol) in MeOH (5 mL) and stirred at 50° C. overnight. The crude product was purified by reverse phase prep-HPLC, and the pure product was lyophilized to give S8-TFA (300 mg, 73%) salt as white solid.

Synthesis of Methyl ((1S,2R)-2-((S)-2-(2-ethyl-1H-imidazol-1-yl)-1-(3-fluorophenyl)-1-(piperidin-4-yl) ethyl)cyclopentyl) Carbamate (S9)

Compound S8 (300 mg, 0.56 mmol) was dissolved in EtOH (10 mL) and the solution was vacuumed briefly then put under N$_2$ atmosphere—this was repeated 3 times. Pd/C (10% wt/wt, 60 mg) was quickly added to the solution that was vacuumed and put under N$_2$ atmosphere. The solution was briefly vacuumed to remove the N$_2$ atmosphere then put under H$_2$ atmosphere—this was repeated 3 times. After 2 h, the reaction was filtered through celite and concentrated to give 237 mg crude S9 (95% yield) that was used without further purification.

Synthesis of Methyl ((1S,2R)-2-((S)-2-(2-ethyl-1H-imidazol-1-yl)-1-(3-fluorophenyl)-1-(1-((1-(4-((3-nitrophenyl) sulfonyl)phenyl)azetidin-3-yl)methyl) piperidin-4-yl)ethyl) cyclopentyl)carbamate (S10)

To a solution of the intermediate S9 (27 mg, 0.06 mmol) in acetonitrile (2 mL) was added S14 (26 mg, 0.06 mmol), K$_2$CO$_3$ (17 mg, 0.12 mmol) and KI (1 mg, 0.006 mmol). The mixture was stirred at 80° C. overnight. Then, the mixture was extracted with ethyl acetate, washed with brine, dried (Na$_2$SO$_4$), and the solvent was evaporated. The residue was purified with pre-HPLC to give S10-TFA (30 mg, 71% yield) salt as white solid.

Synthesis of Methyl ((1S,2R)-2-((S)-1-(1-((1-(4-((3-aminophenyl)sulfonyl)phenyl) azetidin-3-yl)methyl) piperidin-4-yl)-2-(2-ethyl-1H-imidazol-1-yl)-1-(3-fluorophenyl) ethyl)cyclopentyl)carbamate (S11)

Compound S10 (30 mg, 0.38 mmol) was dissolved in EtOH (10 mL) and the solution was vacuumed briefly then put under N$_2$ atmosphere—this was repeated 3 times. Pd/C (10% wt/wt, 10 mg) was quickly added to the solution that was vacuumed and put under N$_2$ atmosphere. The solution was briefly vacuumed to remove the N$_2$ atmosphere then put under H$_2$ atmosphere—this was repeated 3 times. After 1 h, the reaction was filtered through celite and concentrated to give 26 mg crude S11 (90% yield) that was used without further purification.

Synthesis of Methyl ((1S,2R)-2-((S)-1-(1-((1-(4-((3-acrylamidophenyl)sulfonyl)phenyl) azetidin-3-yl) methyl)piperidin-4-yl)-2-(2-ethyl-1H-imidazol-1-yl)-1-(3-fluorophenyl)ethyl)cyclopentyl) carbamate (Cpd. No. 7)

N,N-Diisopropylethylamine (0.008 mL, 0.07 mmol) was added to a solution of intermediate S11 (25 mg, 0.035 mmol) in DCM (10 mL). The solution was cooled to 0° C. then acryloyl chloride (0.009 mL, 0.07 mmol) was added and the reaction was allowed to warm to RT. After 1 h, H$_2$O and DCM were added, then the aqueous layer was extracted three time with DCM, concentrated to give crude mixture product. The mixture was separated by prep-HPLC to give 20 mg (72%) of the title product.

Example 2
Synthesis of methyl ((1S,2R)-2-((S)-cyano(1-((1-(4-((1-((E)-4-(dimethylamino)but-2-enoyl)azetidin-3-yl) sulfonyl)phenyl)azetidin-3-yl)methyl)piperidin-4-yl)(3-fluorophenyl)methyl)cyclopentyl)carbamate (Cpd. No. 57)
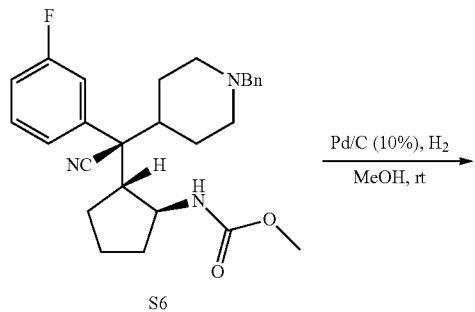
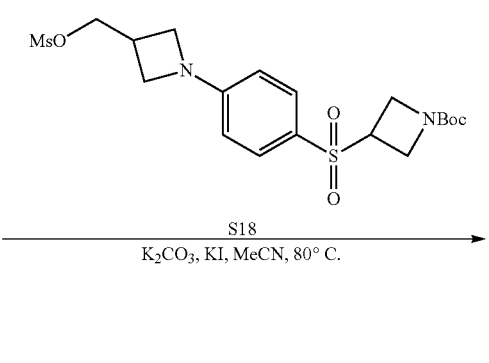
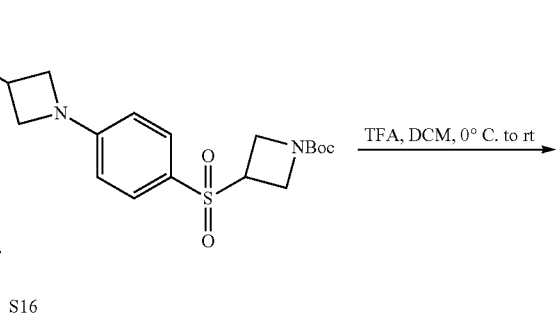
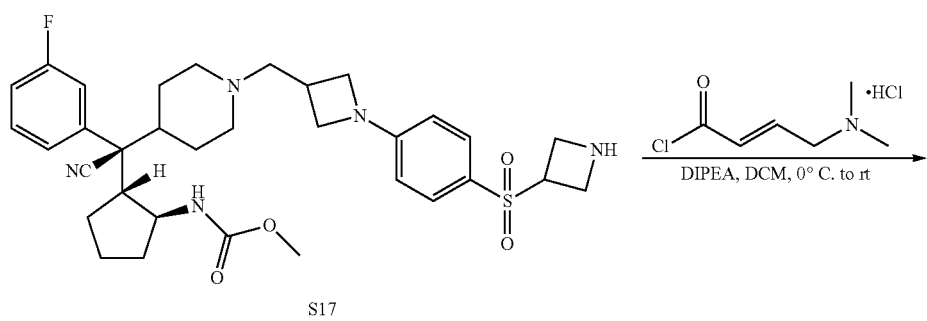

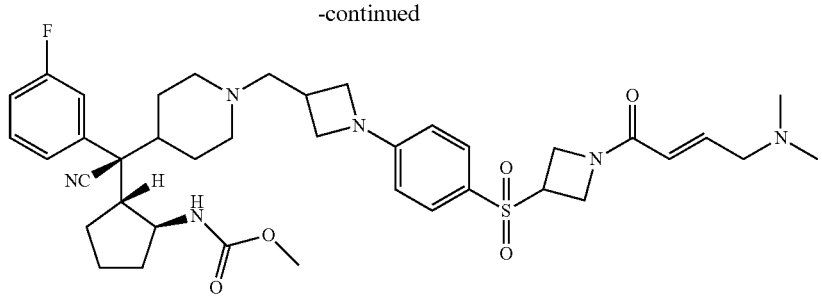

Cpd. No. 57

Synthesis of methyl ((1S,2R)-2-((S)-cyano(3-fluorophenyl)(piperidin-4-yl)methyl)cyclopentyl)carbamate (S15)

To a solution of the intermediate S6 (650 mg, 1.42 mmol) in methanol (20 mL) was added 10% Pd/C (303 mg). The mixture was stirred for 3 h at room temperature under hydrogen atmosphere (normal pressure). After the Pd/C catalyst was filtered off, the solvent was removed by rotary evaporation to give the title compound (500 mg, 98%). $^1$H NMR (400 MHz, MeOD) δ 7.48-7.42 (m, 1H), 7.36 (d, J=7.8 Hz, 1H), 7.27 (d, J=10.5 Hz, 1H), 7.16-7.11 (m, 1H), 3.91-3.85 (m, 1H), 3.44 (s, 3H), 3.41-3.37 (m, 2H), 3.00 (t, J=12.4 Hz, 2H), 2.87-2.81 (m, 1H), 2.46 (t, J=12.1 Hz, 1H), 2.22 (d, J=13.9 Hz, 1H), 2.15-2.12 (m, 1H), 1.90 (d, J=13.8 Hz, 1H), 1.84-1.77 (m, 1H), 1.73-1.44 (m, 5H), 1.39-1.29 (m, 1H); ESI-MS calculated for $C_{20}H_{26}FN_3O_2$ $[M+H]^+$=360.20, found: 360.25.

Synthesis of methyl ((1S,2R)-2-((S)-cyano(1-((1-(4-((1-((E)-4-(dimethylamino)but-2-enoyl)azetidin-3-yl)sulfonyl)phenyl)azetidin-3-yl)methyl)piperidin-4-yl)(3-fluorophenyl)methyl)cyclopentyl)carbamate (Cpd. No. 57)

To a solution of the intermediate S15 (100 mg, 0.278 mmol) in acetonitrile (5 mL) was added compound S18 (154 mg, 0.334 mmol), $K_2CO_3$ (77 mg, 0.556 mmol) and KI (4.6 mg, 0.028 mmol). The mixture was stirred at 80° C. overnight. Then, the mixture was extracted with ethyl acetate, washed with brine, dried over $Na_2SO_4$, and the solvent was evaporated under vacuum. The residue was purified by reverse phase preparative HPLC to give the salt of S17. Compound S17 was dissolved in dichloromethane (5 mL) and trifluoroacetic acid (5 mL) was added at 0° C. After stirring for 15 min at room temperature, the reaction mixture was concentrated under vacuum, basified with saturated $NaHCO_3$, extracted with dichloromethane three times. The combined organic layers were dried over $Na_2SO_4$, filtered and concentrated under vacuum. The resulting residue was redissolved in dry dichloromethane (2 mL). Then, DIPEA (0.145 mL, 0.834 mmol) and (2E)-4-(dimethylamino)but-2-enoyl chloride hydrochloride (62 mg, 0.334 mmol) were added at 0° C. After stirring for 2 h at room temperature, the reaction mixture was concentrated under vacuum. The residue was purified by reverse phase preparative HPLC to give Cpd. No. 57 as a salt of trifluoroacetic acid (95 mg, 46%). ESI-MS m/z 735.40 (M+H)+; 1H NMR (400 MHz, MeOD) δ 7.70 (d, J=8.9 Hz, 2H), 7.48-7.42 (m, 1H), 7.34 (d, J=7.8 Hz, 1H), 7.26 (d, J=10.5 Hz, 1H), 7.16-7.12 (m, 1H), 6.77-6.70 (m, 1H), 6.54 (d, J=8.9 Hz, 2H), 6.47 (d, J=15.3 Hz, 1H), 4.52 (d, J=6.3 Hz, 2H), 4.29-4.16 (m, 5H), 3.95-3.93 (m, 2H), 3.90-3.85 (m, 1H), 3.78-3.74 (m, 2H), 3.57 (t, J=13.0 Hz, 2H), 3.45-3.35 (m, 2H), 3.43 (s, 3H), 3.27-3.22 (m, 1H), 3.07-3.01 (m, 2H), 2.90 (s, 6H), 2.87-2.82 (m, 1H), 2.46 (t, J=11.7 Hz, 1H), 2.30 (d, J=14.5 Hz, 1H), 2.16-2.13 (m, 1H), 1.97 (d, J=15.2 Hz, 1H), 1.85-1.78 (m, 1H), 1.74-1.53 (m, 5H), 1.48-1.38 (m, 1H); $^{13}$C NMR (100 MHz, MeOD) δ 165.8, 165.2, 162.7, 158.0, 137.1, 133.0, 131.6, 131.5, 131.4, 131.3, 128.4, 125.6, 124.1, 121.6, 116.5, 116.2, 111.6, 60.9, 58.7, 56.8, 56.1, 55.8, 53.6, 52.3, 52.2, 51.8, 50.2, 43.3, 41.0, 35.0, 30.0, 27.6, 26.7, 25.8, 23.8.

Example 3

Synthesis of Methyl ((1S,2R)-2-((S)-1-(1-((1-(4-((1-((E)-4-(dimethylamino)but-2-enoyl)azetidin-3-yl)sulfonyl)phenyl)azetidin-3-yl)methyl)piperidin-4-yl)-1-(3-fluorophenyl)-2-(1H-1,2,3-triazol-1-yl)ethyl)cyclopentyl)carbamate (Cpd. No. 72)

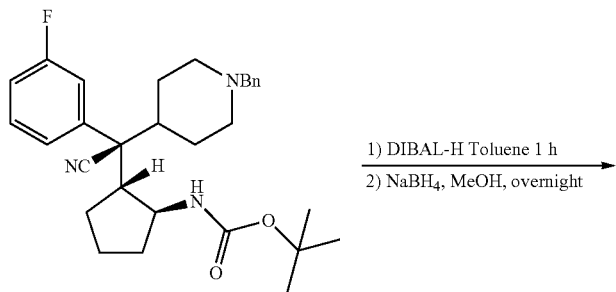

S4

1) DIBAL-H Toluene 1 h
2) NaBH$_4$, MeOH, overnight

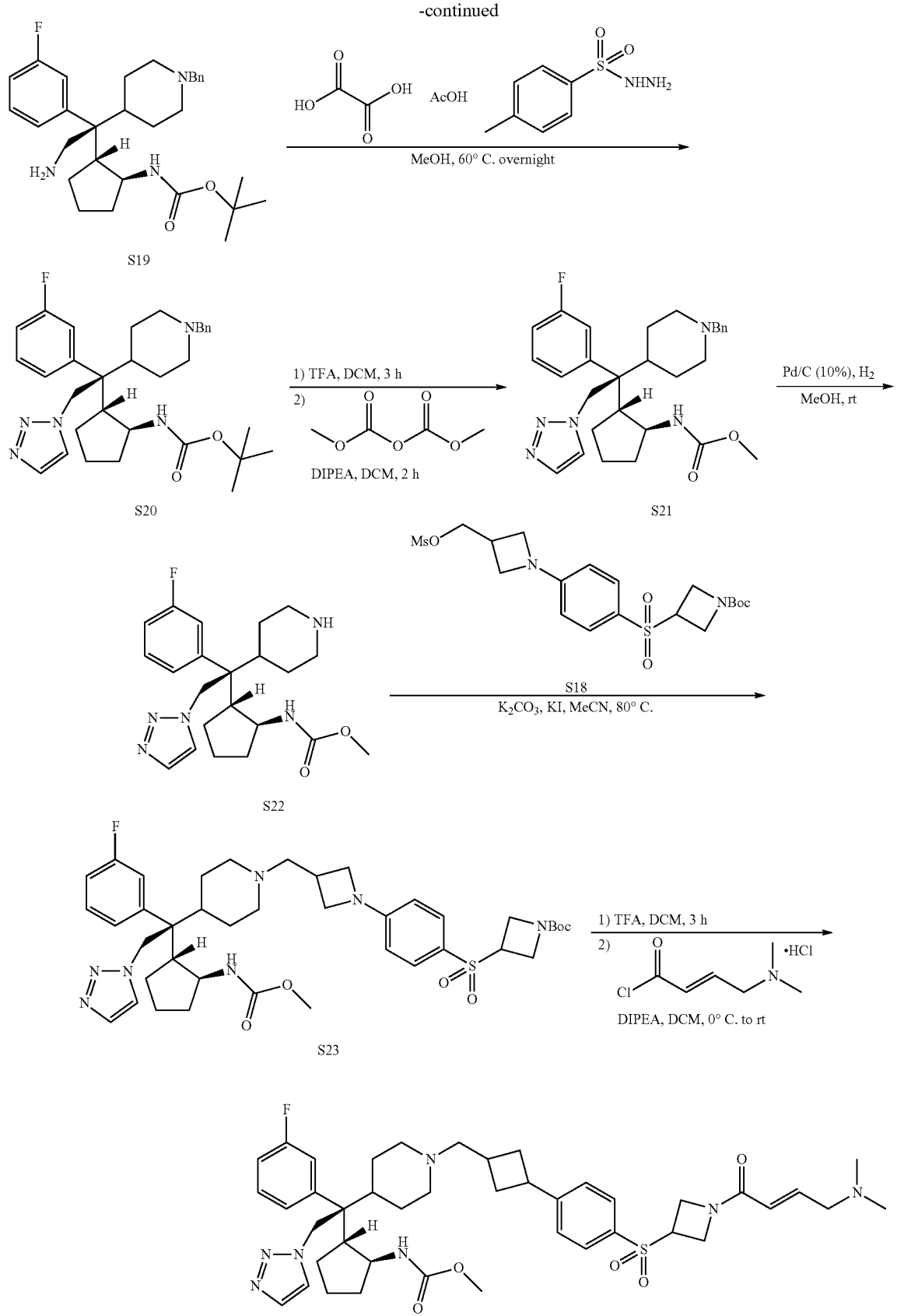

Synthesis of Tert-butyl ((1S,2R)-2-((S)-2-amino-1-(1-benzylpiperidin-4-yl)-1-(3-fluorophenyl)ethyl)cyclopentyl)carbamate (S19)

To an ice cold solution of the intermediate S4 (4 g, 8.14 mmol) in toluene (40 mL) was added diisobutylaluminiumhydride (25% in toluene, 21.9 mL) under argon. The mixture was then allowed to warm to room temperature and stirred for 2 h. The mixture was cooled to 0° C. and quenched by careful addition of IM aqueous NaOH (25 mL). The suspension was stirred for another 10 minutes, and filtered. The filtrate was extracted with ethyl acetate, dried over $Na_2SO_4$ and evaporated. The residue was dried in vacuum and then dissolved in methanol (40 mL). $NaBH_4$ (616 mg, 16.3 mmol) was added into the mixture, and the reaction mixture was stirred at room temperature overnight. The mixture was concentrated in vacuum and diluted with ethyl acetate and water. The mixture was extracted with ethyl acetate, dried ($Na_2SO_4$), and the solvent was evaporated to give the title compound (3.5 g, 87%) without further purification.

Synthesis of Tert-butyl ((1S,2R)-2-((S)-1-(1-benzylpiperidin-4-yl)-1-(3-fluorophenyl)-2-(1H-1,2,3-triazol-1-yl)ethyl)cyclopentyl)carbamate (S20)

To a solution of crude S19 (500 mg, 1.01 mmol), oxalaldehyde (0.29 mL, 2.52 mmol), AcOH (12 mg, 0.2 mmol) and 4-methylbenzenesulfonohydrazide (206 mg, 1.11 mmol) in MeOH (5 mL) and stirred at 60° C. overnight. The crude product was purified by reverse phase prep-HPLC, and the pure product was lyophilized to give S20-TFA (260 mg, 47%) salt as white solid.

Synthesis of Methyl ((1S,2R)-2-((S)-1-(1-((1-(4-((1-((E)-4-(dimethylamino)but-2-enoyl)azetidin-3-yl)sulfonyl)phenyl)azetidin-3-yl)methyl)piperidin-4-yl)-1-(3-fluorophenyl)-2-(1H-1,2,3-triazol-1-yl)ethyl)cyclopentyl)carbamate (Cpd. No. 72)

Cpd. No. 72 was synthesized using the method described for compound Cpd. No. 7 from the intermediate S20. ESI-MS m/z 791.51 (M+H)$^+$.

Example 4

Synthesis of N-((1S,2R)-2-((S)-cyano(1-((1-(4-cyanophenyl)azetidin-3-yl)methyl)piperidin-4-yl)(3-fluorophenyl)methyl)cyclopentyl)acrylamide (Cpd. No. 80)

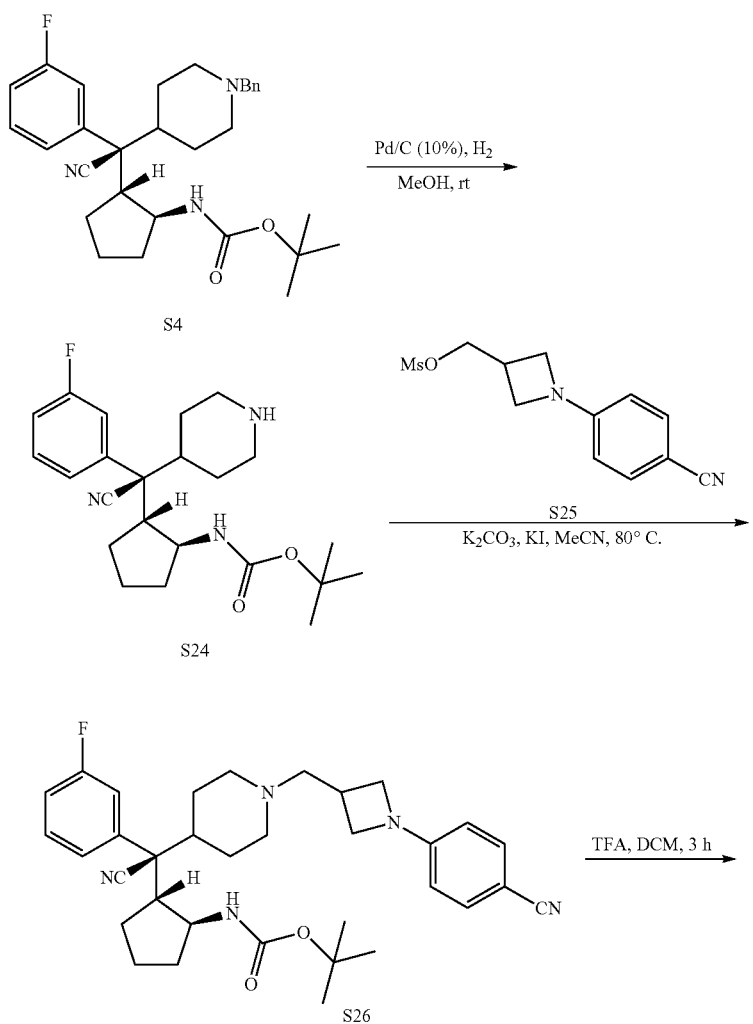

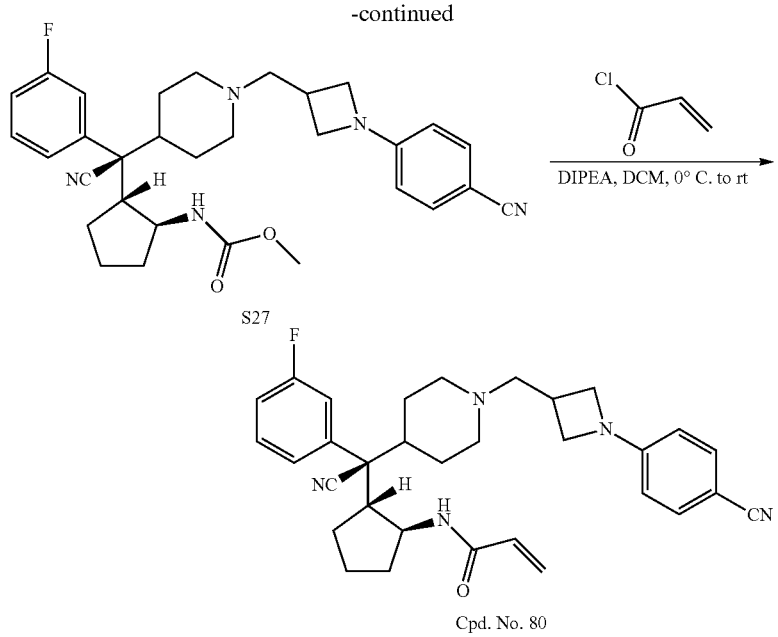

Cpd. No. 80

Synthesis of tert-butyl ((1S,2R)-2-((S)-cyano(3-fluorophenyl)(piperidin-4-yl)methyl)cyclopentyl) carbamate (S24)

To a solution of the intermediate S4 (300 mg, 0.61 mmol) in methanol (10 mL) was added 10% Pd/C (65 mg). The mixture was stirred for 3 h at room temperature under hydrogen atmosphere (normal pressure). After the Pd/C catalyst was filtered off, the solvent was removed by rotary evaporation to give the title compound (230 mg, 94%).

Synthesis of tert-butyl ((1S,2R)-2-((S)-cyano(1-((1-(4-cyanophenyl)azetidin-3-yl)methyl)piperidin-4-yl)(3-fluorophenyl)methyl)cyclopentyl)carbamate (S26)

To a solution of the intermediate S24 (245 mg, 0.61 mmol) in acetonitrile (5 mL) was added (1-(4-cyanophenyl)azetidin-3-yl)methyl methanesulfonate (S25) (195 mg, 0.732 mmol), K$_2$CO$_3$ (168 mg, 1.22 mmol) and KI (10 mg, 1.22 mmol). The mixture was stirred at 80° C. overnight. Then, the mixture was extracted with ethyl acetate, washed with brine, dried over Na$_2$SO$_4$, and the solvent was evaporated under vacuum. The residue was purified by flash column to give the title compound (250 mg, 72%).

Synthesis of 4-(3-((4-((S)-((1R,2S)-2-aminocyclopentyl)(cyano)(3-fluorophenyl)methyl)piperidin-1-yl)methyl)azetidin-1-yl)benzonitrile (S27)

Compound S26 (250 mg, 0.437 mmol) was dissolved in dichloromethane (5 mL) and trifluoroacetic acid (5 mL) was added at 0° C. After stirring for 15 min at room temperature, the reaction mixture was concentrated under vacuum, basified with saturated NaHCO$_3$, extracted with dichloromethane three times. The combined organic layers were dried over Na$_2$SO$_4$, filtered and concentrated under vacuum for next step without further purification.

Synthesis of N-((1S,2R)-2-((S)-cyano(1-((1-(4-cyanophenyl)azetidin-3-yl)methyl)piperidin-4-yl)(3-fluorophenyl)methyl)cyclopentyl)acrylamide (Cpd. No. 80)

The intermediate S27 (29 mg, 0.062 mmoL) was redissolved in dry dichloromethane (2 mL). Then, DIPEA (16 mg, 0.123 mmol) and acryloyl chloride (6.7 mg, 0.074 mmol) were added at 0° C. After stirring for 0.5 h at room temperature, the reaction mixture was concentrated under vacuum. The residue was purified by reverse phase preparative HPLC to give Cpd. No. 80 as a salt of trifluoroacetic acid (20 mg, 62%). ESI-MS m/z 526.47 (M+H)$^+$.

Example 5

The following compounds were prepared using methods described in Examples 1-4 and known in the art:

Cpd. No. 1: (1S,2R)-2-((S)-(1-((1-(4-((1-acryloylazetidin-3-yl)sulfonyl)phenyl) azetidin-3-yl)methyl)piperidin-4-yl)(cyano)(3-fluorophenyl)methyl)cyclopentyl methylcarbamate; MS (ESI) m/z 678.39 [M+H]$^+$.

Cpd. No. 2: (1S,2R)-2-((R)-(1-((1-(4-((1-acryloylazetidin-3-yl)sulfonyl)phenyl) azetidin-3-yl)methyl)piperidin-4-yl)(cyano)(3-fluorophenyl)methyl)cyclopentyl methylcarbamate; MS (ESI) m/z 678.39 [M+H]$^+$.

Cpd. No. 3: (1S,2R)-2-((S)-(1-((1-(4-((3-acrylamidophenyl)sulfonyl)phenyl) azetidin-3-yl)methyl)piperidin-4-yl)(cyano)(3-fluorophenyl)methyl)cyclopentyl methylcarbamate; MS (ESI) m/z 714.54 [M+H]$^+$.

Cpd. No. 4: (1S,2R)-2-((R)-(1-((1-(4-((3-acrylamidophenyl)sulfonyl) phenyl)azetidin-3-yl)methyl)piperidin-4-yl)(cyano)(3-fluorophenyl)methyl)cyclopentyl methylcarbamate; MS (ESI) m/z 714.49 [M+H]$^+$.

Cpd. No. 5: methyl ((1S,2R)-2-((S)-(1-((1-(4-((3-acrylamidophenyl)sulfonyl) phenyl)azetidin-3-yl)methyl)piperidin-4-yl)(cyano)(3-fluorophenyl)methyl)cyclopentyl)carbamate MS (ESI) m/z 714.44 [M+H]$^+$.

Cpd. No. 6: methyl ((1S,2R)-2-((S)-(1-((1-(4-((1-acryloylazetidin-3-yl) sulfonyl)phenyl)azetidin-3-yl)methyl)piperidin-4-yl)(cyano)(3-fluorophenyl)methyl) cyclopentyl) carbamate; MS (ESI) m/z 678.40 [M+H]⁺.

Cpd. No. 8: methyl ((1S,2R)-2-((S)-1-(1-((1-(4-((1-acryloylazetidin-3-yl)sulfonyl)phenyl)azetidin-3-yl)methyl)piperidin-4-yl)-2-(2-ethyl-1H-imidazol-1-yl)-1-(3-fluorophenyl)ethyl)cyclopentyl)carbamate; MS (ESI) m/z 761.46 [M+H]⁺

Cpd. No. 9: methyl ((1S,2R)-2-((S)-1-(1-((1-(4-((3-acrylamidophenyl)sulfonyl) phenyl)-3-fluoroazetidin-3-yl)methyl)piperidin-4-yl)-2-(2-ethyl-1H-imidazol-1-yl)-1-(3-fluorophenyl)ethyl)cyclopentyl)carbamate; MS (ESI) m/z 815.44 [M+H]⁺.

Cpd. No. 10: (1S,2R)-2-((S)-(1-((1-(4-((4-acrylamidophenyl)sulfonyl) phenyl)azetidin-3-yl)methyl)piperidin-4-yl)(cyano)(3-fluorophenyl)methyl)cyclopentyl methylcarbamate; MS (ESI) m/z 714.42 [M+H]⁺.

Cpd. No. 11: (1S,2R)-2-((R)-(1-((1-(4-((4-acrylamidophenyl)sulfonyl)phenyl) azetidin-3-yl)methyl)piperidin-4-yl)(cyano)(3-fluorophenyl)methyl)cyclopentyl methylcarbamate; MS (ESI) m/z 714.40 [M+H]⁺.

Cpd. No. 12: methyl ((1S,2R)-2-((S)-1-(1-(4-((3-acrylamidophenyl) sulfonyl)phenyl)-3-fluoroazetidin-3-yl)methyl)piperidin-4-yl)(cyano)(3-fluorophenyl)methyl)cyclopentyl)carbamate; MS (ESI) m/z 732.37 [M+H]⁺.

Cpd. No. 13: ethyl ((1S,2R)-2-((S)-(1-((1-(4-((1-acryloylazetidin-3-yl)sulfonyl)phenyl)-3-fluoroazetidin-3-yl)methyl)piperidin-4-yl)(cyano)(3-fluorophenyl)methyl)cyclopentyl)carbamate; MS (ESI) m/z 696.34 [M+H]⁺.

Cpd. No. 14: N-((1S,2R)-2-((S)-cyano(1-((1-(4-((1-methyl-1H-pyrazol-4-yl) sulfonyl)phenyl)azetidin-3-yl)methyl)piperidin-4-yl)(phenyl)methyl)cyclopentyl) acrylamide (racemic); ESI-MS m/z 627.39 (M+H)⁺.

Cpd. No. 15: N-((1R,2S)-2-((S)-cyano(1-((1-(4-((1-methyl-1H-pyrazol-4-yl) sulfonyl)phenyl)azetidin-3-yl)methyl)piperidin-4-yl)(phenyl)methyl)cyclopentyl) acrylamide (racemic); ESI-MS m/z 627.41 (M+H)⁺.

Cpd. No. 16: methyl ((1S,2R)-2-((S)-1-(1-((1-(4-((1-acryloylazetidin-3-yl)sulfonyl)phenyl)-3-fluoroazetidin-3-yl)methyl)piperidin-4-yl)-2-(2-ethyl-1H-imidazol-1-yl)-1-(3-fluorophenyl)ethyl)cyclopentyl)carbamate (enantiomer); ESI-MS m/z 779.36 (M+H)⁺.

Cpd. No. 17: methyl ((1S,2R)-2-((S)-(1-((1-(4-((1-acryloylpiperidin-4-yl) sulfonyl)phenyl)azetidin-3-yl)methyl)piperidin-4-yl)(cyano)(3-fluorophenyl)methyl) cyclopentyl) carbamate (enantiomer); ESI-MS m/z 706.38 (M+H)⁺.

Cpd. No. 20: ESI-MS m/z 698.42 (M+H)⁺.

Cpd. No. 21: ESI-MS m/z 712.49 (M+H)⁺.

Cpd. No. 53: (1S,2R)-2-((S)-cyano(3-fluorophenyl)(1-((1-(4-(vinylsulfonyl)phenyl)azetidin-3-yl)methyl)piperidin-4-yl)methyl)cyclopentyl methylcarbamate (racemic); ESI-MS m/z 595.28 (M+H)⁺.

Cpd. No. 54: ESI-MS m/z 662.42 (M+H)⁺.

Cpd. No 0.55: ESI-MS m/z 676.45 (M+H)⁺.

Cpd. No. 56: ESI-MS m/z 692.48 (M+H)⁺.

Cpd. No. 58: ESI-MS m/z 813.42 (M+H)⁺.

Cpd. No. 59: ESI-MS m/z 777.58 (M+H)⁺.

Cpd. No. 60: ESI-MS m/z 735.45 (M+H)+; ¹H NMR (400 MHz, MeOD) δ 7.70 (d, J=8.8 Hz, 2H), 7.52-7.47 (m, 1H), 7.31 (d, J=7.8 Hz, 1H), 7.25-7.15 (m, 2H), 6.77-6.70 (m, 1H), 6.64 (d, J=8.9 Hz, 2H), 6.48 (d, J=15.3 Hz, 1H), 4.54-4.52 (m, 2H), 4.29-4.14 (m, 5H), 4.12-4.06 (m, 1H), 3.95-3.93 (m, 2H), 3.79-3.74 (m, 2H), 3.69 (s, 3H), 3.58 (t, J=13.6 Hz, 2H), 3.45 (d, J=7.1 Hz, 2H), 3.26-3.19 (m, 1H), 3.14-3.08 (m, 1H), 2.90 (s, 6H), 2.88-2.84 (m, 2H), 2.63 (t, J=12.0 Hz, 1H), 2.30 (d, J=14.1 Hz, 1H), 2.03-1.96 (m, 2H), 1.87-1.79 (m, 1H), 1.68-1.59 (m, 3H), 1.51-1.42 (m, 2H), 1.32-1.23 (m, 1H); ¹³C NMR (100 MHz, MeOD) δ 165.8, 165.4, 162.9, 158.7, 156.0, 137.9, 137.8, 133.0, 131.7, 131.6, 131.3, 128.4, 125.4, 124.0, 121.9, 116.6, 116.4, 111.6, 61.0, 58.7, 56.7, 56.1, 56.0, 55.8, 53.7, 52.7, 52.2, 51.9, 50.2, 50.0, 43.3, 40.4, 35.6, 30.6, 27.6, 26.7, 26.0, 24.3.

Cpd. No. 61: ESI-MS m/z 714.36 (M+H)+; ¹H NMR (400 MHz, MeOD) δ 7.80 (s, 4H), 7.70 (d, J=8.8 Hz, 2H), 7.47-7.42 (m, 1H), 7.35 (d, J=7.6 Hz, 1H), 7.16-7.12 (m, 1H), 6.84 (d, J=8.8 Hz, 1H), 6.47 (m, J=8.9 Hz, 2H), 6.41-6.36 (m, 2H), 5.82-5.79 (m, 1H), 4.13 (t, =7.9 Hz, 3.90-3.87 (m, 1H), 3.71-3.68 (m, 2H), 3.58-3.51 (m, 2H), 3.43 (s, 3H), 3.42-3.36 (m, 2H), 3.21-3.16 (m, 1H), 3.06-2.98 (m, 2H), 2.86-2.80 (m, 1H), 2.49-2.43 (m, 1H), 2.26 (d, J=12.4 Hz, 1H), 2.15-2.13 (m, 1H), 1.97-1.94 (m, 1H), 1.84-1.77 (m, 1H), 1.73-1.68 (m, 2H), 1.62-1.52 (m, 3H), 1.47-1.37 (m, 1H); ¹³C NMR (100 MHz, MeOD) δ 166.3, 165.2, 163.1, 162.8, 158.1, 155.4, 144.1, 139.0, 137.1, 132.1, 131.5, 131.4, 130.2, 129.8, 129.1, 128.9, 125.6, 121.6, 121.0, 116.5, 116.3, 111.7, 61.0, 56.8, 56.2, 55.7, 53.6, 52.3, 49.9, 49.7, 40.9, 35.0, 30.0, 27.6, 26.7, 25.8, 23.8

Cpd. No. 62: ESI-MS m/z 724.47 (M+H)⁺.

Cpd. No. 63: ESI-MS m/z 771.37 (M+H)+; ¹H NMR (400 MHz, MeOD) δ 8.34 (s, 1H), 7.77-7.75 (m, 1H), 7.71 (d, J=8.8 Hz, 2H), 7.61-7.58 (m, 1H), 7.49 (t, J=8.0 Hz, 1H), 7.45-7.41 (m, 1H), 7.34 (d, J=8 Hz, 1H), 7.25 (d, J=10.4 Hz, 1H), 7.16-7.11 (m, 1H), 6.92-6.84 (m, 1H), 6.53 (d, J=15.2 Hz, 1H), 6.47 (d, J=8.8 Hz, 2H), 4.15-4.11 (m, 2H), 4.00-3.98 (m, 2H), 3.89-3.84 (m, 1H), 3.71-3.68 (m, 2H), 3.55 (t, J=12.4 Hz, 2H), 3.42-3.40 (m, 5H), 3.24-3.16 (m, 1H), 3.06-2.98 (m, 2H), 2.93 (s, 6H), 2.86-2.81 (m, 1H), 2.45 (t, J=12.4 Hz, 1H), 2.26-2.22 (m, 1H), 2.15-2.13 (m, 1H), 1.98-1.94 (m, 1H), 1.84-1.77 (m, 1H), 1.73-1.52 (m, 5H), 1.45-1.33 (m, 1H); ¹³C NMR (100 MHz, MeOD) δ 164.38, 162.73, 158.03, 155.50, 145.18, 140.63, 137.13, 133.79, 132.80, 131.47, 131.39, 131.03, 128.93, 125.59, 124.81, 123.62, 121.59, 119.20, 116.45, 116.24, 111.66, 60.92, 58.75, 56.81, 56.18, 55.77, 53.54, 52.29, 49.49, 49.28, 43.26, 40.97, 35.03, 30.01, 27.59, 26.71, 25.76, 23.82.

Cpd. No. 64: ESI-MS m/z 662.36 (M+H)⁺.

Cpd. No. 65: ESI-MS m/z 662.28 (M+H)⁺.

Cpd. No. 66: ESI-MS m/z 836.40 (M+H)⁺.

Cpd. No. 67: ESI-MS m/z 818.61 (M+H)⁺.

Cpd. No. 68: ESI-MS m/z 724.40 (M+H)⁺.

Cpd. No. 69: ESI-MS m/z 753.47 (M+H)⁺.

Cpd. No. 70: ESI-MS m/z 714.36 (M+H)⁺.

Cpd. No. 71: ESI-MS m/z 775.47 (M+H)⁺.

Cpd. No. 73: ESI-MS m/z 858.85 (M+H)⁺.

Cpd. No. 74: ESI-MS m/z 761.31 (M+H)⁺.

Cpd. No. 75: ESI-MS m/z 763.41 (M+H)⁺.

Cpd. No. 76: ESI-MS m/z 627.55 (M+H)⁺.

Cpd. No. 77: ESI-MS m/z 692.54 (M+H)⁺.

Cpd. No. 78: ESI-MS m/z 706.64 (M+H)⁺.

Cpd. No. 79: ESI-MS m/z 562.40 (M+H)⁺.

Example 6

Menin Binding Affinity

A fluorescence polarization (FP) competitive binding assay was used to determine the binding affinities of representative menin inhibitors. A FAM labeled fluorescent probe was designed and synthesized based on a MLL1 peptide (FAM-MM2). Equilibrium dissociation constant ($K_d$) value of FAM-MM2 to menin protein was determined from protein saturation experiments by monitoring the total fluorescence polarization of mixtures composed with the fluorescent probe at a fixed concentration and the protein with increasing concentrations up to full saturation. Serial dilutions of the protein were mixed with FAM-MM2 to a final volume of 200 µl in the assay buffer (PBS with 0.02% Bovine γ-Globulin and 4% DMSO. 0.01% Triton X-100 was added right before assays). Final FAM-MM2 concentration was 2 nM. Plates were incubated at room temperature for 30 minutes with gentle shaking to assure equilibrium. FP values in millipolarization units (mP) were measured using the Infinite M-1000 plate reader (Tecan U.S., Research Triangle Park, N.C.) in Microfluor 1 96-well, black, v-bottom plates (Thermo Scientific, Waltham, Mass.) at an excitation wavelength of 485 nm and an emission wavelength of 530 nm. $K_d$ value of FAM-MM2, which was calculated by fitting the sigmoidal dose-dependent FP increases as a function of protein concentrations using Graphpad Prism 6.0 software (Graphpad Software, San Diego, Calif.), was determined as 1.4 nM.

The $IC_{50}$, see Table 3, of representative Compounds of the Disclosure were determined in a competitive binding experiment. Mixtures of 5 µl of the tested compounds in DMSO and 195 µl of preincubated protein/probe complex solution in the assay buffer were added into assay plates which were incubated at room temperature for 30 minutes with gentle shaking. Final concentration of the menin protein was 4 nM, and final probe concentration is 2 nM. Negative controls containing protein/probe complex only (equivalent to 0% inhibition), and positive controls containing only free probes (equivalent to 100% inhibition), were included in each assay plate. FP values were measured as described above. $IC_{50}$ values were determined by nonlinear regression fitting of the competition curves.

TABLE 3

| Cpd. No. | Menin Binding Affinity $IC_{50}$ (µM) |
|---|---|
| 1 | 0.005 |
| 2 | 0.374 |
| 3 | 0.003 |
| 4 | 0.3 |
| 5 | 0.002 |
| 6 | 0.003 |
| 7 | 0.003 |
| 8 | 0.002 |
| 9 | 0.002 |
| 10 | 0.002 |
| 11 | 2.2 |
| 12 | 0.042 |
| 13 | 0.024 |
| 16 | 0.002 |
| 56 | 0.005 |
| 57 | 0.003 |
| 58 | 0.005 |
| 59 | 0.004 |
| 60 | >2 |
| 61 | 0.004 |
| 62 | 0.004 |

TABLE 3-continued

| Cpd. No. | Menin Binding Affinity $IC_{50}$ (µM) |
|---|---|
| 63 | 0.002 |
| 64 | >10 |
| 65 | >10 |
| 66 | 0.001 |
| 67 | 0.002 |
| 68 | 0.007 |
| 69 | 0.009 |
| 70 | >10 |
| 71 | 0.004 |
| 72 | 0.002 |
| 73 | 0.002 |
| 74 | 0.003 |
| 75 | 0.006 |
| 76 | 0.005 |
| 77 | 0.011 |
| 78 | 0.010 |
| 79 | 1.07 |
| 80 | 0.007 |
| 81 | 0.009 |
| 82 | 0.004 |

Example 6

Cell Growth Inhibition

The effect of representative Compounds of the Disclosure on cell viability was determined in a 7-day proliferation assay. See Tables 4, 5, and 6. Cells were maintained in the appropriate culture medium with 10% FBS at 37° C. and an atmosphere of 5% $CO_2$.

Cells were seeded in 96-well flat bottom (Corning COSTAR, Corning, N.Y., cat #3595) at a density of 2,000-3,000 cells/well in 100 µl of culture medium. Compounds were serially diluted in the appropriate medium, and 100 µl of the diluted compounds were added to the appropriate wells of the cell plate. After the addition of compounds, the cells were incubated at 37° C. in an atmosphere of 5% $CO_2$ for 7 days. Cell viability was determined using the WST (2-(2-methoxy-4-nitrophenyl)-3-(4-nitrophenyl)-5-(2,4-disulfophenyl)-2H-tetrazolium, monosodium salt) Cell Counting-8 Kit (Dojindo Molecular Technologies, Inc., Rockville, Md.) according to the manufacturers' instructions.

WST-8 reagent was added to each well at a final concentration of 10% (v/v), and then the plates were incubated at 37° C. for 1-2 hours for color development. The absorbance was measured at 450 nm using a SPECTRAmax PLUS plate reader (Molecular Devices, Sunnyvale, Calif.). The readings were normalized to the DMSO-treated cells and the half maximal inhibitory concentration ($IC_{50}$) was calculated by nonlinear regression (four parameters sigmoid fitted with variable slope, least squares fit, and no constraint) analysis using the GraphPad Prism 5 software (GraphPad Software, La Jolla, Calif.).

TABLE 4

| Cell Line | Tissue Type | Genetic Rearrangement | IC$_{50}$ in cell growth inhibition (nM) | | | |
|---|---|---|---|---|---|---|
| | | | Cpd. No. 1 | Cpd. No. 5 | Cpd. No. 6 | Cpd. No. 7 |
| MV4-11 | AML | MLL/AF4 | 4.3 | 8.3 | 44.8 | 2.2 |
| MOLM13 | AML | MLL/AF9 | 27.2 | 41.4 | 154 | 16.9 |
| MOLM14 | AML | MLL/AF9 | 41 | 78.8 | 180 | 17.6 |
| SEM | ALL | MLL/AF9 | 10.9 | 39.6 | 79 | 4.7 |
| MonoMac6 | AML | MLL/AF9 | 84 | 156 | 764 | 67.7 |
| RS4-11 | B-lineage ALL | MLL/AF4 | 8.8 | 10.7 | 62.1 | 5.9 |

TABLE 5

| | IC$_{50}$ in cell growth inhibition (nM) | |
|---|---|---|
| Cpd No. | MV4-11 | MOLM13 |
| 57 | 2.3 | 15.4 |
| 60 | 525 | 1404 |
| 67 | 6 | 31 |
| 72 | 1 | 22 |
| 73 | 0.1 | 6 |
| 74 | 2 | 14 |
| 76 | 117 | 313 |
| 77 | 91 | 1222 |
| 78 | 65 | 291 |

TABLE 6

| Cell Line | Cpd. No. 57 IC$_{50}$ in cell growth inhibition |
|---|---|
| MV4;11 (MLL-AF4) | 2.3 nM |
| MOLM-13 (MLL-AF9) | 15.4 nM |
| MOLM-4 (MLL-AF9) | 31.3 nM |
| SEM (MLL-AF4) | 18.0 nM |
| RS4;11 (MLL-AF9) | 9.4 nM |
| MonoMac6 (MLL-AF9) | 10.3 nM |
| K562 (no MLL fusion) | 4.5 µM |
| MOLM-16 (no MLL fusion) | 6.5 µM |
| SKM-1 (no MLL fusion) | 0.9 µM |
| HL-60 (no MLL fusion) | 1.6 µM |

Example 7

Covalent Binding to Menin Protein

Figure 1:
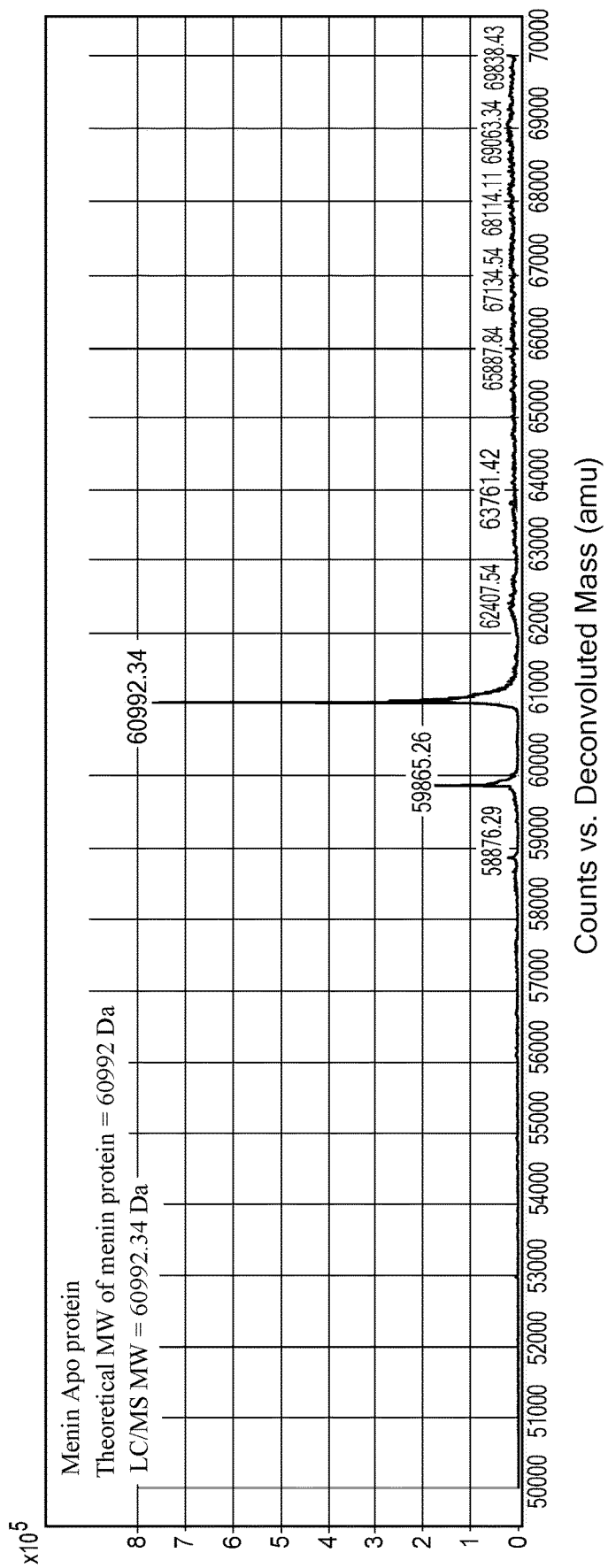
FIG. 1 is a mass spectrograph of menin Apo protein.
Figure 2:
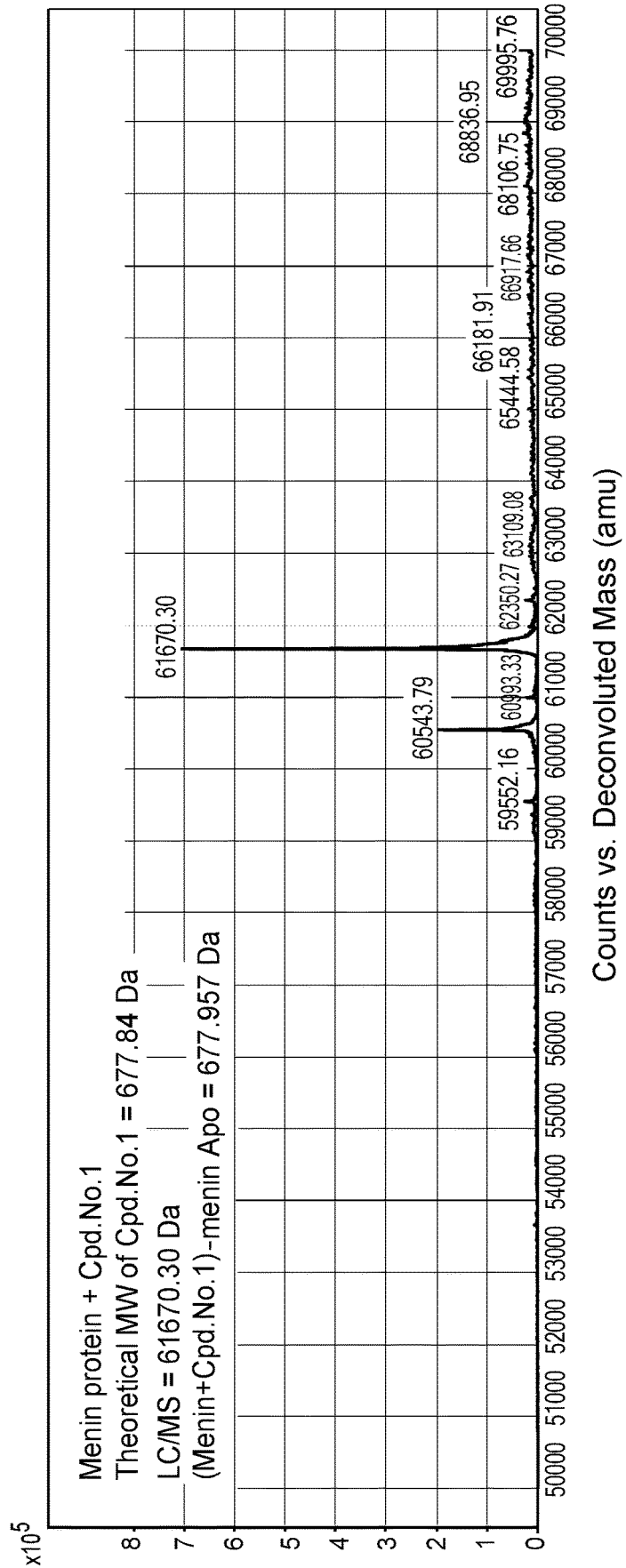
FIG. 2 is a mass spectrograph of menin protein+Cpd. No. 1.
Figure 3:
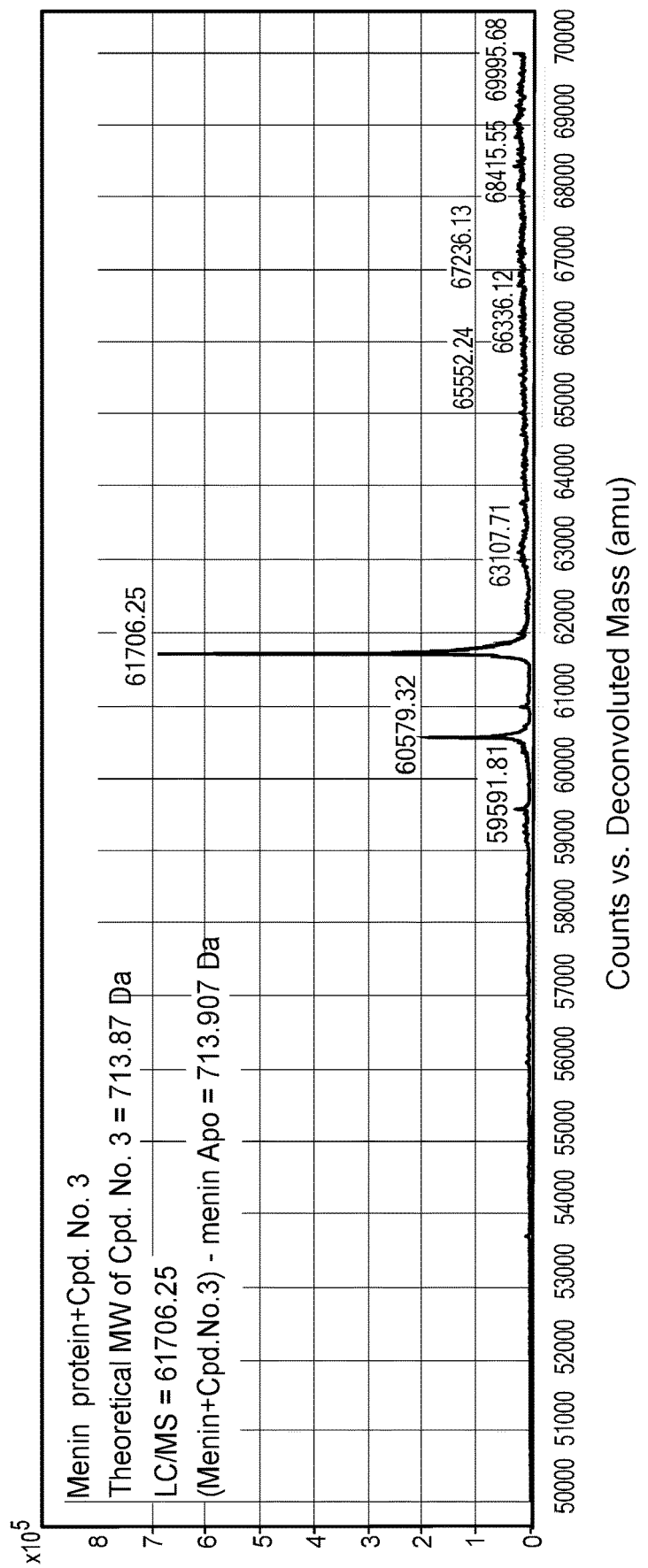
FIG. 3 is a mass spectrograph of menin protein+Cpd. No. 3.

Mass-spectroscopy data indicate that Cpd. No. 1 and Cpd. No. 3 covalently bind with menin protein. Recombinant human menin protein was incubated with Cpd. No. 1 or Cpd. No. 3 and compared to menin protein alone (Menin apo). See FIGS. 1-3.

Example 8

As shown in FIG. 4, FIG. 5, and FIG. 6, Cpd. No. 57 suppresses MEIS1 and HOXA gene expression in MV4;11 and MOLM13 cell lines.

Having now fully described the methods, compounds, and compositions of matter provided herein, it will be understood by those of skill in the art that the same can be performed within a wide and equivalent range of conditions, formulations, and other parameters without affecting the scope of the methods, compounds, and compositions provided herein or any embodiment thereof.

All patents, patent applications and publications cited herein are fully incorporated by reference herein in their entirety.

What is claimed is:

1. A compound having Formula I:

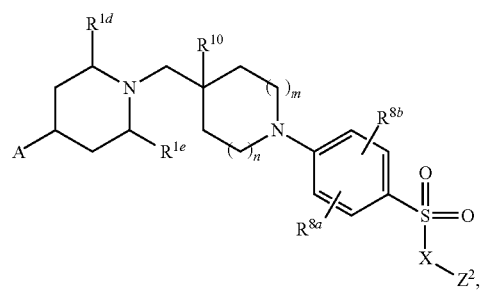

or a pharmaceutically acceptable salt or solvate thereof, wherein:

A is selected from the group consisting of:

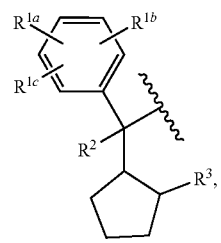

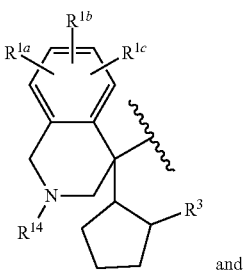

and

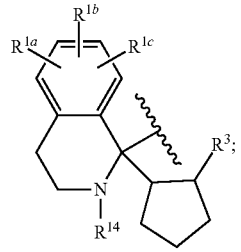

$R^{1a}$, $R^{1b}$, and $R^{1c}$ are each independently selected from the group consisting of hydrogen, halo, cyano, hydroxy, amino, $C_{1-4}$ alkyl, $C_{1-4}$ haloalkyl, and $C_{1-4}$ alkoxy;

$R^{1d}$ and $R^{1e}$ are independently selected from the group consisting of hydrogen and $C_{1-4}$ alkyl;

$R^2$ is selected from the group consisting of hydroxy, amino, cyano, and —$CH_2R^4$;

$R^3$ is selected from the group consisting of hydrogen, —OC(=O)$NR^{11a}R^{11b}$, —NHC(=O)$R^5$, and —$NHZ^1$;

$R^4$ is selected from the group consisting of amino, optionally substituted aryl, and optionally substituted heteroaryl;

$R^5$ is selected from the group consisting of —$NR^{12a}R^{12b}$, $C_{1-4}$ alkoxy, and $C_{1-4}$ alkyl;

X is selected from the group consisting of:

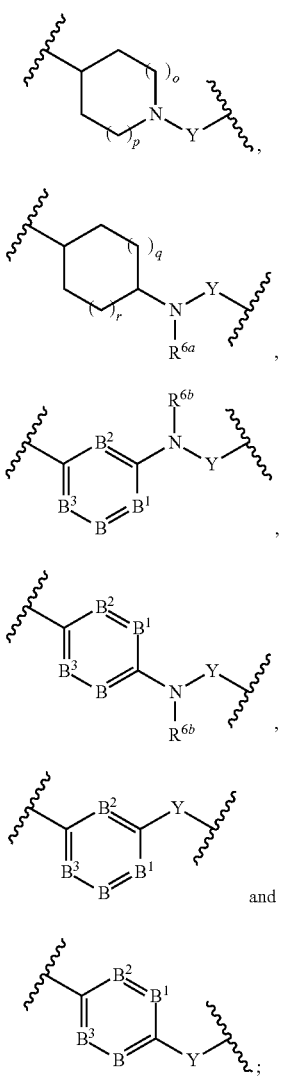

wherein Y is attached to $Z^2$; or
X is absent;
Y is selected from the group consisting of —C(=O)— and —S(=O)$_2$—;
$R^{6a}$ and $R^{6b}$ are independently selected from the group consisting of hydrogen and $C_{1-4}$ alkyl;

m, n, o, p, q, and r are each independently 0, 1, 2, or 3;

$Z^1$ is selected from the group consisting of —C(=O)$R^7$ and —S(=O)$_2R^7$;

$Z^2$ is selected from the group consisting of —CH=$CHR^{13}$, —C≡$CR^{13}$, —$CH_2Cl$, —$CH_2Br$, —$CH_2I$, alkyl, optionally substituted aryl, optionally substituted heteroaryl, and optionally substituted cycloalkyl, with proviso that $Z^2$ is —CH=$CHR^{13}$, —C≡$CR^{13}$, —$CH_2Cl$, —$CH_2Br$, or —$CH_2I$, when $R^3$ is hydrogen, —OC(=O)$NR^{11a}R^{11b}$, or —NHC(=O)$R^5$, $R^7$ is selected from the group consisting of —CH=$CHR^{13}$, —C≡$CR^{13}$, —$CH_2Cl$, —$CH_2Br$, and —$CH_2I$;

$R^{8a}$ and $R^{8b}$ are independently selected from the group consisting of hydrogen, hydrogen, halo, cyano, hydroxy, amino, $C_{1-4}$ alkyl, $C_{1-4}$ haloalkyl, and $C_{1-4}$ alkoxy;

$R^{9a}$ is selected from the group consisting of hydrogen, hydrogen, halo, cyano, hydroxy, amino, $C_{1-4}$ alkyl, $C_{1-4}$ haloalkyl, and $C_{1-4}$ alkoxy;

$R^{10}$ is selected from the group consisting of hydrogen, halo, $C_{1-4}$ alkyl, and hydroxy;

$R^{11a}$ and $R^{11b}$ are independently selected from the group consisting of hydrogen and $C_{1-4}$ alkyl; or $R^{11a}$ and $R^{11b}$ taken together with the nitrogen atom to which they are attached form a 4- to 7-membered heterocyclo; and $R^{12a}$ and $R^{12b}$ are independently selected from the group consisting of hydrogen and $C_{1-4}$ alkyl; or $R^{12a}$ and $R^{12b}$ taken together with the nitrogen atom to which they are attached form a 4- to 7-membered heterocyclo;

$R^{13}$ is selected from the group consisting of hydrogen, $C_{1-4}$ alkyl, and (amino)alkyl;

$R^{14}$ is selected from the group consisting of hydrogen and $C_{1-4}$ alkyl; and B, $B^1$, $B^2$, and $B^3$ are each independently selected from the group consisting of =$CR^{9a}$— and =N—, with proviso that at least one of B, $B^1$, $B^2$, and $B^3$ is =$CR^{9a}$—.

2. The compound of claim 1, or a pharmaceutically acceptable salt or solvate thereof, having Formula I-A-I:

I-A-I

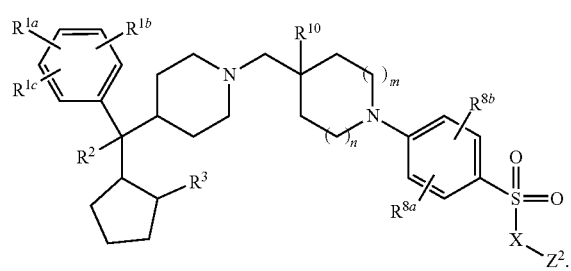

3. The compound of claim 1, or a pharmaceutically acceptable salt or solvate thereof, having Formula X:

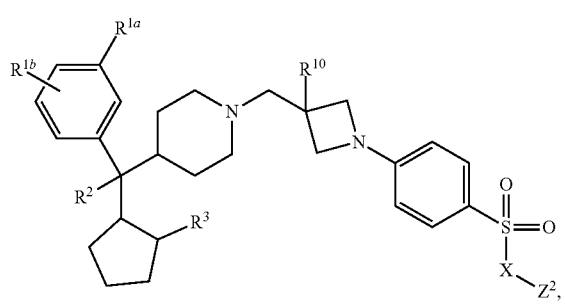

wherein:

X is selected from the group consisting of X-1, X-2, X-3, X-4, X-5, and X-6; or

X is absent;

$Z^2$ is selected from the group consisting of —CH=CHR$^{13}$ and —C≡CR$^{13}$; and $R^3$ is selected from the group consisting of —OC(=O)NR$^{11a}$R$^{11b}$, and —NHC(=O)R$^5$.

4. The compound of claim 3, or a pharmaceutically acceptable salt or solvate thereof, having Formula XI:

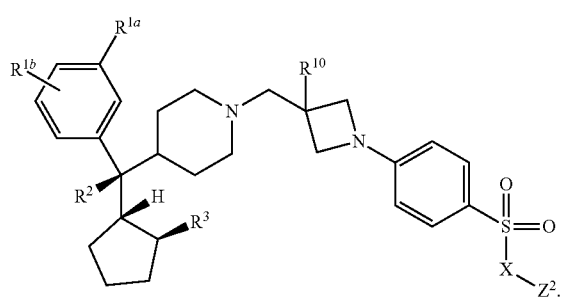

5. The compound of claim 1, or a pharmaceutically acceptable salt or solvate thereof, wherein X is X-1.

6. The compound of claim 1, or a pharmaceutically acceptable salt or solvate thereof, wherein X is X-2.

7. The compound of claim 1, or a pharmaceutically acceptable salt or solvate thereof, wherein X is X-3 and B, B$^1$, B$^2$, and B$^3$ are =CR$^{9a}$—.

8. The compound of claim 1, or a pharmaceutically acceptable salt or solvate thereof, wherein X is X-4 and B, B$^1$, B$^2$, and B$^3$ are =CR$^{9a}$—.

9. The compound of claim 2, or a pharmaceutically acceptable salt or solvate thereof, having Formula XII:

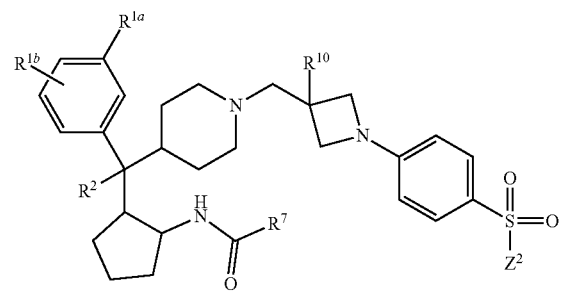

wherein $Z^2$ is selected from the group consisting of alkyl, optionally substituted aryl, optionally substituted heteroaryl, and optionally substituted cycloalkyl.

10. The compound of claim 2, or a pharmaceutically acceptable salt or solvate thereof, having Formula XIV:

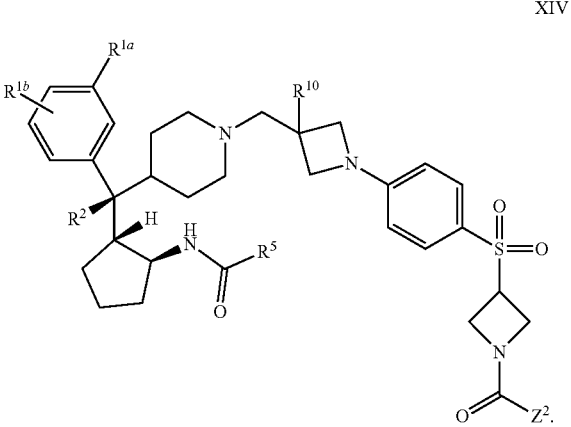

11. A compound having Formula XV or Formula XVII:

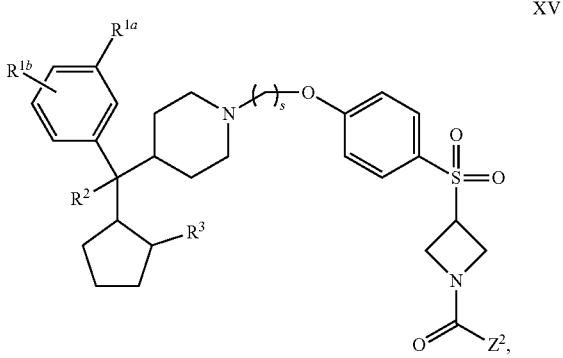

-continued

XVII or a pharmaceutically acceptable salt or solvate thereof, wherein:
$R^{1a}$ and $R^{1b}$ are each independently selected from the group consisting of hydrogen, halo, cyano, hydroxy, amino, $C_{1-4}$ alkyl, $C_{1-4}$ haloalkyl, and $C_{1-4}$ alkoxy;
$R^2$ is selected from the group consisting of hydroxy, amino, cyano, and —$CH_2R^4$;
$R^3$ is selected from the group consisting of hydrogen, —OC(=O)$NR^{11a}R^{11b}$, —NHC(=O)$R^5$, and —$NHZ^1$;
$R^4$ is selected from the group consisting of amino, optionally substituted aryl, and optionally substituted heteroaryl;
$R^5$ is selected from the group consisting of —$NR^{12a}R^{12b}$, $C_{1-4}$ alkoxy, and $C_{1-4}$ alkyl;
$Z^1$ is selected from the group consisting of —C(=O)$R^7$ and —S(=O)$_2R^7$;
$Z^2$ is selected from the group consisting of —CH=$CHR^{13}$, —C≡$CR^{13}$, —$CH_2Cl$, —$CH_2Br$, —$CH_2I$, alkyl, optionally substituted aryl, optionally substituted heteroaryl, and optionally substituted cycloalkyl,
with proviso that $Z^2$ is —CH=$CHR^{13}$, —C≡$CR^{13}$, —$CH_2Cl$, —$CH_2Br$, or —$CH_2I$, when $R^3$ is hydrogen, —OC(=O)$NR^{11a}R^{11b}$, or —NHC(=O)$R^5$,
$R^7$ is selected from the group consisting of —CH=$CHR^{13}$, —C≡$CR^{13}$, —$CH_2Cl$, —$CH_2Br$, and —$CH_2I$;
$R^{11a}$ and $R^{11b}$ are independently selected from the group consisting of hydrogen and $C_{1-4}$ alkyl; or
$R^{11a}$ and $R^{11b}$ taken together with the nitrogen atom to which they are attached form a 4- to 7-membered heterocyclo; and
$R^{12a}$ and $R^{12b}$ are independently selected from the group consisting of hydrogen and $C_{1-4}$ alkyl; or
$R^{12a}$ and $R^{12b}$ taken together with the nitrogen atom to which they are attached form a 4- to 7-membered heterocyclo;
$R^{13}$ is selected from the group consisting of hydrogen, $C_{1-4}$ alkyl, and (amino)alkyl; and
s or t is 2, 3, 4, or 5.

12. A compound having Formula XX:

XX or a pharmaceutically acceptable salt or solvate thereof, wherein:
$R^{1a}$ and $R^{1b}$ are each independently selected from the group consisting of hydrogen, halo, cyano, hydroxy, amino, $C_{1-4}$ alkyl, $C_{1-4}$ haloalkyl, and $C_{1-4}$ alkoxy;
$R^2$ is selected from the group consisting of hydroxy, amino, cyano, and —$CH_2R^4$;
$R^4$ is selected from the group consisting of amino, optionally substituted aryl, and optionally substituted heteroaryl;
$Z^1$ is selected from the group consisting of —C(=O)$R^7$ and —S(=O)$_2R^7$;
$R^7$ is selected from the group consisting of —CH=$CHR^{13}$, —C≡$CR^{13}$, —$CH_2Cl$, —$CH_2Br$, and —$CH_2I$;
$R^{10}$ is selected from the group consisting of hydrogen, halo, $C_{1-4}$ alkyl, and hydroxy; and
$R^{8c}$ is selected from the group consisting of hydrogen, halo, cyano, hydroxy, amino, $C_{1-4}$ alkyl, $C_{1-4}$ haloalkyl, and $C_{1-4}$ alkoxy.

13. The compound of claim 2, or a pharmaceutically acceptable salt or solvate thereof, wherein $R^2$ is cyano.

14. The compound of claim 2, or a pharmaceutically acceptable salt or solvate thereof, wherein $R^2$ is $CH_2R^4$ and $R^4$ is:

15. The compound of claim 1, or a pharmaceutically acceptable salt or solvate thereof, wherein $R^{10}$ is hydrogen or fluoro.

16. The compound of claim 1, or a pharmaceutically acceptable salt or solvate thereof, wherein $R^{1a}$ and $R^{1b}$ are independently selected from the group consisting of hydrogen and halogen.

17. The compound of claim 2, or a pharmaceutically acceptable salt or solvate thereof, wherein:
$Z^2$ is —CH=CHR$^{13}$;
R$^{13}$ is —CH$_2$—NR$^{22c}$R$^{22d}$; and
R$^{22c}$ and R$^{22d}$ are each independently selected from the group consisting of hydrogen and C$_{1-4}$ alkyl, or R$^{22c}$ and R$^{22d}$ are taken together to form a 4- to 8-membered optionally substituted heterocyclo.

18. The compound of claim 1, or a pharmaceutically acceptable salt or solvate thereof, wherein the compound is any one or more of:

1

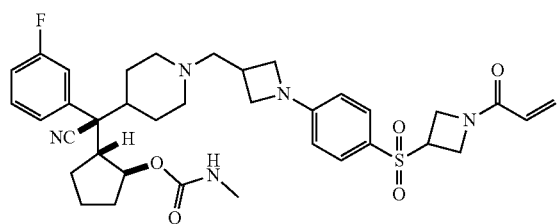

2

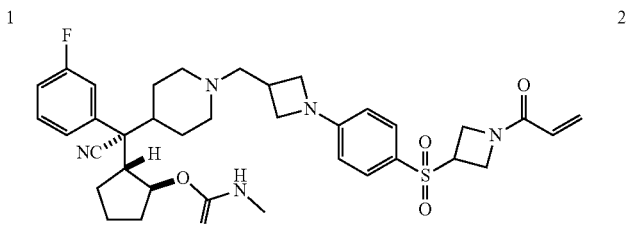

3

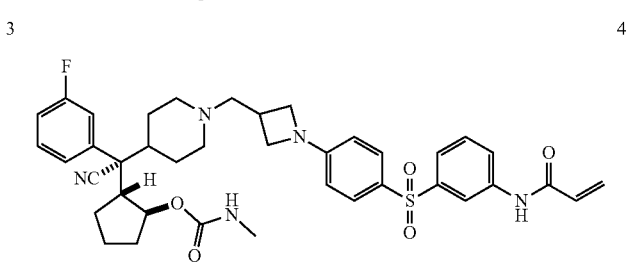

4

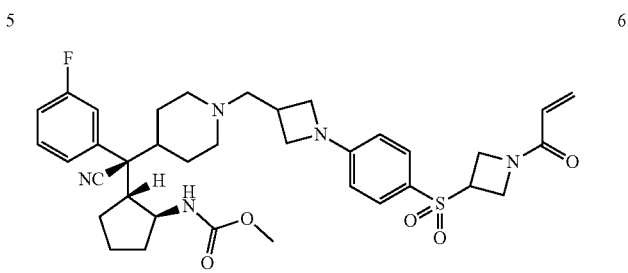

5

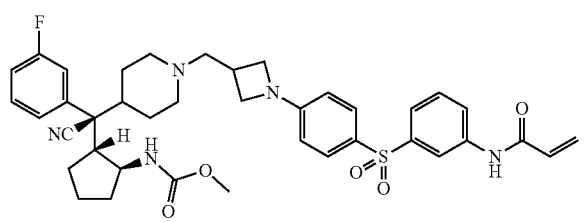

6

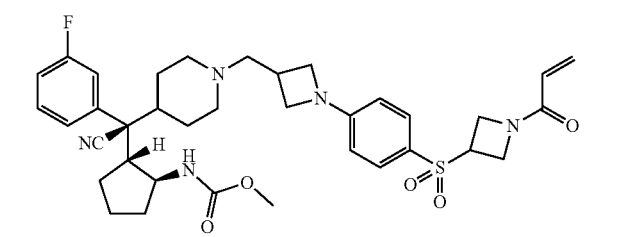

7

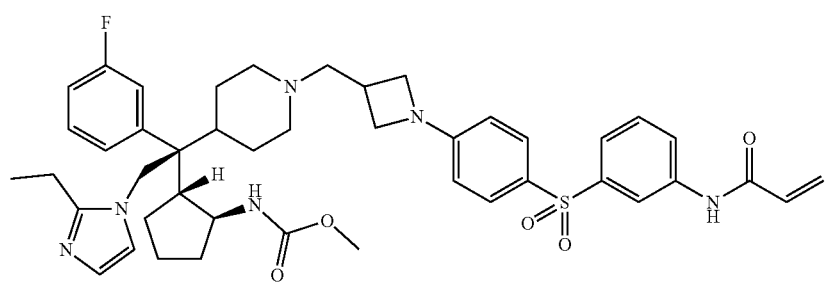

8

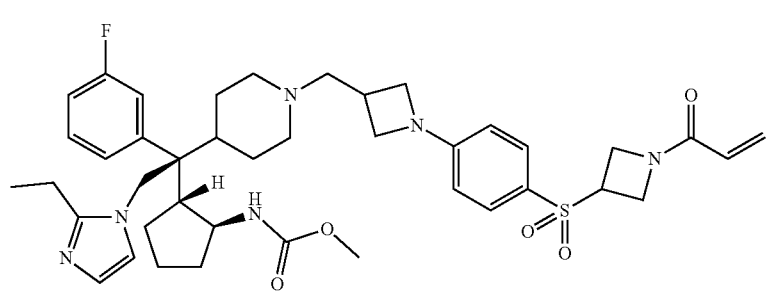

9
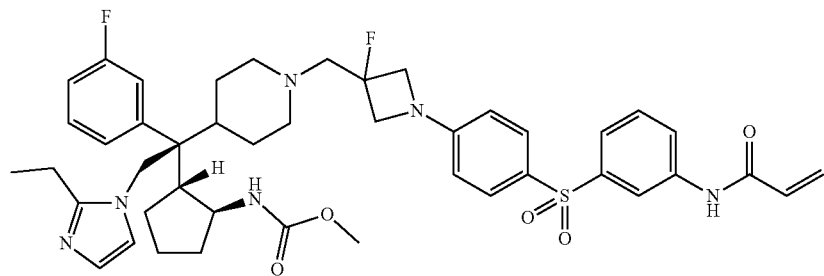
10
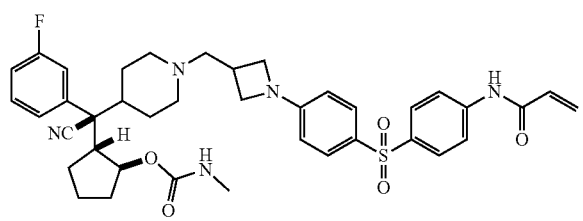
11
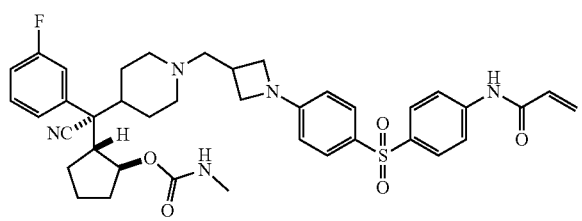
12
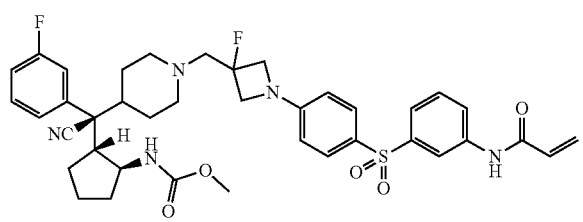
13
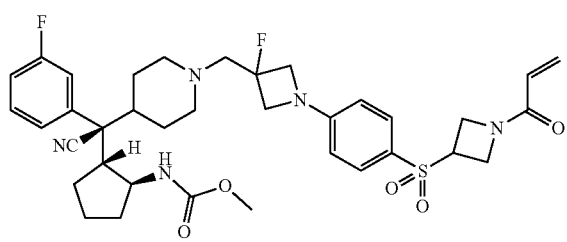
14
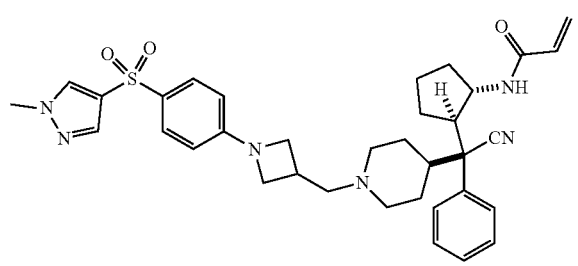
15
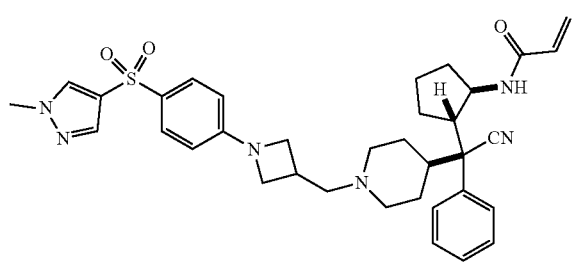
16
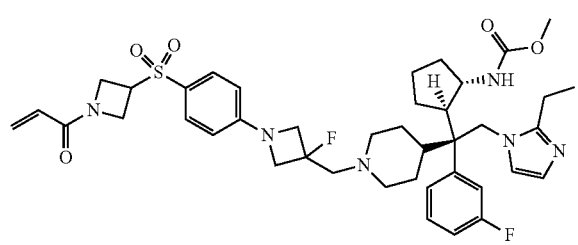
17
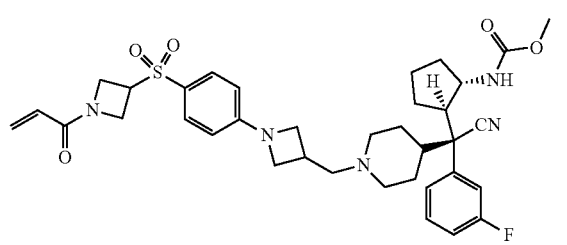
18
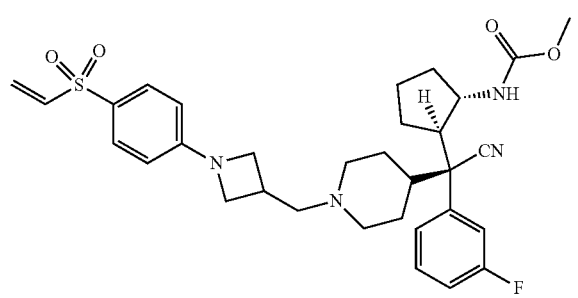
19
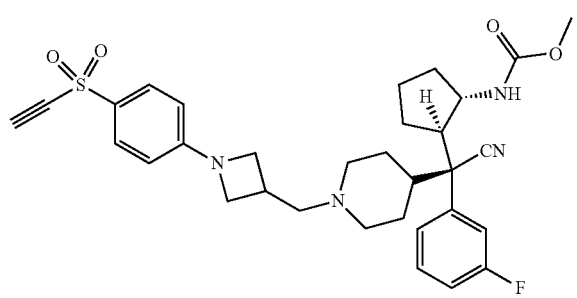

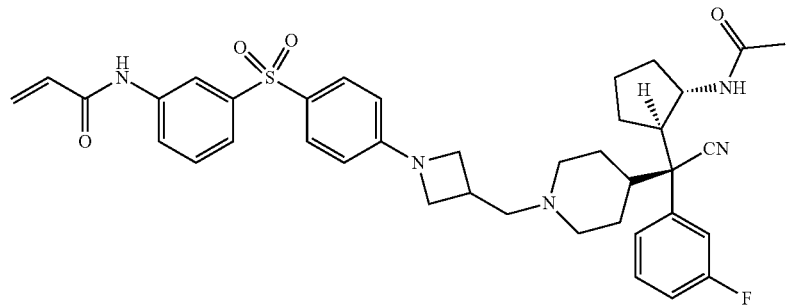
20
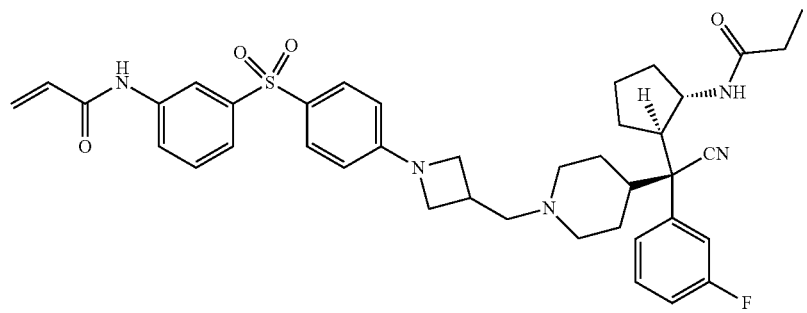
21
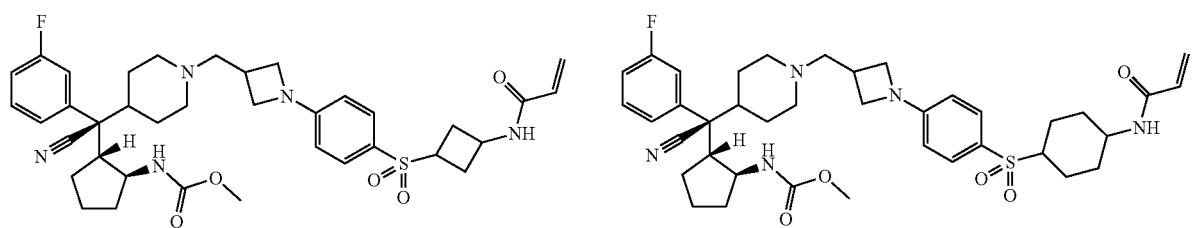
22 23
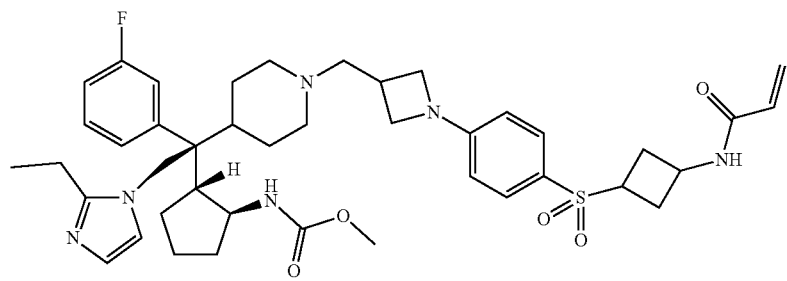
24
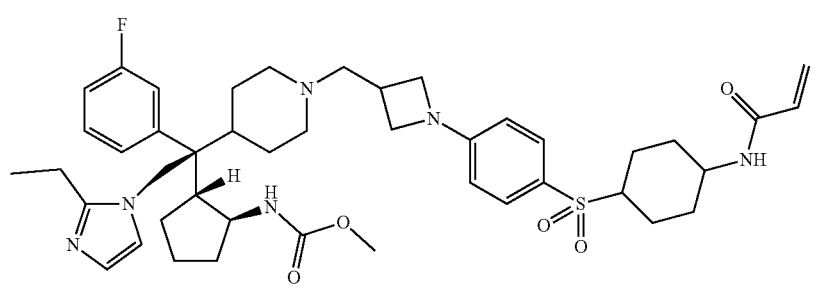
25

-continued
26
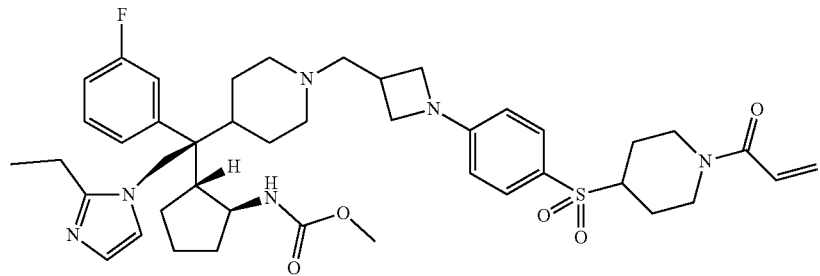
27
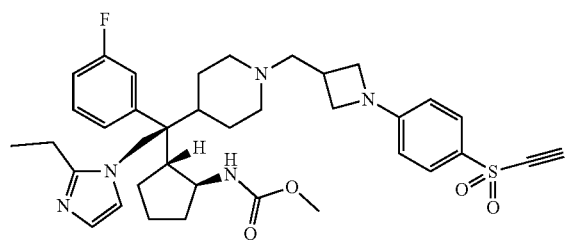
28
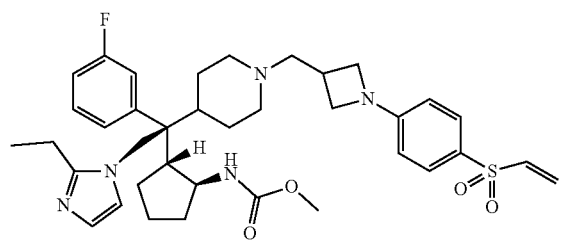
29
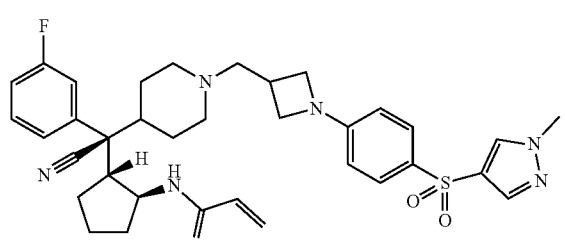
30
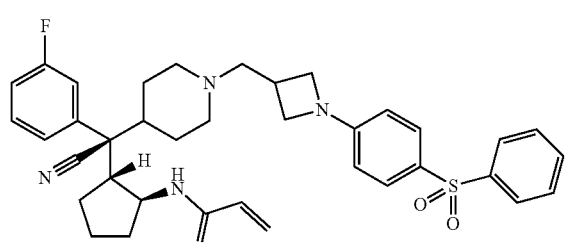
31
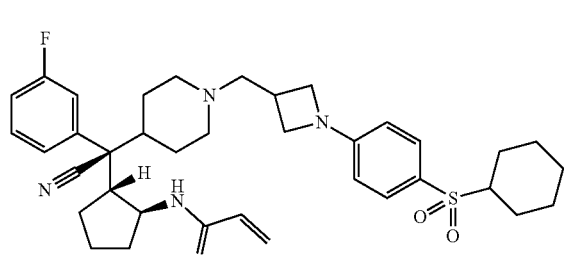
32
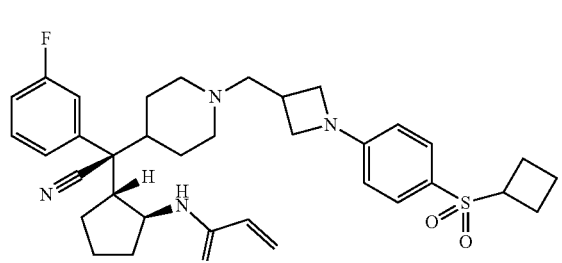
33
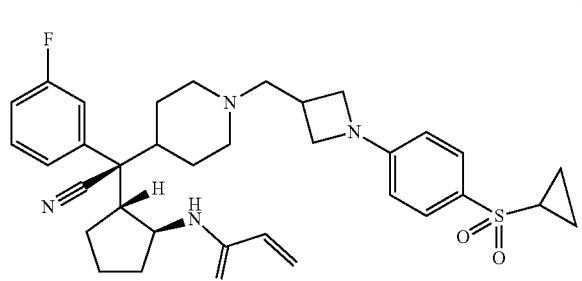
34
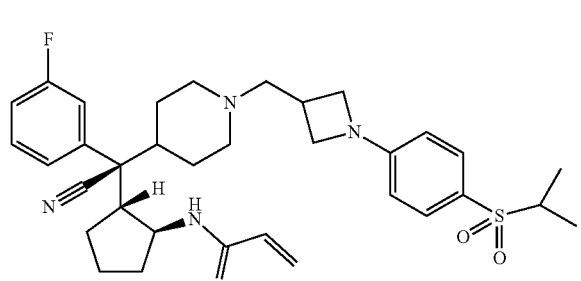
35
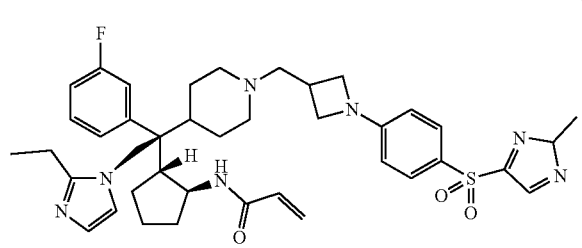
36
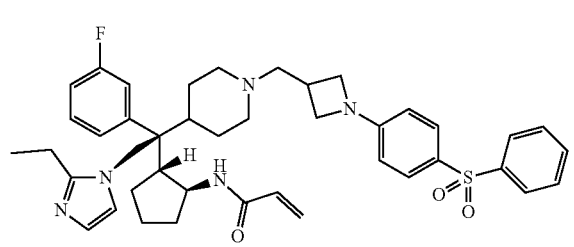

-continued
37
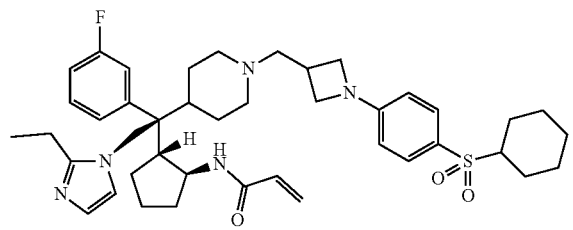
38
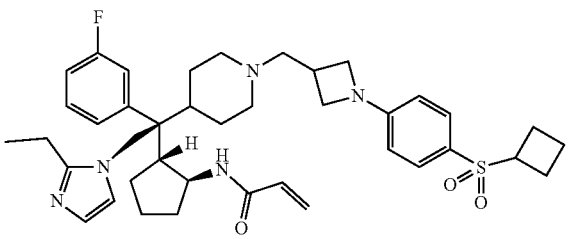
39
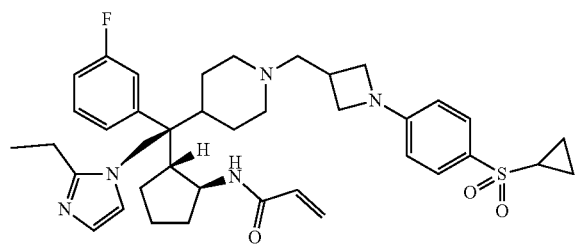
40
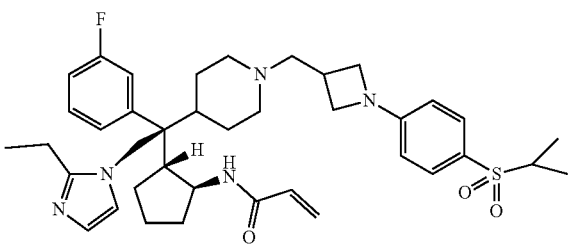
41
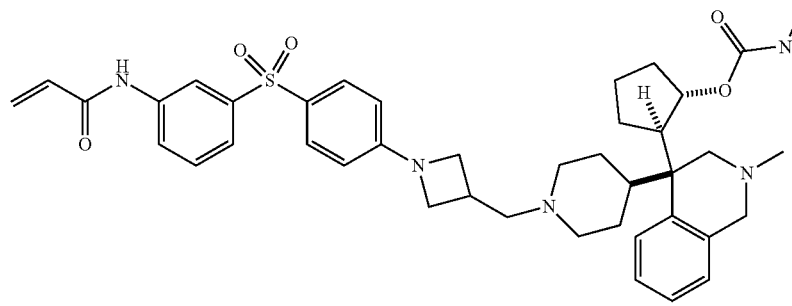
42
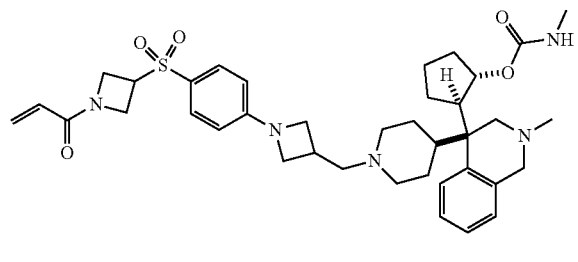
43
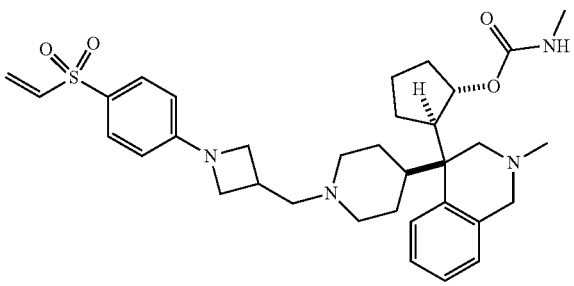
44
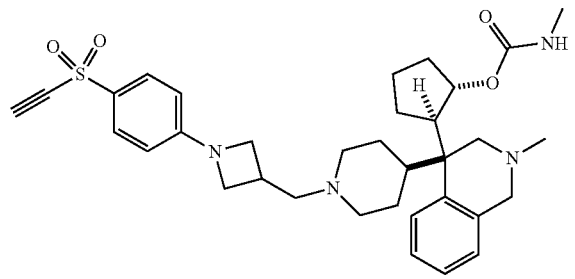
45
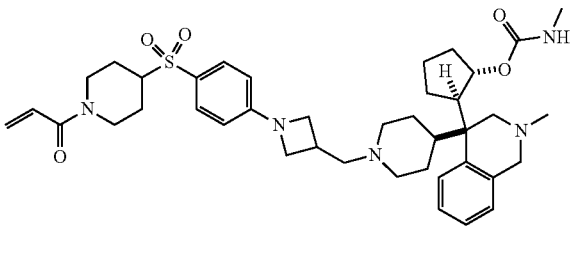

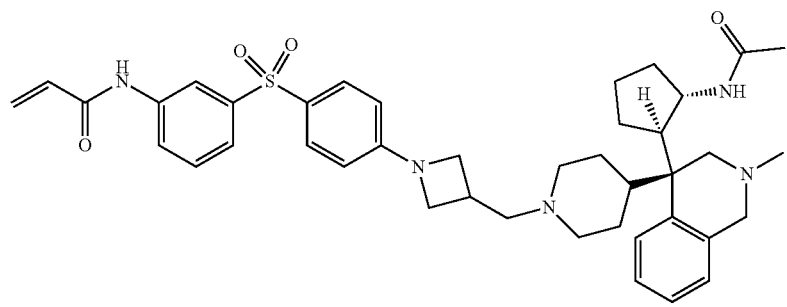
46
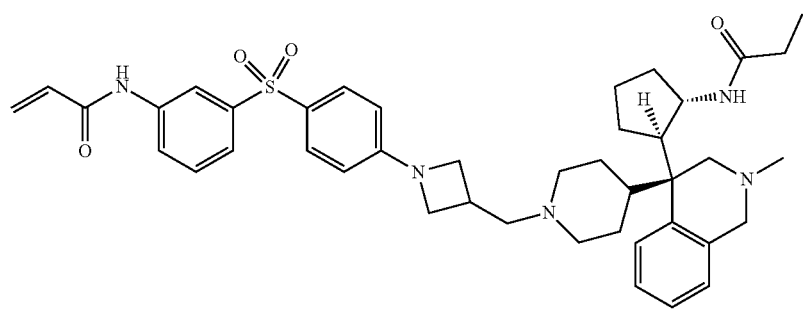
47
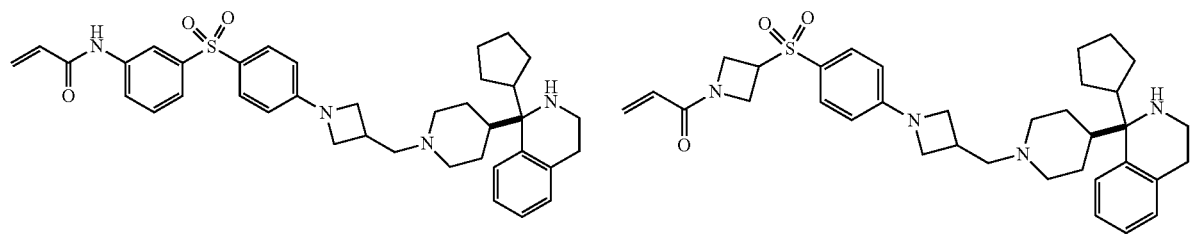
48
49
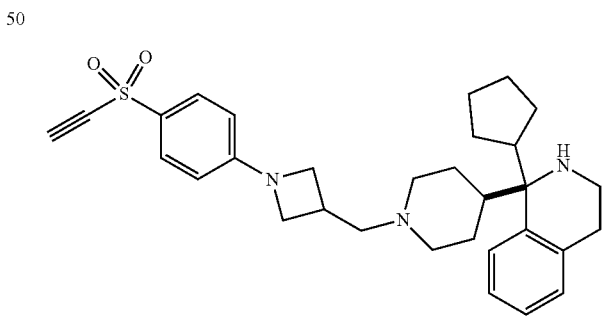
50 51
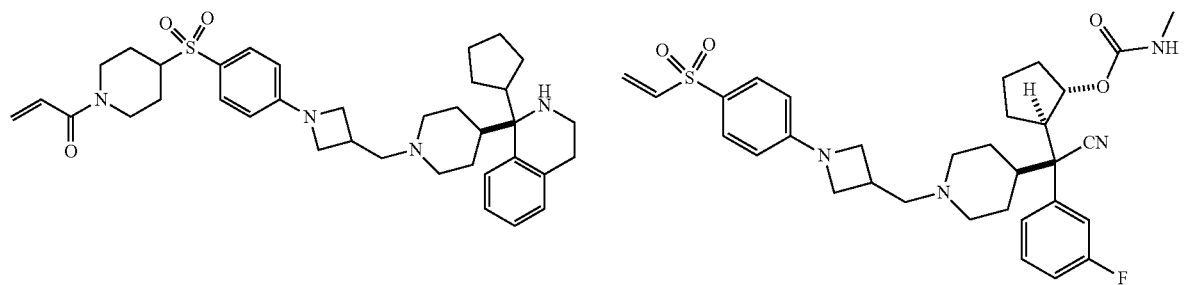
52 53

54
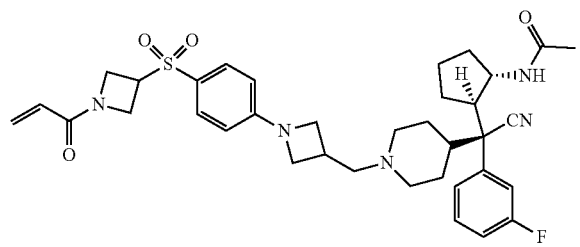
55
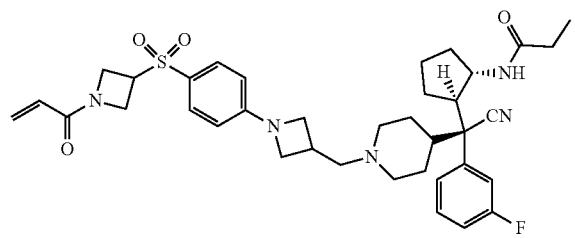
56
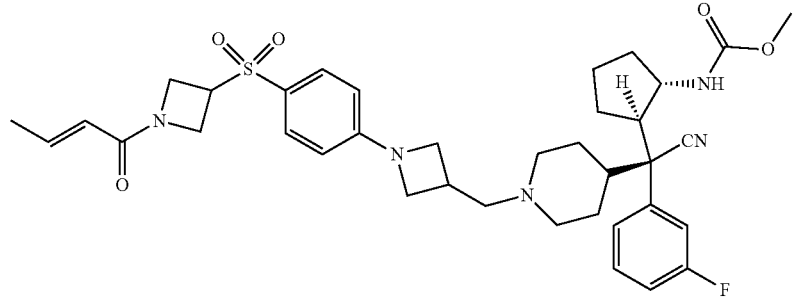
57
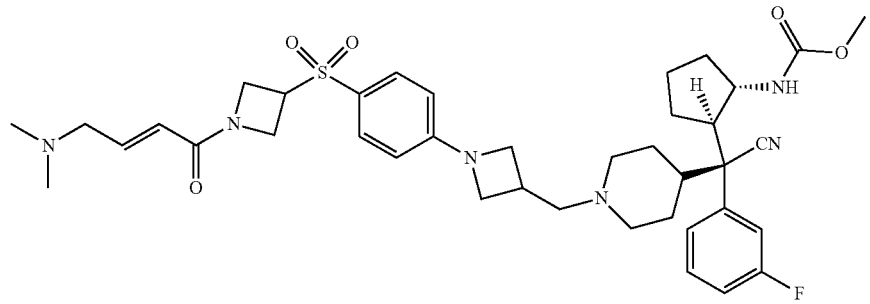
58
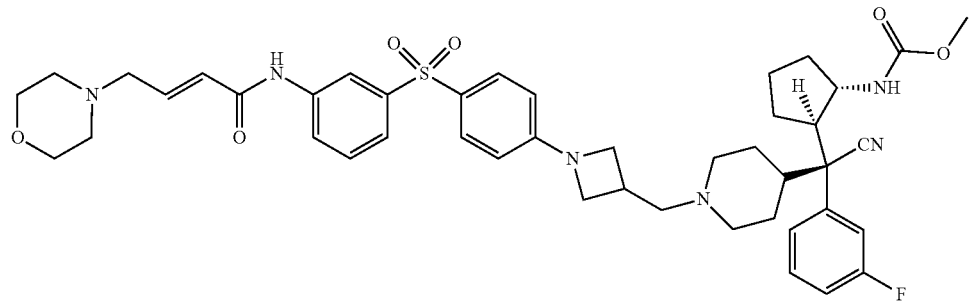
59
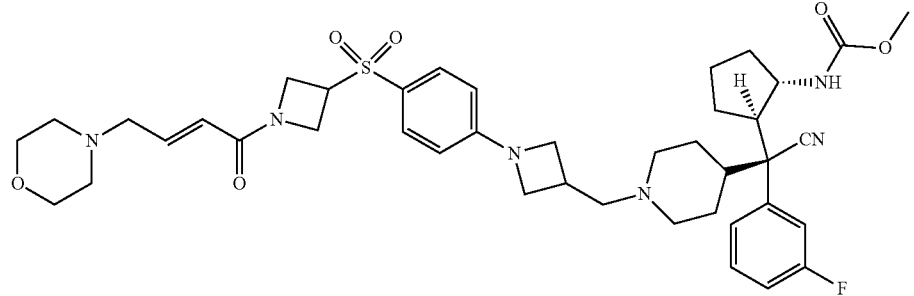

60
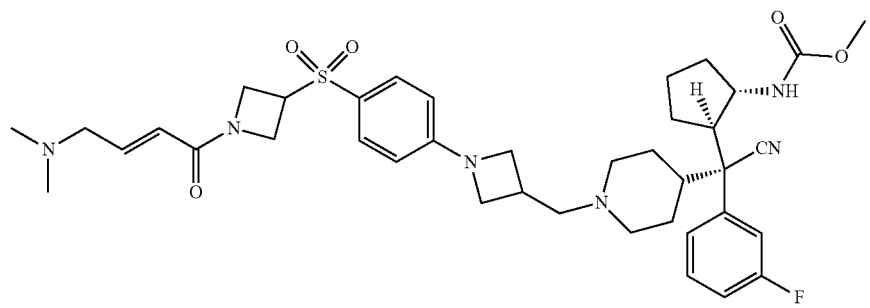
61
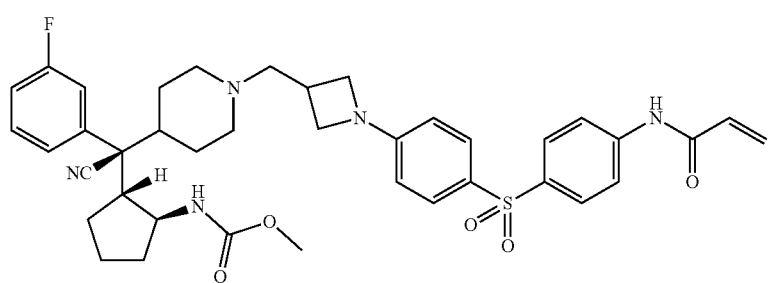
62
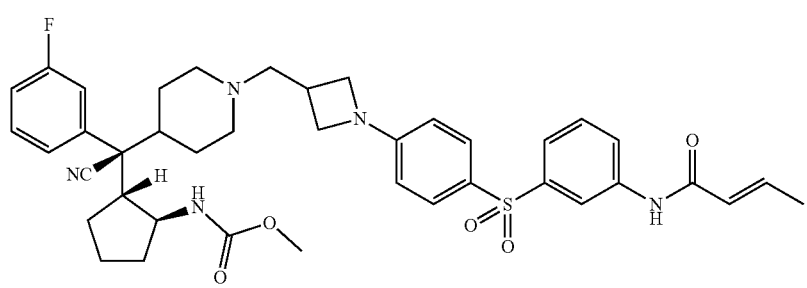
63
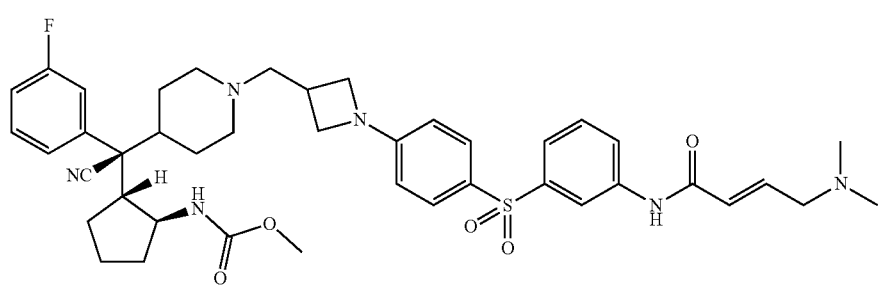
66
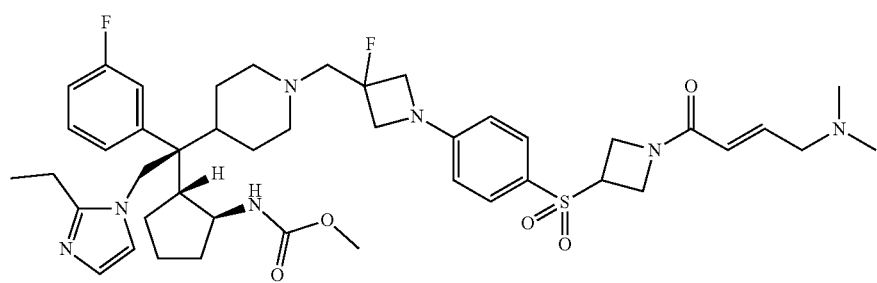

-continued
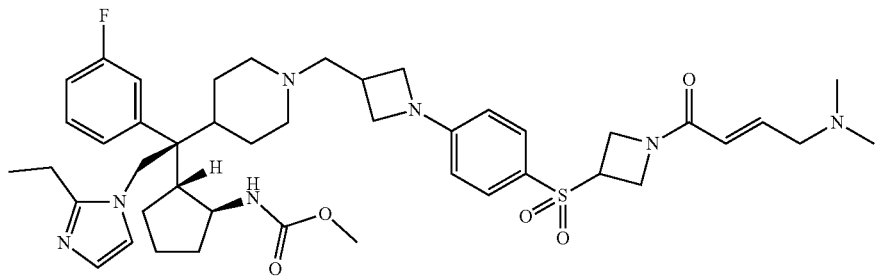
67
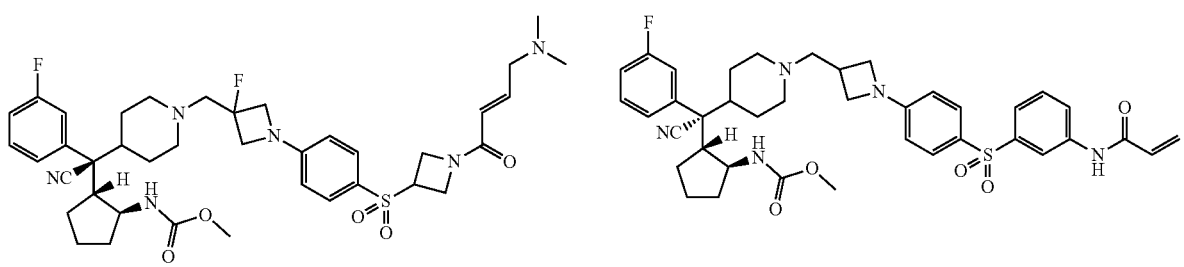
69
70
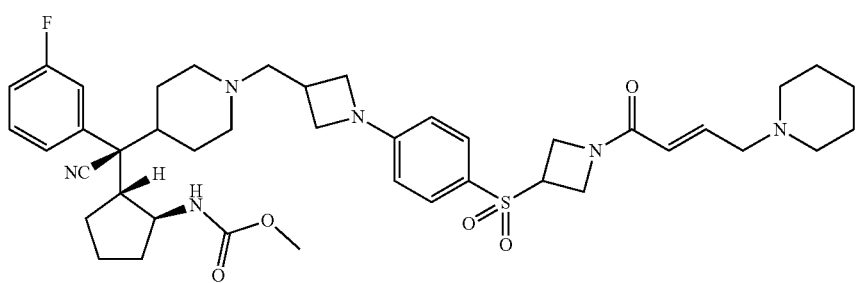
71
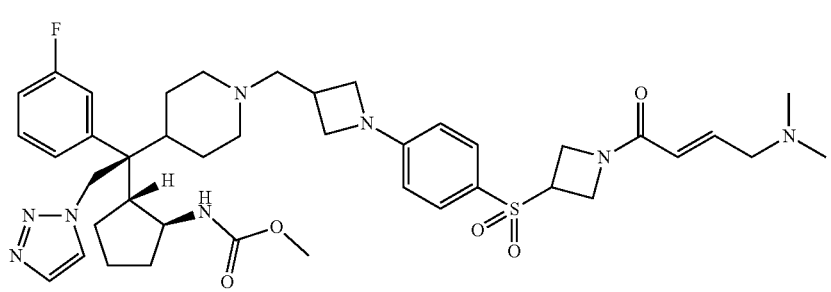
72
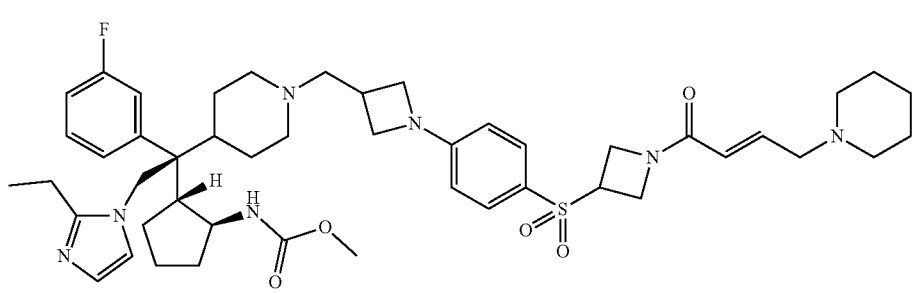
73

-continued

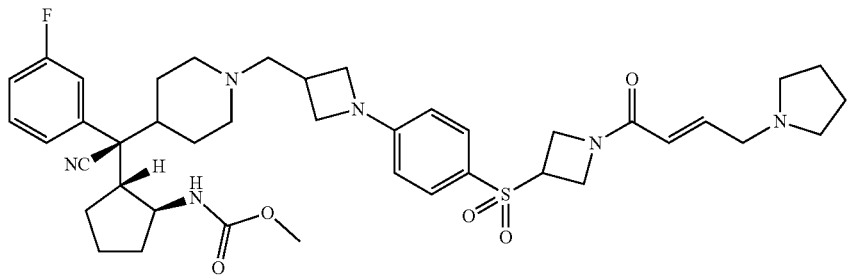

74

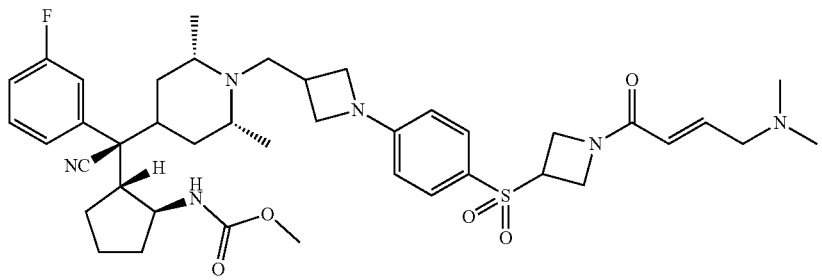

75

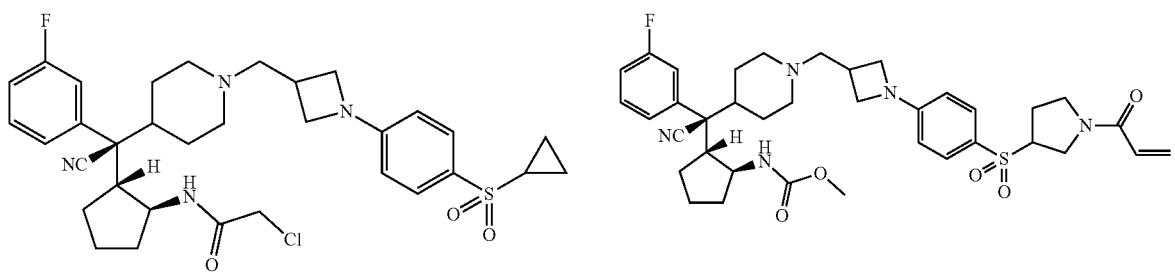

76

77

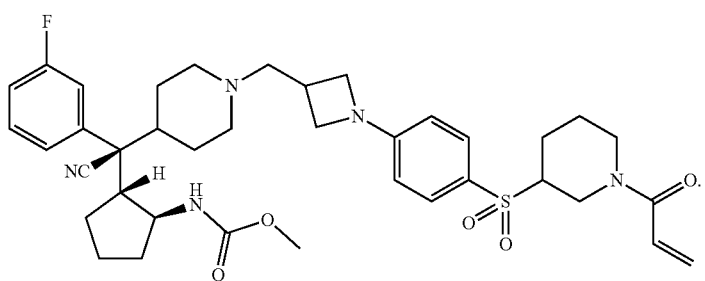

78

19. The compound of claim 11, wherein the compound is selected from the group consisting of:
  methyl ((1S,2R)-2-((S)-cyano(1-(3-(4-((1-((E)-4-(dimethylamino)but-2-enoyl)azetidin-3-yl)sulfonyl) phenoxy)propyl)piperidin-4-yl)(3-fluorophenyl)methyl) cyclopentyl) carbamate;
  methyl ((1S,2R)-2-((R)-(4-(2-(4-((1-acryloylazetidin-3-yl)sulfonyl)phenoxy)ethoxy)phenyl)(cyano)(3-fluorophenyl)methyl)cyclopentyl) carbamate; and
  methyl ((1S,2R)-2-((S)-(4-(2-(4-((1-acryloylazetidin-3-yl)sulfonyl)phenoxy)ethoxy)phenyl)(cyano)(3-fluorophenyl)methyl)cyclopentyl) carbamate, or a pharmaceutically acceptable salt or solvate thereof.

20. The compound of claim 12, wherein the compound is selected from the group consisting of:

N-((1S,2R)-2-((S)-cyano(1-((1-(4-cyanophenyl)azetidin-3-yl)methyl)piperidin-4-yl)(3-fluorophenyl)methyl)cyclopentyl)ethenesulfonamide;
  N-((1S,2R)-2-((S)-cyano(1-((1-(4-cyanophenyl)azetidin-3-yl)methyl)piperidin-4-yl)(3-fluorophenyl)methyl)cyclopentyl)acrylamide;
  2-chloro-N-((1S,2R)-2-((S)-cyano(1-((1-(4-cyanophenyl)azetidin-3-yl)methyl)piperidin-4-yl)(3-fluorophenyl)methyl)cyclopentyl)acetamide; and
  N-((1S,2R)-2-((S)-cyano(1-((1-(4-cyanophenyl)azetidin-3-yl)methyl)piperidin-4-yl)(3-fluorophenyl)methyl)cyclopentyl)propiolamide, or a pharmaceutically acceptable salt or solvate thereof.

21. A pharmaceutical composition comprising the compound of claim 1, or a pharmaceutically acceptable salt or solvate thereof, and a pharmaceutically acceptable carrier.

\* \* \* \* \*